US007887792B2

(12) United States Patent
Chancellor et al.

(10) Patent No.: US 7,887,792 B2
(45) Date of Patent: Feb. 15, 2011

(54) MUSCLE-DERIVED CELLS (MDCS) FOR TREATING MUSCLE- OR BONE-RELATED INJURY OR DYSFUNCTION

(75) Inventors: Michael B. Chancellor, Pittsburgh, PA (US); Johnny Huard, Wexford, PA (US)

(73) Assignee: University of Pittsburgh - of the Commonwealth System of Higher Education, Pittsburgh, PA (US)

( * ) Notice: Subject to any disclaimer, the term of this patent is extended or adjusted under 35 U.S.C. 154(b) by 472 days.

(21) Appl. No.: 11/040,900

(22) Filed: Jan. 21, 2005

(65) Prior Publication Data

US 2005/0265978 A1  Dec. 1, 2005

Related U.S. Application Data

(62) Division of application No. 09/302,896, filed on Apr. 30, 1999, now Pat. No. 6,866,842.

(60) Provisional application No. 60/083,917, filed on May 1, 1998.

(51) Int. Cl.
A61K 48/00 (2006.01)
A01N 63/00 (2006.01)
C12P 21/06 (2006.01)
C12N 5/00 (2006.01)
C12N 15/00 (2006.01)

(52) U.S. Cl. .................. 424/93.1; 424/93.2; 424/93.21; 424/93.3; 514/44 R; 435/69.1; 435/320.1; 435/325; 435/455

(58) Field of Classification Search ....................... None
See application file for complete search history.

(56) References Cited

U.S. PATENT DOCUMENTS

| | | | |
|---|---|---|---|
| 4,424,208 A | 1/1984 | Wallace et al. | |
| 4,965,353 A | 10/1990 | Della Valle et al. | |
| 5,053,050 A | 10/1991 | Itay | 623/16 |
| 5,130,141 A | 7/1992 | Law et al. | 424/548 |
| 5,206,028 A | 4/1993 | Li | 424/484 |
| 5,336,263 A | 8/1994 | Ersek et al. | 623/11 |
| 5,516,532 A | 5/1996 | Atala et al. | 424/548 |
| 5,538,722 A | 7/1996 | Blau et al. | 424/93.21 |
| 5,594,032 A | 1/1997 | Gonzalez-Cadavid et al. | 514/645 |
| 5,667,778 A | 9/1997 | Atala | 424/93.7 |
| 5,833,978 A | 11/1998 | Tremblay | 424/93.7 |
| 5,858,351 A | 1/1999 | Podsakoff et al. | 424/93.2 |
| 5,858,390 A | 1/1999 | Boss | |
| 5,876,447 A | 3/1999 | Arnett | |
| 6,001,654 A | 12/1999 | Anderson et al. | |
| 6,099,832 A | 8/2000 | Mickle et al. | |
| 6,261,832 B1 | 7/2001 | Law | 435/286.5 |
| 6,866,842 B1 | 3/2005 | Chancellor et al. | |
| 7,115,417 B1 | 10/2006 | Chancellor et al. | |
| 2006/0280726 A1 | 12/2006 | Chancellor et al. | |
| 2007/0065416 A1 | 3/2007 | Chancellor et al. | |
| 2007/0065417 A1 | 3/2007 | Chancellor et al. | |

FOREIGN PATENT DOCUMENTS

| | | |
|---|---|---|
| AU | 3775799 A | 11/1999 |
| AU | 5159901 A | 10/2001 |
| AU | 2001251599 B2 | 3/2006 |
| AU | 2006202380 A1 | 6/2006 |
| CA | 2330660 A1 | 11/1999 |
| CA | 2406393 | 11/1999 |
| DE | 60129007 T2 | 2/2008 |
| EP | 1113807 A2 | 7/2001 |
| EP | 1272204 A2 | 1/2003 |
| EP | 1604674 A2 | 12/2005 |
| JP | 2003531125 T | 10/2003 |
| WO | 91/07992 | 6/1991 |
| WO | WO 91/07992 | 6/1991 |
| WO | 94/07999 | 4/1994 |

(Continued)

OTHER PUBLICATIONS

Cossu et al, Trends Mol Med. 10(10):516-20, 2004.*

(Continued)

Primary Examiner—Sumesh Kaushal
(74) Attorney, Agent, or Firm—Mintz, Levin, Cohn, Ferris, Glovsky and Popeo, P.C.; Ivor Elrifi; Sheridan Snedden

(57) ABSTRACT

The present invention provides muscle-derived cells, preferably myoblasts and muscle-derived stem cells, genetically engineered to contain and express one or more heterologous genes or functional segments of such genes, for delivery of the encoded gene products at or near sites of musculoskeletal, bone, ligament, meniscus, cartilage or genitourinary disease, injury, defect, or dysfunction. Ex vivo myoblast mediated gene delivery of human inducible nitric oxide synthase, and the resulting production of nitric oxide at and around the site of injury, are particularly provided by the invention as a treatment for lower genitourinary tract dysfunctions. Ex vivo gene transfer for the musculoskeletal system includes genes encoding acidic fibroblast growth factor, basic fibroblast growth factor, epidermal growth factor, insulin-like growth factor, platelet derived growth factor, transforming growth factor-$\beta$, transforming growth factor-$\alpha$, nerve growth factor and interleukin-1 receptor antagonist protein (IRAP), bone morphogenetic protein (BMPs), cartilage derived morphogenetic protein (CDMPs), vascular endothelial growth factor (VEGF), and sonic hedgehog proteins.

14 Claims, 19 Drawing Sheets

FOREIGN PATENT DOCUMENTS

| | | |
|---|---|---|
| WO | WO 94/07999 | 4/1994 |
| WO | 94/21299 | 9/1994 |
| WO | WO 94/21299 | 9/1994 |
| WO | WO 96/18303 | 6/1996 |
| WO | WO 98/36055 | 8/1998 |
| WO | 98/44142 | 10/1998 |
| WO | 98/54301 | 12/1998 |
| WO | WO 99/47163 | 9/1999 |
| WO | 99/56785 | 11/1999 |
| WO | 99/56786 | 11/1999 |
| WO | 00/17322 A | 3/2000 |
| WO | 00/29552 A | 5/2000 |
| WO | 01/19966 | 3/2001 |
| WO | 01/78754 | 10/2001 |
| WO | 02/067887 | 9/2002 |

OTHER PUBLICATIONS

Mouly et al, Acta Myol. 24(2):128-33 (abstract), 2005.*
Menasché, Prog Cardiovasc Dis. 50(1):7-17, 2007.*
Goldring et al, J Musculoskelet Neuronal Interact. 6(4):376-8, 2006.*
Goldring, Arthritis Rheum. 54(2):387-9, 2006.*
M. Reza Dana et al., "Interleukin-1 Receptor Antagonist Suppresses Langerhans Cell Activity and Promotes Ocular Immune Privilege", *Investigative Ophthalmology & Visual Science*, 1998, 39:70-77.
G. Ferrari et al., "Muscle-Regeneration by Bone Marrow-Derived Myogenic Progenitors", *Science*, 1998, 279:1528-1530.
E. Barr and J. Leiden, "Systemic Delivery of Recombinant Proteins by Genetically Modified Myoblasts", *Science*, 1991, 254:1507-1509.
T. Katagiri et al., "Bone Morphogenetic Protein-2 Converts the Differentiation Pathway of C2C12 Myoblasts into the Osteoblast Lineage", *J. Cell Biology*, 1994, 127:1755-1766.
T.A. Rando and H. Blau, "Primary Mouse Myoblast Purification, Characterization, and Transplantation for Cell-mediated Gene Therapy", *J. Cell Biology*, 1994, 125:1275-1287.
T. Yokoyama et al., "Gene Therapy as a Potential Treatment for BPH; Injection of Myoblast-Adenovirus Transfected with Human Inductible Nitric Oxide Synthase (iNOS) into the Proximal Urethra", *J. Urology*, 1999, 161 (4) Supplement:305 (Abstract 1775).
J. Huard et al., "Myoblast Injection into the Bladder Wall: A Possible Method of Modulating Detrusor Contractility and Cell-Mediated Gene Therapy for Bladder Dysfunction", *J. Urology*, 1998, 159 (5) Supplement:16 (Abstract 62).
J. Huard et al., "Nitric Oxide Synthase (NOS) Gene Therapy for Erectile Dysfunction; Comparison Between Plasmid, Adenovirus and Adenovirus Transduced Myoblast Vectors", *J. Urology*, 1998, 159:90 (Abstract 342).
Z. Qu et al., 1998, "Development of approaches to improve cell survival in myoblast transfer therapy", Journal of Cell Biology, 142;1257-1267.
J. Huard et al.,1992, "Human myoblast transplantation: preliminary results of 4 cases", Muscle and Nerve, 15:550-560.
CS Day et al., 1997, "Myoblast-mediated gene transfer to the joint", Journal of Orthopedic Research, 15:894-903.
G. Bandara et al., 1993, "Inarticular expression of biologically active interleukin 1-receptor-antagonist protein by ex vivo gene transfer", Proc. Natl. Acad. Sci. USA, 90:10764-10768.
G. Acsadi et al., 1994, "A differential efficiency of adenovirus-mediated in vivo gene transfer into skeletal muscle cells of different maturity", Human Molecular Genetics, 3:579-584.
C. Kasemkijwattana et al., 1998, "Development of approaches to improve the healing following muscle contusion", Cell Transplantation, 7:585-598.
KP Spindler et al., 1995, "Regional mitotic response of the meniscus to platelet-derived growth factor (PDGF-AB)", Journal of Orthopedic Research, 13:201-207.
Gussoni et al., 1992, "Normal dystrophin transcripts detected in Duchenne muscular dystrophy patients after myoblast transplantation", Nature, 356:435-438.
Karpati et al., 1993, "Myoblast transfer in Duchenne muscular dystrophy", Annals of Neurology, 34:8-17.
Tremblay et al., 1993, "Results of a triple blind clinical study of myoblast transplantations without immunosuppressive treatment in young boys with Duchenne muscular dystrophy", Cell Transplantation, 2:99-112.
Huard 1994, "High efficiency of muscle regeneration after human myoblast clone transplantation in SCID mice", Journal of Clinical Investigation, 93:586-599.
Huard 1994, "Human myoblast transplantation in Immunodeficient and immunosuppressed mice: evidence of rejection", Muscle and Nerve 17:224-234.
Huard 1995, "The route of administration is a major determinant of the transduction efficiency of rat tissues by adenoviral recombinants", Gene Therapy, 2:107-115.
Alden et al., (1999). Hum. Gene Ther., 10:2245-2253.
Anderson (1998). Nature, 392:25-30.
Andrews et al., (1986). Blood, 67:842-845.
Anwer et al., (1998). Hum. Gene Ther., 9:659-670.
Arcila et al., (1997). J. Neurobiol., 33:185-198.
Ashman et al., (1999). Int. J. Biochem. Cell. Biol. 31:1037-1051.
Atkins et al., (1999). Ann. Thorac. Surg., 67:124-129.
Atkins et al., (1999). J. Heart Lung Transplant., 18:1173-1180.
Baroffio et al., (1996). Differentiation, 60:47-57.
Barr & Leiden (1991). Science, 254:1507-1509.
Beauchamp et al., (1999). J. Cell Biol., 144:1113-1122.
Blanton et al. (1999). Muscle Nerve, 22:43-50.
Cannon et al., (2003). Urology, 62(5):958-963.
Chancellor et al., (2001). Trends Mol. Med., 7(7):301-306.
Civin et al., (1984). J. Immunol. 133:157-165.
Dalle et al., (1999). Gene Ther., 6:157-161.
Deasy et al., (2002). Current Opinion in Molecular Therapeutics, 4:382-389.
Dhawan et al., (1992). Science, 254:1509-1512.
Dominov et al., (1998). J. Cell Biol., 142:537-544.
Faustman et al., (1991). Science, 252:1701.
Ferrari et al., (1998). Science, 279:1528-1530.
Fina et al., (1990). Blood, 75:2417-2426.
Friedmann (2000). Science, 287(5461):2163-2165.
Garban et al., (1997). Biol. Reprod., 56(4):954-963.
Grinnell A. D., (1994). Myology Ed. 2, A. G. Engel & C. F. Armstrong, McGraw-Hill, Inc., 303-304.
Gros et al., (1999). Hum. Gene Ther., 10:1207-1217.
Gross et al., (1999). Muscle & Nerve, 22:174-185.
Gussoni et al., (1999). Nature, 401:390-394.
Hortelano et al., (1999). Hum. Gene Ther., 10:1281-1288.
Huard et al., (1998). J. Urology, 159(5)Supplement:16 (Abstract 62).
Huard et al., (1998). J. Urology, 159:90 (Abstract 342).
Huard et al., (2002). Gene Ther., 9:1617-1626.
Irintchev et al., (1994). Dev. Dynam., 199:326-337.
Jackson et al., (1999). PNAS, 96(25):14482-14486.
Jankowski et al., (2001). Human Gene Therapy, 12:619-628.
Jiao et al., (1992). Brain Research, 575:143-147.
Jung et al., (1999). J. Urology, 162(1):204-212.
Koretzky (1993). FASEB J., 7:420.
Kuby (1994). Immunology, 2nd Ed., WH Freeman Company, pp. 559-560.
Ledley (1996). Pharmaceutical Research, 13(11):1595-1614.
Lee et al., (2000). J. Cell Biol., 150(5):1085-1099.
Lee et al., (2001). J. Urology (Suppl.), 165:254 (Abstract 1033).
Lipton et al., (1979). Science, 205:12924.
Lynch et al., (1992). Proc. Natl. Acad. Sci. USA, 89:1138-1142.
Madeiro et al., (2002). Clin. Exp. Obst. & Gyn., XXIX(2):117-120.
Martini et al., (1995). Anatomy and Physiology, 3rd Ed., Simon & Schuster Company, p. 315.
Miller et al., (1999). Curr. Top. Dev. Biol., 43:191-219; see Table 3.
Moisset et al., (1998). Biochem. Biophys. Res. Commun., 247:94-99.
Moisset et al., (1998). Gene Ther., 5:1340-1346.
Morgan et al., (1988). J. Neural. Sci., 86:137.
Murry et al., (1996). J. Clin. Invest., 98:2512-2523.
Musgrave et al., (1998). Gene Therapy & Molecular Biology, 3:1-15.
Newman et al., (2003). Am. J. Nurs., 103(8):46-55.

Nurcombe et al., (1985). Developmental Brain Research, 21:49-60 (Abstract).
Osawa et al., (1996). J. Immunol. 156:3207-3214.
Partridge et al., (1978). Nature, 73:306-308.
Partridge et al., (1989). Nature, 337:176.
Partridge T. A. & K. E. Davies, (1995). Brit. Med. Bulletin, 51:123-137.
Pittenger et al., (1999). Science, 284:143-147.
Price et al., (1987). Proc. Natl. Acad. Sci. USA, 84:156.
Regulier et al., (1998). Gene Ther., 5:1014-1022.
Richler et al., (1970). Developmental Biology, 23:1-22.
Roman et al., (1992). Somat. Cell. Mol. Genet., 18:247-258.
Rosenberg et al., (2000). Science, 287:1751.
Sanes et al., (1986). EMBO J. 5:3133.
Saini et al., (2006). Curr. Stem Cell Res. Ther. 1(2):157-171.
Seale et al., (2000). Developmental Biology, 218:115-124.
Simmons et al., (1991). Blood, 78:2848-2853.
Smith et al., (1997). Cell Growth and Differentiation, 8(8):927-934.
Tirney et al., (2001). Mol. Urol. Spring, 5(1):37-43.
Tremblay et al., (1997). Basic Appl. Myol., 7(3&4):221-230.
Tzeng et al., (1996). Surgery, 120(2):315-321.
Van de Rijn et al., (1989). Proc. Natl. Acad. Sci. USA, 86:4634-4638.
Vandenburgh (1996). Hum. Gene Ther., 7:2195-2200.
Verma (2000). Mol. Ther., 1:493.
Wang et al., (1997). Blood, 90:1075-1082.
Watt et al., (1984). Clin. Exp. Immunol. 55:419.
Webster et al., (1988). Exp. Cell. Res. 174:252-65.
Yamanishi et al., (2002). J. Urology, 168:2706-2710.
Yao et al., (1994). Gene Ther., 1:99-107.
Yokoyama et al., (1999). J. Urology, 161(4)Supplement:305 (Abstract 1775).
Yokoyama et al., (2000). World J. Urology, 18:56-61.
Yokoyama et al., (2001). J. Urology, 165:271-276.
Yokoyama et al., (2001). Urology, 57(4):826-831.
Yokoyama et al., (2001). Tissue Engineering, 7(4):395-404.
Yoshida et al., (1998). J. Cell Science. 111:769-779.
Young et al., (1993). In vitro Cell Dev. Biol., 29A:723-736.
Young et al., (1995). Dev. Dynam., 202:137-144.
Ziegler et al., (1999). Science 285:1533-1558.
Office Action for Canadian Application No. 2,330,660, Dated Jun. 20, 2008.
Chancellor et al., (2000), Neurourology and Urodynamics, 19(3):279-287.
Supplementary European Search Report, Appl. No. EP 02706457, Mailed on May 27, 2009.
Fukuda et al., (2000), Tanpakushita Kakusan Kouso (Protein, Nucleic Acid and Enzyme) 45(13), 2078-2084.
Ikada (2001), "Tissue Engineering—Toward Establishing of Basic Technology and Clinical Applications," Kagaku-Dojin Publishing Co., Inc. pp. 183-191.
Japanese Office Action, Application No. JP2002-567239, Date: Feb. 7, 2007 (with English Translation).
Pre-Appeal Examination Report, Appl. No. JP2002-567239, Date: Oct. 22, 2007 (with English Translation).
Ou et al., (1999). Molec. Biol. of the Cell, 10 (Suppl.):246a.
Office Action for Canadian application No. 2,406,393, dated Mar. 13, 2009.
Elia et al., Database EMBASE (1995) Accession No. EMB-1995233867; Abstract.
Huard et al., J. Urol., (1999), 161(4) Suppl.:66.
Somogyi et al., J. Urol., (1999), 161(4) Suppl.:43.
Tirney et al., J. Urol., (1998), 159(5) Suppl.:327.
Yokoyama et al., J. Urol., (1999), 161(4) Suppl.:307.
Torrente, et al., "Intraarterial Injection of Muscle-derived CD34+Sca-1+ Stem Cells Restores Dystrophin in mdx Mice", J. of Cell Biology, vol. 152, No. 2, pp. 335-348, (2001).
Kaufman et al. (1988), PNAS, 85:9606-9610.
Qu et al., (1999), Molec. Biol. of the Cell, 10 (Suppl.):246a.
Chancellor et al., (2000), Neurourology and Urodynamics, 19(3):279-287.
Fukuda et al., (2000), Tanpakushita Kakusan Kouso (Protein, Nucleic Acid and Enzyme) 45(13), 2078-2084.
Ikada (2001), "Tissue Engineering—Toward Establishing of Basic Technology and Clinical Applications," Kagaku-Dojin Publishing Co., Inc. pp. 183-191.
Yokoyama et al., (2001). Urology, 57(4):826-831.
Yokoyama et al., (2001). Tissue Engineering, 7(4):395-404.
Yoshida et al., (1998). J. Cell Science. 111:769-779.
Young et al., (1993). In vitro Cell Dev. Biol., 29A:723-736.
Young et al., (1995). Dev. Dynam., 202:137-144. .
Ziegler et al., (1999). Science 285:1533-1558.

* cited by examiner

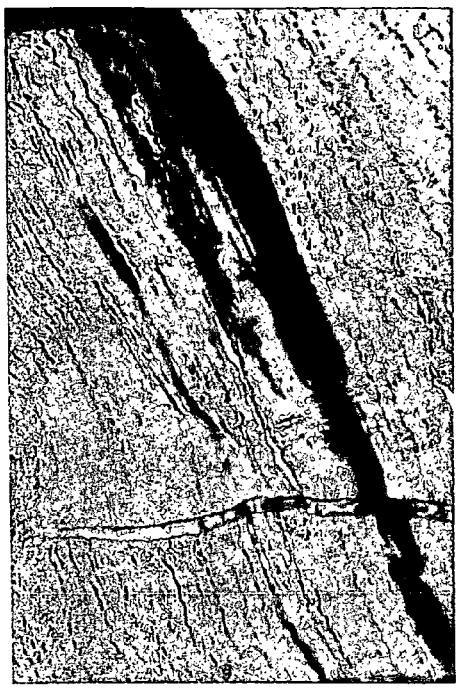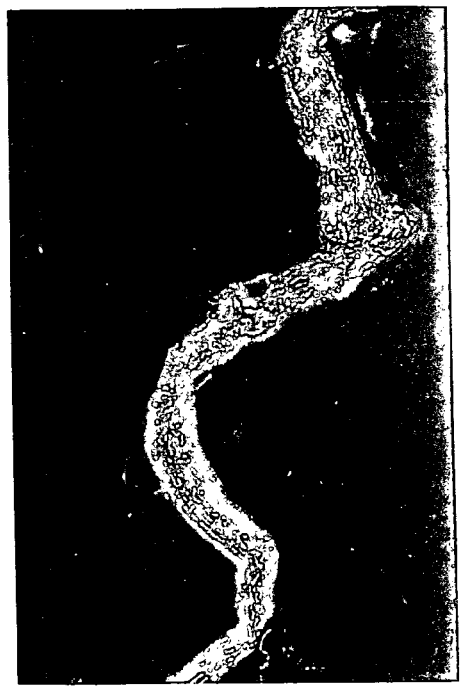
FIG. 6A
FIG. 6B
FIG. 6C
FIG. 6D

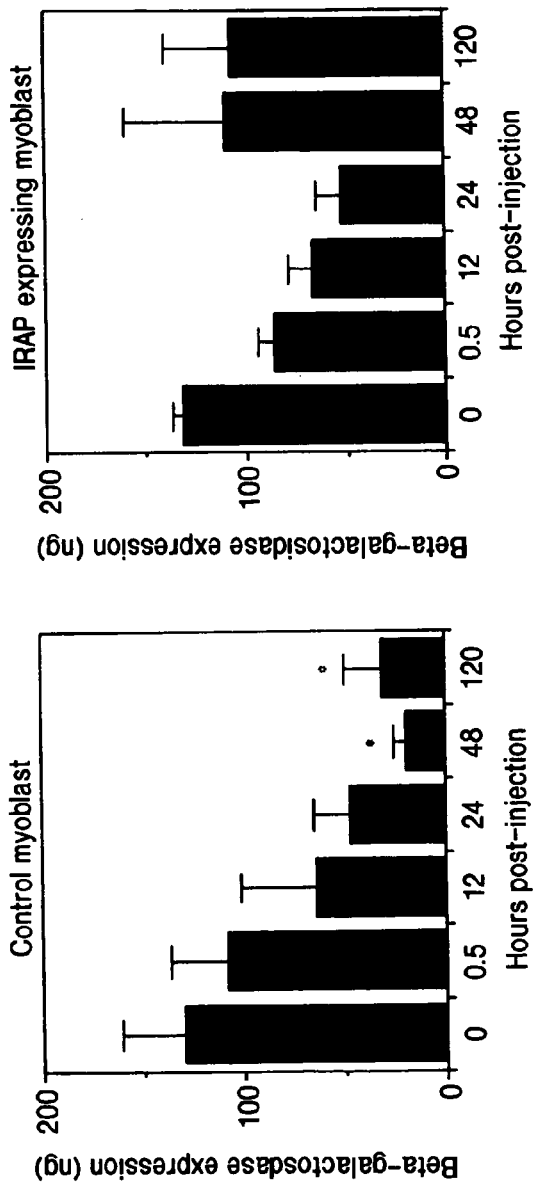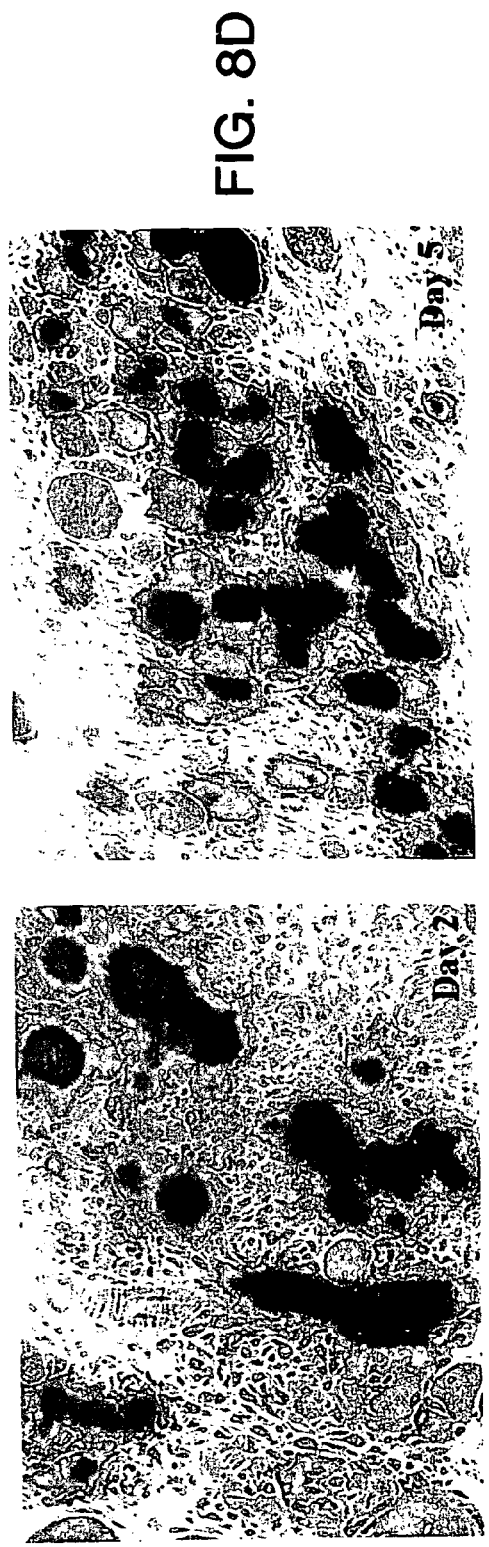
FIG. 8A
FIG. 8B
FIG. 8C
FIG. 8D

M= Muscle    C= Cartilage

MUSCLE-DERIVED CELLS (MDCS) FOR TREATING MUSCLE- OR BONE-RELATED INJURY OR DYSFUNCTION

CROSS REFERENCE TO RELATED APPLICATIONS

This application is a divisional of U.S. patent application Ser. No. 09/302,896 filed on Apr. 30, 1999, which claims the benefit of Provisional Patent Application U.S. Ser. No. 60/083,917, filed May 1, 1998, the entire disclosures of which are hereby incorporated by reference.

GOVERNMENT INTERESTS

This invention was made with Government support under Grant No. DK055387 awarded by the National Institutes of Health. The Government has certain rights to this invention.

FIELD OF THE INVENTION

The present invention relates generally to compositions and methods comprising myogenic or muscle-derived cells, including myoblasts and muscle-derived stem cells (also termed MDC herein) for tissue engineering and cell-mediated gene therapy. The invention further relates to the introduction of exogenous nucleic acids into muscle-derived cells, including myoblasts and muscle-derived stem cells, resulting in the expression of one or more gene products by the genetically engineered muscle-derived cells. Such engineered cells are then capable of producing the gene products and effecting an enhanced physiological response after administration to a recipient host, including humans.

BACKGROUND OF THE INVENTION

A number of defects, diseases and pathological conditions in a variety of areas of medicine would benefit from the development of noninvasive treatments utilizing improved gene delivery vehicles and systems that allow the safe, efficient and sustained production of gene products to an affected tissue or organ site. In particular, improved cell-mediated gene delivery vehicles and methods would find wide use in ameliorating non-fatal, yet debilitating, pathologies of the musculoskeletal system, such as arthritis and joint disease (e.g., ligament, meniscus and cartilage); the bone, such as segmental bone defects and non-unions; and the genitourinary system, such as urinary incontinence and bladder conditions.

Although synovial cells have been used to deliver potentially therapeutic agents into the joint, the expression of such agents has declined over time, thereby causing these agents generally to become undetectable after about four to six weeks. (G. Bandara et al., 1993, Proc. Natl. Acad. Sci. USA, 90(22):10764-10768; C. H. Evans and P. D. Robbins, 1995, Ann. Med., 27(5):543-546; C. H. Evans and P. D. Robbins, 1994, J. Rheum., 21(5):779-782). This decline in expression over time may be ameliorated by the use of cell mediated gene delivery employing a myogenic cell type that becomes post-mitotic with differentiation, in accordance with the present invention.

Segmental bone defects and non-unions are relatively common problems facing all orthopedic surgeons. Osteogenic proteins, e.g., bone morphogenic protein-2, BMP-2), can promote bone healing in segmental bone defects. However, a large quantity of the human recombinant protein is needed to enhance bone healing potential. Moreover, current modes of delivering such quantities of protein, i.e., a biological allograft or a synthetic carrier, are hampered by limited availability, possible disease transmission and the need for further research and investigation.

Cell mediated gene therapy in the bone defect would allow a sustained expression of osteogenic proteins, further enhance bone healing, and offer a solution to the problems surrounding current methods of bone protein delivery. Thus, in accordance with the present invention, the utilization of muscle-derived cells, e.g., myoblasts, as cellular gene delivery vehicles to correct or improve a bone defect, provides an important step in establishing a less invasive treatment for non-unions and segmental bone defects.

Ex vivo gene therapy and myoblast transplantation are two closely related methods which require in vitro cell isolation and culture. Ex vivo techniques involve muscle biopsy and myogenic cell isolation (T. A. Rando et al., 1994, J. Cell Biol., 125:1275-1287; Z. Qu et al., 1998, J. Cell Biol., 142(5):1257-1267). The isolated muscle-derived cells are transduced in vitro with the desired gene carrying vector. The satellite cells are then reinjected into skeletal muscle, fuse to form post-mitotic myotubes and myofibers, and begin growth factor production. This technique is feasible with adenoviral, retroviral, and herpes simplex viral vectors.

The following are examples of orthopaedic applications for muscle based gene therapy and tissue engineering related to the practice of the present invention:

Muscle Injury and Repair

Muscle injuries comprise a large percentage of recreational and competitive athletic injuries. Muscle injuries may result from both direct (e.g., contusions, lacerations) and indirect (e.g., strains, ischemia and neurological injuries) trauma. Upon injury, satellite cells are released and activated in order to differentiate into myotubes and myofibers, thereby promoting muscle healing. However, this reparative process is usually incomplete and accompanied by a fibrous reaction producing scar tissue. This scar tissue limits the muscle's potential for functional recovery (T. Hurme et al., 1991; Med. Sci. Sports Exerc., 23:801-810; T. Hurme et al., 1992, Med. Sci. Sports Exerc., 24:197-205).

Investigations in animals have identified possible clinical applications for muscle-based tissue engineering to treat muscle injuries (W. E. Garrett et al., 1984; J. Hand Surgery (Am). 9A:683-692; W. E. Garrett et al., 1990, Med. Sci. Sports Exerc., 22:436-443). Injured skeletal muscle releases numerous growth factors acting in autocrine and paracrine fashion to modulate muscle healing. These proteins activate satellite cells to proliferate and differentiate into myofibers (T. Hurme, 1992, Med. Sci. Sports Exerc., 24:197-205; R. Bischoff, 1994, "The satellite cell and muscle regeneration". Myology. 2nd Edition. New York, McGraw-Hill, Inc, pp. 97-118; H. S. Allamedine et al., 1989; Muscle Nerve, 12:544-555; E. Schultz et al., 1985, Muscle Nerve, 8:217; E. Schultz, 1989, Med. Sci. Sports Exerc., 21:181).

Muscle-based tissue engineering offers exciting potential therapies for muscle disorders. A large number of recreational and professional athletic injuries involve skeletal muscle (Garrett et al., 1990, Med. Sci. Sports Exerc., 22:436-443). Therapies to improve functional recovery and shorten rehabilitation may both optimize performance and minimize morbidity. Further research is ongoing to refine these muscle-based tissue engineering applications. The results of such investigations may provide revolutionary treatments for these common muscle injuries. The present invention provides new and exciting treatments for muscle repair following muscle-based injuries, particularly for application in clinical settings.

Bone Healing

Multiple surgical specialties, including orthopaedic, plastic, and maxillofacial, are concerned with bone healing augmentation. Physicians in these disciplines rely on bone augmentation techniques to improve healing of fracture non-unions, oncologic and traumatic bone defect reconstructions, joint and spine fusions, and artificial implant stabilizations. Unfortunately, current techniques of autograft, allograft, and electrical stimulation are often suboptimal. Therefore, tissue engineering approaches toward bone formation have immense implications.

Intramuscular bone formation is a poorly understood phenomenon. It can be present in the clinically pathologic states of heterotopic ossification, myositis ossificans, fibrodysplasia ossificans progressiva and osteosarcoma. Radiation therapy and the anti-inflammatory drug, indomethicin, can suppress myositis ossificans. However, neither the mechanism of formation nor suppression of ectopic bone is clearly understood. A growing family of bone morphogenetic proteins (BMPs), members of the transforming growth factor $\beta$ (TGF-$\beta$) superfamily, are recognized as being capable of stimulating intramuscular bone. Human BMP-2 in recombinant form (rhBMP-2) and BMP-encoding cDNA contained in a plasmid construct induce bone formation when injected into skeletal muscle (E. A. Wang et al., 1990, *Proc. Natl. Acad. Sci. USA*, 87:2220-2224; J. Fang et al, 1996, *Proc. Natl. Acad. Sci. USA*, 93:5753-5758). Current applications focus on injecting rhBMP-2 directly into non-unions and bone defects. However, muscle-based tissue engineering has enormous promise in the arena of bone healing and may shed light on the physiologic mechanism of ectopic bone formation.

Intraarticular Disorders

Degenerative and traumatic joint disorders are encountered frequently as our population becomes more active and lives longer. These disorders include arthritis of various etiologies, ligament disruptions, meniscal tears, and osteochondral injuries. Currently, the clinician's tools consist primarily of surgical procedures aimed at biomechanically altering the joint, such as anterior cruciate ligament (ACL) reconstructions, total knee replacement, meniscal repair or excision, cartilage debridement, etc. Tissue engineering applied to these intraarticular disease states theoretically offers a more biologic and less disruptive reparative process.

Both direct (I. Nita et al., 1996, *Arthritis Rheum.*, 39:820-828) and ex vivo (G. Bandara et al., 1993, *Proc. Natl. Acad. Sci. USA*, 90:10764-10768) gene therapy approaches to arthritis models have been reported. The synovial cell-mediated ex vivo approach, while offering advantages of ex vivo gene transfer such as the safety of in vitro genetic manipulation and precise cell selection, is hindered by a decline of gene expression after 5-6 weeks (Bandara et al., 1993, Ibid.). Due to its ability to form post-mitotic myotubes and myofibers, the satellite cell offers the theoretical advantages of longer term and more abundant protein production.

Muscle cell-mediated ex vivo gene delivery to numerous intraarticular structures is possible. Intraarticular injection of primary myoblasts, transduced by adenovirus carrying the $\beta$-galactosidase marker gene, results in gene delivery to many intraarticular structures (C. S. Day et al., 1997, *J. Orthop. Res.*, 15:227-234). Tissues expressing $\beta$-galactosidase at 5 days after injection in the rabbit knee include the synovial lining, meniscal surface, and cruciate ligament (Ibid.). In contrast, injection of transduced synovial cells results in $\beta$-galactosidase expression only in the synovium (Ibid.). Likewise, injection of transduced immortalized myoblasts results in gene delivery to various intraarticular structures, including the synovial lining and patellar ligament surface. However, the purified immortalized myoblasts fused more readily and resulted in more de novo intraarticular myofibers than the primary myoblasts. This illustrates the importance of obtaining a pure population of myogenic cells, void of the fibroblast and adipocyte contamination often seen in primary myoblasts.

Muscle cell-mediated ex vivo approaches are predicated on myoblast fusion to form myofibers, the plurinuclear protein-producing factories. Intraarticular injection of transduced immortalized myoblasts into a severe combined immune deficient (SCID) mouse results in myotube formation and transgene expression in multiple structures at 35 days. Therefore, intraarticular gene expression (for at least 35 days) resulting from muscle cell-mediated tissue engineering is feasible in animal models. Based on this data, a muscle cell-mediated gene transfer approach may deliver genes to improve the healing of several intraarticular structures specifically to the ACL and meniscus.

The ACL is the second most frequently injured knee ligament. Unfortunately, the ACL has a low healing capacity, possibly secondary to its encompassing synovial sheath or the surrounding synovial fluid. Because complete tears of the ACL are incapable of spontaneous healing, current treatment options are limited to surgical reconstruction using autograft or allograft. The replacement graft, often either patella ligament or hamstring tendon in origin, undergoes ligamentization with eventual collagen remodeling (S. P. Arnosczky et al., 1982, *Am. J. Sports Med.*, 10:90-95). Therefore, augmentation of this ligamentization process using growth factors to affect fibroblast behavior is envisioned by the practice of the methods described herein. In vivo data suggests that platelet-derived growth factor (PDGF), transforming growth factor-$\beta$ (TGF-$\beta$), and epidermal growth factor (EGF) promote ligament healing (N. A. Conti et al., 1993, *Trans. Orthop. Res. Soc.*, 18:60). Transient, low levels of these growth factors resulting from their direct injection into the injured ligament are unlikely to produce a significant response. Therefore, an efficient delivery mechanism is essential to the development of a clinically applicable therapy. Muscle cell-mediated ex vivo gene therapy according to the teachings herein offers the potential to achieve persistent local gene expression and subsequent growth factor delivery to the ACL.

With more specific regard to the knee, the knee meniscus plays a critical role in maintaining normal knee biomechanics. Primary functions of the meniscus include load transmission, shock absorption, joint lubrication, and tibiofemoral stabilization in the ACL deficient knee. The historical treatment of meniscectomy for meniscal tears has been replaced by meniscal repair when tears involve the meniscus' peripheral, vascular third. Growth factors, including platelet-derived growth factor (PDGF), are capable of enhancing meniscal healing (K. P. Spindler et al., 1995, *J. Orthop. Res.*, 13(2):201-207). However, needed for both the practitioner and the patient are better methods and procedures to deliver such needed factors to the meniscus to provide healing and repair.

Urologic Applications

Urinary incontinence is a devastating medical and social condition. The incidence of urinary incontinence is increasing in the United States due to an aging population. As of January 1997, the National Institute of Diabetes and Digestive and Kidney Disease has launched a public health campaign to address the fact that there are over eleven million women and four million men in the United States who have urinary incontinence problems. Approximately half of the fifteen million people with incontinence have stress urinary incontinence; however, less than half of the afflicted people are seeking help and receiving the treatments which are available (Agency for Health Care Policy and Research, AHCPR, 1992 and 1996).

Presently, the estimated annual cost for treating people with urinary incontinence is over $16 billion in the United States. Most of this money is spent on management measures, such as adult diapers and pads, rather than on treatment. Since most of the invasive and surgical treatment for urinary incontinence involves the treatment of stress urinary incontinence, the cost for managing stress urinary incontinence is estimated at $9 billion dollars per year in the United States (AHCPR 1996).

In evaluating an individual with incontinence, three of the most common types and causes of incontinence can be identified: a) urge incontinence, b) stress incontinence, or c) overflow incontinence (M. B. Chancellor and J. G. Blaivas, 1996, *Atlas of Urodynamics*, Williams and Wilkins, Philadelphia, Pa.).

Stress incontinence is the involuntary loss of urine during coughing, sneezing, laughing, or other physical activities which increase abdominal pressure. This condition may be confirmed by observing urine loss coincident with an increase in abdominal pressure, in the absence of a bladder contraction or an overdistended bladder. The condition of stress incontinence may be classified as either urethral hypermobility or intrinsic sphincter deficiency. In urethral hypermobility, the bladder neck and urethra descend during cough or strain on urodynamic and the urethra opens with visible urinary leakage (leak point pressure between 60-120 cm $H_2O$). In intrinsic sphincter deficiency, the bladder neck opens during bladder filling without bladder contraction. Visible urinary leakage is seen with minimal or no stress. There is variable bladder neck and urethral descent, often none at all, and the leak point pressure is low (<60 cm $H_2O$). (J. G. Blaivas, 1985, *Urol. Clin. N. Amer.*, 12:215-224; D. R. Staskin et al., 1985, *Urol. Clin. N. Amer.*, 12:271-278).

Urge incontinence is defined as the involuntary loss of urine associated with an abrupt and strong desire to void. Although involuntary bladder contractions can be associated with neurologic disorders, they can also occur in individuals who appear to be neurologically normal (P. Abrams et al., 1987, *Neurol. & Urodynam.*, 7:403-427). Common neurologic disorders associated with urge incontinence are stroke, diabetes, and multiple sclerosis (E. J. McGuire et al, 1981, *J. Urol.*, 126:205-209). Urge incontinence is caused by involuntary detrusor contractions that can also be due to bladder inflammation and impaired detrusor contractility where the bladder does not empty completely.

Overflow incontinence is characterized by the loss of urine associated with overdistension of the bladder. Overflow incontinence may be due to impaired bladder contractility or to bladder outlet obstruction leading to overdistension and overflow. The bladder may be underactive secondarily to neurologic conditions such as diabetes or spinal cord injury, or following radical pelvic surgery.

Another common and serious cause of urinary incontinence (urge and overflow type) is impaired bladder contractility. This is an increasingly common condition in the geriatric population and in patients with neurological diseases, especially diabetes mellitus (N. M. Resnick et al., 1989, *New Engl. J. Med.*, 320:1-7; M. B. Chancellor and J. G. Blaivas, 1996, *Atlas of Urodynamics*, Williams and Wilkins, Philadelphia, Pa.). With inadequate contractility, the bladder cannot empty its content of urine; this causes not only incontinence, but also urinary tract infection and renal insufficiency. Presently, clinicians are very limited in their ability to treat impaired detrusor contractility. There are no effective medications to improve detrusor contractility. Although urecholine can slightly increase intravesical pressure, it has not been shown in controlled studies to aid effective bladder emptying (A. Wein et al., 1980, *J. Urol.*, 123:302). The most common treatment is to circumvent the problem with intermittent or indwelling catheterization.

There are a number of treatment modalities for stress urinary incontinence. The most commonly practiced current treatments for stress incontinence include the following: absorbent products; indwelling catheterization; pessary, i.e., vaginal ring placed to support the bladder neck; and medication (Agency for Health Care Policy and Research. Public Health Service: Urinary Incontinence Guideline Panel. Urinary Incontinence in Adults: Clinical Practice Guideline. AHCPR Pub. No. 92-0038. Rockville, Md. U.S. Department of Health and Human Services, March 1992; M. B. Chancellor, Evaluation and Outcome. In: The Health of Women With Physical Disabilities: Setting a Research Agenda for the 90's. Eds. Krotoski D. M., Nosek, M., Turk, M., Brooks Publishing Company, Baltimore, Md., Chapter 24, 309-332, 1996). With specific regard to medication, there are several drugs approved for the treatment of urge incontinence. However, there are no drugs approved or effective for stress urinary incontinence.

Exercise is another treatment modality for stress urinary incontinence. For example, Kegel exercise is a common and popular method to treat stress incontinence. The exercise can help half of the people who can do it four times daily for 3-6 months. Although 50% of patients report some improvement with Kegel exercise, the cure rate for incontinence following Kegel exercise is only 5 percent. In addition, most patients stop the exercise and drop out from the protocol because of the very long time and daily discipline required.

Another treatment method for urinary incontinence is the urethral plug. This is a new, inexpensive disposable cork-like plug for women with stress incontinence. A new plug should be used after each micturition, with an estimated daily cost of about $15-20. The estimated annual disposable cost is over $5,000. The plug is associated with over 20% urinary tract infection and, unfortunately, does not cure incontinence.

Biofeedback and functional electrical stimulation using a vaginal probe are also used to treat urge and stress urinary incontinence. However, these methods are time-consuming and expensive and the results are only moderately better than Kegel exercise. Surgeries, such as laparoscopic or open abdominal bladder neck suspensions; transvaginal approach abdominal bladder neck suspensions; artificial urinary sphincter (expensive complex surgical procedure with 40% reversion rate) are also used to treat stress urinary incontinence.

Other treatments include urethra injection procedures with exogenous injectable materials such as Teflon, collagen, and autologous fat. Each of these injectables has its disadvantages. More specifically, there are significant reservations among those in the medical community concerning the use of Teflon. Complications of Teflon injection include granuloma, diverticulum, cysts, and urethral polyp formation. Of greatest concern is the migration (via the lymphatic and vascular systems) of Teflon particles to distant locations, resulting in fever and pneumonitis.

Collagen injections generally employ bovine collagen, which is expensive and is often reabsorbed, resulting in the need for repeated injections. A further disadvantage of collagen is that about 5% of patients are allergic to bovine source collagen and develop antibodies.

Autologous fat grafting as an injectable bulking agent has a significant drawback in that most of the injected fat is resorbed. In addition, the extent and duration of the survival of an autologous fat graft remains controversial. An inflammatory reaction generally occurs at the site of implant. Complications from fat grafting include fat resorption, nodules and tissue asymmetry.

In view of the above-mentioned limitations and complications of treating urinary incontinence and bladder contractility, new and effective modalities in this area are needed in the art. In accordance with the present invention, muscle cell injection therapy using uniquely engineered muscle-derived cells is provided as an improved and novel means for treating and curing various types of incontinence, particularly, stress urinary incontinence and for the enhancement of urinary continence. As but one advantage, muscle-derived cell injection can preferably be autologous, so that there will minimal or no allergic reactions, unlike the aforementioned use of collagen. Also, unlike collagen, myogenic cells such as blasts are not absorbed; thus, they can provide a better improvement and cure rate.

Myoblasts, the precursors of muscle fibers, are mononucleated muscle cells which differ in many ways from other types of cells. Myoblasts naturally fuse to form post-mitotic multinucleated myotubes which result in the long-term expression and delivery of bioactive proteins (T. A. Partridge and K. E. Davies, 1995, *Brit. Med. Bulletin*, 51:123-137; J. Dhawan et al., 1992, *Science*, 254: 1509-1512; A. D. Grinnell, 1994, In: *Myology*. Ed 2, Ed. Engel AG and Armstrong CF, McGraw-Hill, Inc, 303-304; S. Jiao and J. A. Wolff, 1992, *Brain Research*, 575:143-147; H. Vandenburgh, 1996, *Human Gene Therapy*, 7:2195-2200). Myoblasts have been used for gene delivery to muscle for muscle-related diseases, such as Duchenne muscular dystrophy (E. Gussoni et al., 1992, *Nature*, 356:435-438; J. Huard et al., 1992, *Muscle & Nerve*, 15:550-560; G. Karpati et al., 1993, *Ann. Neurol.*, 34:8-17; J. P. Tremblay et al., 1993, *Cell Transplantation*, 2:99-112), as well as for non-muscle-related diseases, e.g., gene delivery of human adenosine deaminase for the adenosine deaminase deficiency syndrome (C. M. Lynch et al., 1992, *Proc. Natl. Acad. Sci. USA*, 89:1138-1142); gene transfer of human pro-insulin for diabetes mellitus (G. D. Simonson et al., 1996, *Human Gene Therapy*, 7:71-78); gene transfer for expression of tyrosine hydroxylase for Parkinson's disease (S. Jiao et al., 1993, *Nature*, 362:450); transfer and expression of Factor IX for hemophilia B (Y. Dai et al., 1995, *Proc. Natl. Acad. Sci. USA*, 89:10892), delivery of human growth hormone for growth retardation (J. Dhawan et al., 1992, *Science*, 254: 1509-1512).

The use of myoblasts to treat muscle degeneration, to repair tissue damage or treat disease is disclosed in U.S. Pat. Nos. 5,130,141 and 5,538,722. Also, myoblast transplantation has been employed for the repair of myocardial dysfunction (S. W. Robinson et al., 1995, *Cell Transplantation*, 5:77-91; C. E. Murry et al., 1996, *J. Clin. Invest.*, 98:2512-2523; S. Gojo et al., 1996, *Cell Transplantation*, 5:581-584; A. Zibaitis et al., 1994, *Transplantation Proceedings*, 26:3294).

Nitric oxide (NO) has been recognized as a important transmitter in genitourinary tract function. NO mediates smooth muscle relaxation and is also the key to achieving erection. Recently, constitutive and inducible nitric oxide synthase (NOS or iNOS) have been demonstrated in the urothelium, bladder and urethra wall. A deficiency in urinary NO in patients having interstitial cystitis bladder inflammation (M. A. Wheeler et al., 1997, *J. Urol.*, 158(6):2045-2050; S. D. Smith et al., 1997, *J. Urol.*, 158(3 Pt 1):703-708). Moreover, patients with interstitial cystitis had improvement in urinary symptoms and increased urinary NO production when treated with oral L-Arginine (M. A. Wheeler et al., 1997, *J. Urol.*, 158(6):2045-2050). Recent evidence has shown that urethral smooth muscle relaxation is mediated by NO release and that NO also mediates prostate smooth muscle relaxation (H. Kakizaki et al., 1997, *Am. J. Phys.*, 272:R1647-1656; A. L. Burnett, 1995, *Urology*, 45:1071-1083; M. Takeda et al., 1995, *Urology*, 45:440-446; W. Bloch et al., 1997, *Prostate*, 33:1-8).

SUMMARY OF THE INVENTION

It is an object of the present invention to provide new and effective methods and compositions for the treatment of various types of disease conditions and defects of the musculoskeletal system and the bone, using genetically engineered muscle-derived cells, e.g., myoblasts and muscle-derived stem cells, (also referred to as MDCs herein) in the cell-mediated delivery of exogenous genes for the expression and production of encoded gene products. The present invention affords a stable gene delivery vehicle to afflicted areas, e.g., the joint (ligament, meniscus, and cartilage), smooth muscle, skeletal muscle and bone, which sustains the production of proteins that ameliorate pathological muscle-related conditions, e.g., musculoskeletal and bone conditions. Examples of pathological conditions of the musculoskeletal system include arthritis and damage to ligaments, cartilage and meniscus, resulting in general muscle weakness and/or dysfunction, such as in the face and hands, as a nonlimiting example. Disease conditions of the bone include segmental bone fractures, defects, weakness, non-unions and any type of bone augmentation. The present invention overcomes the problem of transient gene expression, which reduces the efficacy of ex vivo gene transfer to the joint, for example, using synovial cells.

Another object of the present invention is to provide a general method for muscle-derived cell mediated ex vivo gene transfer involving harvesting muscle-derived cells, preferably, autologous muscle-derived cells, culturing the cells, transducing the cultured cells with an appropriate vector in vitro, e.g., a viral vector, harboring at least one exogenous gene encoding a bioactive molecule, such as a protein, polypeptide, peptide, drug, enzyme, metabolite, hormone and the like, and injecting the transduced muscle-derived cells into or near an affected area or site of injury, for example, a muscle; a joint, preferably, the knee joint; a bone defect; or a genitourinary tract defect.

According to the present invention, the method further includes enhancing and/or ameliorating the therapeutic and repair effects of the expressed bioactive molecule using muscle-derived cell mediated gene transfer to co-deliver gene(s) coding for trophic factors, e.g., growth factors, or auxiliary proteins and the like, which are also functionally expressed to further promote and ameliorate treatment and repair of the affected tissue. Suitable muscle-derived cells for use are myoblasts.

Also in accordance with the invention, the candidate molecules to be delivered with the muscle based gene therapy and tissue engineering include bone morphogenetic protein (BMP)-2, (BMP-2), and other subtypes of BMP (e.g. BMP-6 and BMP-12), vascular endothelial growth factor (VEGF), cartilage-derived morphogenetic proteins 1, 2 (CDMP-1, 2) and hedgehog, for the improvement of bone and cartilage healing. Insulin like growth factor-1 (IGF-1), nerve growth factor and basic fibroblast growth factor (bFGF) are used to improve muscle healing following injuries. In fact, according to the present invention, the use of these recombinant human growth factor proteins has been shown to improve muscle healing following laceration, contusion and strain injuries.

To improve the healing of meniscal injuries, epidermal growth factor (EGF), transforming growth factor α (TGF-α), basic fibroblast growth factor (bFGF) and platelet derived growth factor A,B (PDGF-A,B) are useful, since these growth factors are capable of improving meniscal fibrochondrocyte proliferation and increasing the synthesis of collagen and non-collagen proteins.

Finally, the growth factors particularly suited to improve ligament healing include platelet derived growth factor (PDGF), transforming growth factor-β (TGF-β), and epidermal growth factor (EGF), which are capable of improving the proliferative capacity of ligament fibroblast and therefore are important candidates to improve ligament healing.

It is another object of the present invention to provide new and effective methods and compositions for the treatment of various types of urinary incontinence, particularly stress urinary incontinence, using genetically engineered muscle-derived cells in the cell-mediated delivery of exogenous genes and their encoded gene products to tissues of the urinary system, such as the urethra and bladder.

It is yet another object of the present invention to provide uniquely engineered muscle-derived cells for carrying genes encoding products for treating a number of genetic and pathologic conditions of the musculoskeletal system and for treating and curing various types of incontinence, as well as for the further enhancement of urinary continence. Suitable muscle-derived cells include myoblasts and muscle-derived stem cells that will eventually differentiate into myotubes and muscle fibers, as well as into other lineages such as osteoblasts, chondrocytes, and smooth muscle cells, in particular, when muscle-derived stem cells are used.

Another object of the present invention is to inject autologous muscle-derived cells (e.g., myoblasts, and muscle-derived stem cells (MDCs)) that have been transfected or transduced with a vector (e.g., viral and non-viral) containing at least one gene encoding a bioactive molecule and, optionally, at least one gene encoding a trophic factor, e.g., a growth factor or a neurotropic factor, into a muscle tissue, e.g., the urethral wall as an effective treatment for stress urinary incontinence. The muscle-derived cells can be cultured and harvested and can generate sufficient quantities of muscle cells for repeated injections. The present invention is intended to embrace muscle-derived cells which have been genetically engineered to contain genes encoding both a bioactive molecule and a trophic factor. Alternatively, different muscle-derived cells can be engineered to contain either a gene encoding a bioactive molecule or a gene encoding a trophic factor or an immune suppression agent. The different muscle-derived cells can be co-injected or injected at different times, or in combination with other transduced muscle-derived cells, depending upon the type of treatment and therapeutic enhancement desired.

In accordance with the present invention, muscle-derived cells expressing desired gene products comprise a beneficial cell-mediated gene therapy which allows the survival of injected cells and the persistence of gene products, including growth factors (e.g. bFGF, IGF-1, VEGF, PDGF A,B, BMP-2, CDMP, etc.) and neurotropic factors (e.g., nerve growth factor) to treat and improve urinary tract dysfunction over prolonged periods of time.

Yet another object of the present invention is to provide a simple treatment method for women and men with stress urinary incontinence by using autologous, transfected muscle-derived cells to enhance their urinary sphincters. Such muscle-derived cell-mediated gene therapy allows repair and improvement of the urinary sphincter. In accordance with the present invention the treatment comprises a simple needle aspiration to obtain muscle-derived cells, for example, and a brief follow-up treatment to inject cultured and prepared cells into the patient via an outpatient endoscopic procedure. Also according to the present invention, autologous muscle cell injections using myoblasts and muscle-derived stem cells (MDCs) harvested from and cultured for a specific stress incontinence patient can be employed as a nonallergenic agent to bulk up the urethral wall, thereby enhancing coaptation and improving the urinary sphincter muscle. In this aspect of the invention, simple autologous muscle cell transplantation is performed, preferably without an accompanying gene therapy.

Another object of the present invention is the use of genetically engineered muscle-derived cells and cell mediated gene delivery for injection into the detrusor muscle as a means of modulating bladder contractility. In accordance with the present invention, survival of the muscle-derived cells and the expression of foreign genes in such cells have been demonstrated after injection into the bladder wall. Muscle-derived cell mediated gene therapy provides a useful treatment for modulating detrusor contractility and for an overactive bladder.

Another object of the present invention is to provide genetically engineered muscle-derived cells (e.g., myoblasts and muscle-derived stem cells) carrying the nitric oxide synthase (NOS) gene, preferably, inducible NOS (iNOS), for expression of nitric oxide synthase as a therapy for genitourinary tract dysfunction, for example, male erectile dysfunction, bladder inflammation, or stress incontinence. In accordance with the present invention, muscle-derived cells carrying the iNOS gene have been demonstrated to successfully deliver the inducible form of NOS (iNOS) into the penis and genitourinary tissue. Moreover, the production of iNOS, which produces higher quantities of nitric oxide than is produced by constitutive NOS, by the genetically engineered muscle-derived cells stimulated the release of NO and provided a significant increase in intracavernosal pressure, which was mediated by NO-induced penile vasodilation.

Further objects and advantages afforded by the present invention will be apparent from the detailed description and exemplification hereinbelow.

DESCRIPTION OF THE DRAWINGS

The appended drawings of the figures are presented to further describe the invention and to assist in its understanding through clarification of its various aspects.

FIGS. 1A-1C represent bladder neck myoblast injection. FIGS. 1D-1F represent urethral myoblast injection. FIGS. 1G-1I represent urethral myoblast injection using a double staining technique in which both lacZ staining (blue) and fluorescent latex microsphere labeling (fluorescent green) can be visualized. Many regenerative myofibers expressing β-galactosidase are seen in the urethral and bladder neck wall. There are large, disorganized patterns of myofibers intermingled with fluorescent latex microspheres. Hematoxylin-eosin (H and E) tissue staining was used.

FIGS. 5A and 5B show the expression of LacZ in the meniscus following injection and expression of β-galactosidase. FIG. 5C shows that LacZ staining is co-localized with fluorescent latex microspheres in the injected area. FIG. 5D shows the expression of desmin, a myogenic marker (green fluorescence) showing the presence of muscle cells in the meniscus.

FIGS. 6A-6D show the results of myoblast-mediated ex vivo gene transfer into rabbit ligament. Myoblasts transduced with an adenovirus vector carrying the gene encoding β-galactosidase (LacZ) were injected into rabbit ligament. FIGS. 6A and 6B show the expression of LacZ in the ligament following injection and expression of β-galactosidase. FIG. 6C shows that LacZ staining is co-localized with fluorescent latex microspheres in the injected area. FIG. 6D shows the expression of desmin, a myogenic marker (green fluorescence) showing the presence of muscle cells in the ligament.

FIGS. 8A-8D shows the ability of engineered myoblasts expressing anti-inflammatory substance IRAP to circumvent the poor survival of the injected cells. The survival of the myoblasts engineered to express interleukin-1 receptor antagonist protein (IL-1Ra) (FIG. 8B) was compared with the non-engineered control cells (FIG. 8A). The non-engineered cells were rapidly lost by 48 hours post-injection (Control myoblast). In contrast, the cells engineered to express IL-1Ra significantly reduced the early loss of the injected cells (IL-1Ra expressing myoblast): only 20% of the injected cells were lost at 48 hours post-injection. However, a significant reduction in the amount of β-galactosidase expression was observed at 24 hours post-injection compared with the non-injected myoblasts. A high number of transduced myofibers persisted between day 2 and day 5 following injection (FIGS. 8C, 8D). The absence of a significant difference for both populations of cells at 0 and 0.5 hours post-injection suggested that the loss of myoblasts was minimal during injection. "*" indicates a significant difference (P<0.05) compared with transduced non-injected myoblasts (0 hour).

FIGS. 14A and 14B show the expression of desmin, a myogenic marker (green fluorescence), which reveals the presence of muscle cells in the cartilage. FIG. 14C shows the expression of β-galactosidase in the injected cartilage with myoblasts transduced with adenovirus carrying the expression of β-galactosidase.

FIG. 15A shows the six-month persistence post-injection without damage to the bladder wall. FIG. 15B shows the assays for β-galactosidase in the injected bladder is maintained approximately 66% after 70 days. FIG. 15C shows the cross section of a rat urethra. Injection of primary rat muscle-derived cells resulted in a large bulking effect in the urethra wall.

DETAILED DESCRIPTION OF THE INVENTION

Figure 1G:
FIGS. 1A-1I present light and fluorescence microscopic analyses of urethral and neck tissue demonstrating the persistence of injected myoblasts carrying the β-galactosidase gene and producing β-galactosidase, i.e., lacZ, (blue spots) and fluorescent latex microspheres (fluorescent green). Increasing magnification (from 40× to 100×) of the same specimen is shown, with FIGS. 1A, 1D, and 1G having the lowest magnification and FIGS. 1C, 1F, and 1I having the highest magnification.
Figure 1H:
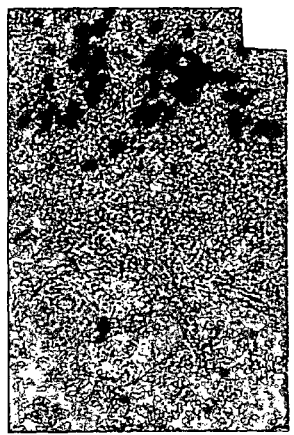
Figure 1I:
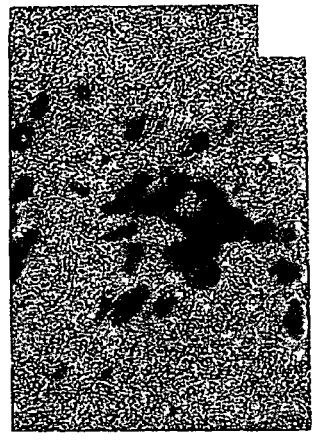
Figure 1D:
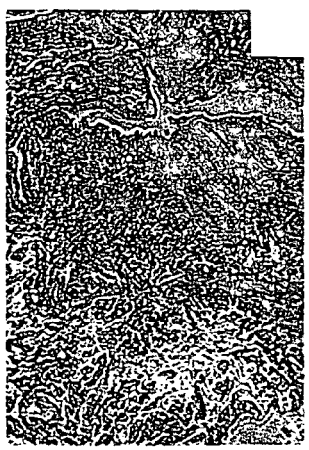
Figure 1E:
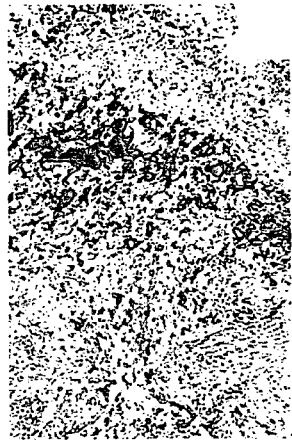
Figure 1F:
Figure 1A:
Figure 1B:
Figure 1C:

The present invention provides genetically engineered muscle-derived cells containing at least one heterologous nucleic acid (i.e., exogenous to the muscle cells) encoding a desired gene product, such as a protein, polypeptide, peptide, hormone, metabolite, enzyme, or a trophic factor, including cytokines, in which the gene product(s) is/are expressed in a sustained fashion in the cells, and are delivered therapeutically by the engineered cells to a tissue or organ site to promote healing after injury, or to remedy a localized organ or tissue dysfunction. Tissues and organs suitable for muscle-derived cell-mediated gene delivery according to the present invention include the musculoskeletal system (e.g., joint), bone, and urogenital system (e.g., urethra, bladder, sphincter).

More particularly, the present invention provides such genetically engineered muscle-derived cells (MDCs), e.g., myoblasts, to improve and expand the treatment of several types of bladder dysfunction including impaired bladder contractility. Also, the present invention provides for the first time the use of skeletal muscle cells for the repair of urinary tract smooth muscle dysfunction.

The present invention further provides a revolutionary new treatment for urinary incontinence caused by urethral and bladder impairment or dysfunction. Men and women afflicted with stress incontinence are treated by using autologous muscle-derived cell injection (i.e., such as myoblasts, harvested from the patient) to build up and support the urinary sphincter. The present invention relates to muscle-derived cells injected into the bladder wall as a cellular myoplasty technique to improve detrusor contractility and relates to muscle-derived cell-mediated expression of nitric oxide synthase (NOS) as gene therapy for the treatment of lower urinary tract dysfunction.

A number of muscle-derived or myogenic cells are suitable for use in the present invention. Nonlimiting examples of such cells include myoblasts, fibroblasts, adipocytes and muscle-derived stem cells which reside in muscle tissue. Also intended for use in the present invention are skeletal myoblasts from skeletal muscle, particularly for use in the repair of smooth muscle dysfunction in the urinary tract. In the practice of the present invention, muscle-derived cells are capable of delivering genes not only to skeletal and smooth muscle, but also to bone, cartilage, ligaments and meniscus.

In accordance with the present invention, muscle-derived cells, including myoblasts, may be primary cells, cultured cells, or cloned. They may be histocompatible (autologous) or nonhistocompatible (allogeneic) to the recipient, including humans. Such cells are genetically engineered to carry specific genes encoding particular gene products and/or drug products, and can serve as long-term local delivery systems for a variety of treatments, for example, for the treatment of such diseases and pathologies as bladder cancer, transplant rejection, neurogenic bladder conditions, e.g., those secondary to diabetes mellitus, and for the regeneration of muscle and nerve.

Preferred in the present invention are myoblasts and muscle-derived stem cells, and more preferred are autologous myoblasts and muscle-derived stem cells which will not be recognized as foreign to the recipient. In this regard, the myoblasts used for cell-mediated gene transfer or delivery will desirably be matched vis-á-vis the major histocompatibility locus (MHC or HLA in humans). Such MHC or HLA matched cells may be autologous. Alternatively, the cells may be from a person having the same or a similar MHC or HLA antigen profile. The patient may also be tolerized to the allogeneic MHC antigens. The present invention also encompasses the use of cells lacking MHC Class I and/or II antigens, such as described in U.S. Pat. No. 5,538,722.

Myoblasts, the mononucleated muscle cells, are uniquely different from other cells in the body in a number of ways: 1) myoblasts naturally differentiate to form muscle tubules capable of muscle contraction, 2) when myoblasts fuse to form myotubes, these cells become post mitotic (stop dividing) with maturation, thus allowing control of the number and amount of myoblasts per injection, and 3) as myotubes, the cells express large amounts of protein which is produced in the cells due to multinucleation.

In accordance with the present invention, muscle-derived cells, including myoblasts, may be genetically engineered by a variety of molecular techniques and methods known to those having skill in the art, for example, transfection, infection, or transduction. Transduction as used herein refers to cells which have been genetically engineered to contain a foreign or heterologous gene via the introduction of a viral vector into the cells. Muscle-derived cells, including myoblasts, can be transduced by different viral vectors and thus can serve as gene delivery vehicles to transfer expressed proteins into muscle.

Although viral vectors are preferred, those having skill in the art will appreciate that the genetic engineering of cells to contain nucleic acid sequences encoding desired proteins or polypeptides, cytokines, and the like, may be carried out by methods known in the art, for example, as described in U.S. Pat. No. 5,538,722, including fusion, transfection, lipofection mediated by the use of liposomes, electroporation, precipitation with DEAE-Dextran or calcium phosphate, particle bombardment (biolistics) with nucleic acid-coated particles (e.g., gold particles), microinjection, and the like.

The present invention also relates to vehicles or vector constructs for introducing heterologous (i.e., foreign) nucleic acid (DNA or RNA), or a segment of nucleic acid that encodes a functional bioactive product, into muscle-derived cells, in which the vectors comprise a nucleic acid sequence read in the correct phase for expression. Such vectors or vehicles will, of course, possess a promoter sequence, advantageously placed upstream of the sequence to be expressed. The vectors may also contain, optionally, one or more expressible marker genes for expression as an indication of successful transfection and expression of the nucleic acid sequences contained in the vector. To insure expression, the vectors contain a promoter sequence for binding of the appropriate cellular RNA polymerase, which will depend on the cell into which the vector has been introduced. For example, the promoter for expression in muscle-derived cells, such as myoblasts, is a promoter sequence to which the cellular RNA polymerases will bind.

Illustrative examples of vehicles or vector constructs for transfection or infection of muscle-derived cells include replication-defective viral vectors, DNA virus or RNA virus (retrovirus) vectors, such as adenovirus, herpes simplex virus and adeno-associated viral vectors. Adeno-associated virus vectors are single stranded and allow the efficient delivery of multiple copies of nucleic acid to the cell's nucleus. Preferred are adenovirus vectors. The vectors will normally be substantially free of any prokaryotic DNA and may comprise a number of different functional nucleic acid sequences. An example of such functional sequences may be a DNA region comprising transcriptional and translational initiation and termination regulatory sequences, including promoters (e.g., strong promoters, inducible promoters, and the like) and enhancers which are active in muscle cells. Also included as part of the functional sequences is an open reading frame encoding a protein of interest, and may also comprise flanking sequences for site-directed integration. As a particular example, in some situations, the 5'-flanking sequence will allow homologous recombination, thus changing the nature of the transcriptional initiation region, so as to provide for inducible or noninducible transcription to increase or decrease the level of transcription, as an example.

In general, the nucleic acid desired to be expressed by the muscle-derived cell is that of a structural gene, or a functional fragment, segment or portion of the gene, that is heterologous to the muscle-derived cell and encodes a desired protein or polypeptide product, for example. The encoded and expressed product may be intracellular, i.e., retained in the cytoplasm, nucleus, or an organelle of a cell, or may be secreted by the cell. For secretion, the natural signal sequence present in the structural gene may be retained, or a signal sequence that is not naturally present in the structural gene may be used. When the polypeptide or peptide is a fragment of a protein that is larger, a signal sequence may be provided so that, upon secretion and processing at the processing site, the desired protein will have the natural sequence. More specific examples of genes of interest for use in accordance with the present invention include the genes encoding nitric oxide synthase; trophic factors, including growth factors and cytokines, such as basic and acidic fibroblast growth factors (bFGF and aFGF), nerve growth factor (NGF), brain derived neurotrophic factor (BDNF), neurotrophin, insulin-like growth factor (IGF), transforming growth factor alpha (TGF-α), transforming growth factor beta (TGF-β), platelet derived growth factor (PDGF) and the like; hormones; metabolic products, generally of low molecular weight; diffusable products; serum proteins; osteogenic proteins, e.g., BMP-2.

As mentioned above, a marker may be present for selection of cells containing the vector construct. The marker may be an inducible or non-inducible gene and will generally allow for positive selection under induction, or without induction, respectively. Examples of marker genes include neomycin, dyhydrofolate reductase, LacZ, and the like.

The vector employed will generally also include an origin of replication and other genes that are necessary for replication in the host cells, as routinely employed by those having skill in the art. As an example, the replication system comprising the origin of replication and any proteins associated with replication encoded by a particular virus may be included as part of the construct. As a caveat, the replication system must be selected so that the genes encoding products necessary for replication do not ultimately transform the muscle-derived cells. Such replication systems are represented by replication-defective adenovirus constructed as described by G. Acsadi et al., 1994, *Human Mol. Genetics*, 3(4):579-584, and by Epstein-Barr virus. Examples of replication defective vectors, particularly, retroviral vectors that are replication defective, are BAG, described by Price et al., 1987, *Proc. Natl. Acad. Sci.*, 84:156; and Sanes et al., 1986, *EMBO J.*, 5:3133. It will be understood that the final gene construct may contain one or more genes of interest, for example, a gene encoding a bioactive metabolic molecule, e.g., NOS, iNOS, or NO, and a gene encoding a cytokine, e.g., bFGF, along with the sequences allowing for the proper expression and production of the gene products by the engineered cells. In addition, cDNA, synthetically produced DNA or chromosomal DNA may be employed utilizing methods and protocols known and practiced by those having skill in the art.

If desired, infectious replication-defective viral vectors may be used to genetically engineer the cells prior to in vivo injection of the cells. In this regard, the vectors may be introduced into retroviral producer cells for amphotrophic packaging. The natural expansion of muscle-derived cells, such as myoblasts, into adjacent regions obviates a large number of injections into the muscle fibers at the site(s) of interest.

In one embodiment of the present invention muscle-derived cells are transduced with nucleic acid encoding a particular gene product, e.g., a gene encoding inducible nitric oxide synthase (iNOS). The transduced muscle-derived cells, which contain, express and produce the iNOS product, are used in cell-mediated transplantation or gene therapy techniques for the treatment of genitourinary tract dysfunction. Examples of lower urinary tract dysfunction include, but are not limited to, erectile dysfunction of the penis, pyronies disease of the penis; dysfunctions of the urethra, such as stress urinary incontinence, bladder outlet obstruction, urethritis, dysfunction voider; bladder dysfunctions, such as impaired bladder contractility, neurogenic bladder, cystitis and bladder inflammatory disease; and dysfunction of the female sexual and reproductive organs, such as vagina, cervix, uterus, fallopian tubes and ovaries.

The same or different muscle-derived cells may also be co-transduced with heterologous nucleic acid encoding trophic factors whose expression in and production by the muscle-derived cells aid in effecting and/or enhancing the therapeutic uses of the transduced muscle-derived cells in cell-mediated gene therapy. Trophic factors such as cytokines are preferably used. More specifically, useful cytokines include those presented hereinabove, among which are basic fibroblast growth factor (bFGF), nerve growth factor (NGF) and interleukins, such as IL-1 and IL-6.

Muscle-derived cells engineered to contain nucleic acid encoding one or more trophic factors can be administered as a treatment at the same time as muscle-derived cells containing nucleic acid encoding a therapeutic protein or a bioactive molecule, such as a protein, polypeptide, peptide, hormone, metabolite, drug, enzyme, and the like. Alternatively, muscle-derived cells engineered to express trophic factors may be administered at a later or earlier time, depending on the type of treatment desired.

In general, an injection of genetically engineered muscle-derived cells, including myoblasts and muscle-derived stem cells, into a given tissue or site of injury comprises a therapeutically effective amount of cells in solution or suspension, preferably, about $10^5$ to $10^6$ cells per $cm^3$ of tissue to be treated, in a physiologically acceptable medium, such as saline or phosphate buffered saline, and the like.

In a preferred aspect, the present invention provides ex vivo gene delivery to cells and tissues of a recipient mammalian host, including humans, through the use of muscle-derived cells, e.g., myoblasts, that have been virally transduced using an adenoviral vector engineered to contain a heterologous gene encoding a desired gene product. Such an ex vivo approach provides the advantage of efficient viral gene transfer which, in cases of treatment of muscle-related dysfunction and defects as described herein, is superior to direct gene transfer approaches. The ex vivo procedure involves the establishment of a primary muscle-derived cell culture from isolated cells of muscle tissue. The muscle biopsy that will serve as the source of muscle-derived cells can be obtained from the injury site or from another area that may be more easily obtainable from the clinical surgeon.

The muscle-derived cells are first infected with engineered viral vectors containing at least one heterologous gene encoding a desired gene product, and then are injected into the same host. In the case of myoblasts as an example, the injected, transduced, isogenic muscle-derived cells then fuse to form myotubes at and near the site of injection. The desired gene product is expressed by the injected cells which thus introduce the gene product into the injected tissue, e.g., muscle. The introduced gene products can promote and enhance muscle regeneration and muscle strength in vivo to ameliorate muscle healing following injuries.

In a particular embodiment of the present invention, muscle-derived cell injection, preferably autologous myoblast injection, into the urethral wall is employed as a treatment for stress urinary incontinence to enhance, improve, and/or repair the urinary sphincter. Muscle-derived cells, preferably myoblasts, carrying one or more transduced or transfected heterologous nucleic acids encoding a bioactive molecule and/or a trophic factor, are injected into the urethral wall and survive and differentiate into myofibers to improve sphincter function. The feasibility and survival of myoblast injection into the urethral wall is demonstrated in Example 2. In accordance with this embodiment, autologous muscle-derived cell injections (i.e., muscle-derived cells harvested from and cultured for a specific stress incontinence patient) can be used as a nonallergenic agent to bulk up the urethral wall, thereby enhancing coaptation and improving the urinary sphincter muscle.

In another embodiment of the present invention, muscle-derived cells are injected into the bladder wall to improve detrusor contractility. Muscle-derived cells, such as myoblasts and muscle-derived stem cells, injected into the bladder wall are capable of surviving and differentiating into myofibers that can augment detrusor contractility as demonstrated in Example 3. In addition, muscle-derived cells which have been genetically engineered to carry a foreign gene express the foreign gene product after injection into the bladder wall.

In accordance with the present invention, autologous muscle-derived cells administered directly into the bladder and urethra exhibit long-term survival. The use of cell-mediated gene therapy involving genetically engineered muscle-derived cells is advantageous over the use of other forms of gene therapy, i.e., gene therapies involving the direct administration of virus or plasmid vectors, for example. As an example, the type of muscle-derived cell may contribute to the survival of the injected cells post-transplantation. In this regard, autologous primary myoblasts can be harvested and cultured myoblasts can be stored and used in sufficient quantities for repeated urethral and bladder injections. Autologous myoblast injection results in safe and nonimmunogenic long-term survival of myofibers in the lower urinary tract. (see Example 4 and FIGS. 15A-15C).

In a particular embodiment, muscle-derived cell mediated gene therapy of the present invention further involves muscle-derived cells, e.g., myoblasts, transduced with an adenovirus vector carrying the bFGF gene, thereby allowing expression of bFGF by the transduced muscle-derived cells in a given tissue. bFGF engineered muscle-derived cells are injected into the urethra to treat stress incontinence and also into the bladder wall to improve detrusor contractility. In accordance with the present invention, injection of bFGF engineered muscle-derived cells allows improvement in survival and function versus non-engineered muscle-derived cells. Following short-term experiments, long-term experiments were conducted using autologous primary myoblast-bFGF injection into the bladder and urethra at 4, 14, and 30 days, as described in Example 6. Cell mediated gene therapy using transduced myoblasts which secreted the trophic factor bFGF provided further improved success in overcoming dysfunctions in the urethra and bladder compared with non-bFGF-secreting myoblasts.

In another preferred embodiment, adenoviral vectors carrying the inducible nitric oxide synthase (iNOS) gene are introduced into muscle-derived cells and the resulting transduced cells are used in cell-mediated gene therapy. When such transduced muscle-derived cells are administered locally to the urethra and bladder, dramatic functional modifications are demonstrated, e.g., decrease in bladder inflammation and improvement in urethral relaxation (see Example 7). In this aspect of the present invention, iNOS engineered muscle-derived cell-mediated gene therapy in the bladder provided a diminution of bladder inflammation. In addition, iNOS engineered myoblast injection into the urethra was demonstrated to be useful to decrease urethral outlet obstruction. According to the present invention, myoblast mediated iNOS gene therapy resulted in increased local NO production in injected tissue. iNOS gene therapy in the bladder also decreased the cyclophosphamide (CYP)-induced bladder inflammatory response. iNOS gene therapy into the urethra further induced sustained urethral smooth muscle relaxation as described in Example 7.

In another embodiment of the present invention, the use of muscle-derived cell-mediated gene transfer to the musculoskeletal system, such as the joint, offers numerous advantages. A muscle biopsy for the isolation of muscle-derived cells, e.g., myoblasts, for use as gene delivery vehicles in accordance with the present invention is much easier and less invasive than, for example, surgical synovial capsule biopsy for the isolation of synovial cells. In a muscle biopsy, a small area of muscle tissue generally contains enough myogenic cells to produce quickly millions of muscle-derived cells in culture. For myoblasts, once the cells are isolated and grown in culture, it is easy to distinguish pure myoblasts from other cell types, since myoblasts fuse to form elongated myotubes in vitro. In addition, desmin, a myogenic specific marker protein, can be used to determine the myogenicity index of the cell culture without the requirement of differentiation. In contrast, because synovial cells are more difficult to distinguish from other cell types, obtaining a pure synovial cell culture is problematic for the treatment of muscle disease or dysfunction.

In addition, before fusion, myoblasts are over five times more efficiently transduced than synovial cells using the same number of adenoviral particles per cell in vitro. The differentiation of transduced myoblasts into myotubes increases the level of gene expression in the differentiated myotubes and myofibers. One of the major advantages of myoblasts over other cell types, such as synovial cells, is the myoblast's ability to fuse and become a differentiated post-mitotic cell, which can persistently express a high level of an exogenous gene product. In fact, myoblast mediated gene expression has persisted for at least 35 days in the joint. This allows for the persistent and efficient expression and production of any proteins of interest in the joint.

Figure 4:
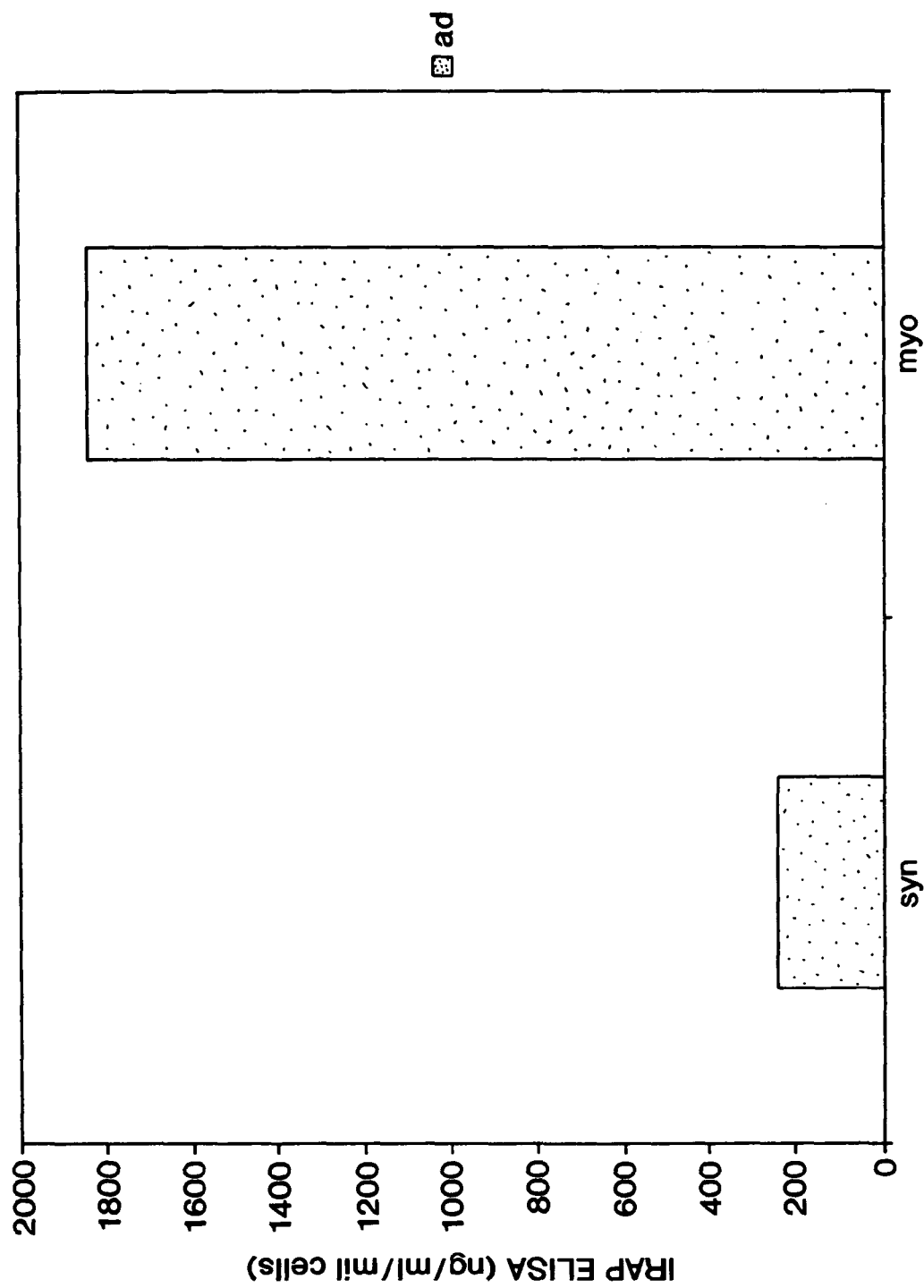
FIG. 4 shows interleukin-1 receptor agonist protein (IRAP) production (ng/ml/$10^6$ cells as measured by ELISA) after either synovial cells (syn) or myoblasts (myo) transduced with adenoviral vector carrying the gene encoding IRAP (ad-IRAP) were used to infect rabbit joint.

In addition, myoblasts transduced with adenoviral vectors carrying the gene encoding interleukin-1 receptor agonist protein (IRAP) produced nine times more IRAP as measured by ELISA than infection by similarly transduced synovial cells. The results indicate that myoblasts are introducing more protein following gene transfer into the knee joint synovial lining adjacent to the patella. (FIG. 4).

Moreover, myoblasts have been demonstrated to survive in newborn and adult articular joints (knee) of animal models. Such myoblasts have adhered to most of the structures of a newborn knee, including patellar ligaments, cruciate ligaments, meniscus, synovium and joint capsule. By contrast, synovial cells have survived in the knee by adhering only to the synovial lining.

In addition, injections of muscle-derived cells directly into the intra-articular structures, including ligament and meniscus, results in a higher gene transfer than that observed using injection into the joint fluid. By the practice of the present invention, it has been shown that myoblasts engineered with an adenovirus carrying the expression of the β-galactosidase reporter gene are capable of delivering a higher efficiency and a long term persistence of the reporter gene when compared to the use of ligament fibroblasts and direct adenoviral injection (FIGS. 6A-6D) Accordingly, adenovirally transduced myoblasts were able to deliver genes and express gene products in the ligament and meniscus of rabbit at 1 week post injection (FIGS. 5A-5D, meniscus and FIG. 6A-6D, ligament), thereby indicating that that the use of this technology can help to improve ligament healing following injuries. Thus, as described herein, injection directly into the intra-articular structures or into joint fluid can be used to deliver genes into the joint.

Stable and persistent gene delivery via muscle-derived cells in the joints has numerous clinical applications. Genetically engineered muscle-derived cells, such as myoblasts and muscle-derived stem cells, can deliver proteins with an anti-arthritic function, such as interleukin-1 receptor agonist protein (IL-1Ra) or soluble receptors for tumor necrosis factor-α (TNF-α) into an inflamed knee joint (Example 9). This technology can supplant surgical intervention to aid in the healing of different types of damaged tissues (e.g., ligament, meniscus, cartilage) which have poor intrinsic healing capacities in the joint. Also, growth factors can be delivered to the site and persist there in the practice of the present invention to ameliorate tissue pathologies in the joint. The high level of gene expression and gene product production by the muscle-cell mediated gene transfer technology provides advantages to the art that were previously unable to be attained using current methodologies.

In accordance with the present invention, muscle-derived stem cells can be isolated from skeletal muscle. When appropriately stimulated with bone morphogenetic protein-2 (BMP-2), these cells were capable of expressing alkaline phosphatase in a dose dependent manner and, more importantly, of actively participating in bone formation in vivo. These cells have the ability to differentiate into other lineages. Accordingly, these cells may be used not only to deliver growth factors and cytokines for the musculoskeletal system, but also to act as an endogenous source of responding cells that may actively participate in the healing process of the musculoskeletal system.

In another embodiment of the present invention, muscle-derived cell-mediated gene transfer is employed to treat bone defects (Example 10). Because most bone defects are surrounded by muscle, the injected muscle-derived cells, such as myoblasts, have a natural myogenic milieu to fuse onto. Muscle biopsies to isolate muscle-derived cells suitable for use according to the invention are less invasive procedures than are bone marrow biopsies to isolate stromal cells, for example. In fact, most muscle biopsies can be done in an office setting.

In addition, a large percentage of the cells isolated from a skeletal muscle biopsy are myoblasts, while only 1 to 2% of bone marrow cells have osteogenic capacity. Myoblasts in cell culture can be further purified using an established technology (T. A. Rando and H. M. Blau, 1994, *J. Cell. Biol.*, 125:1275-1287) and muscle cells are relatively easy to cultivate in vitro; millions of cells can be grown in a few days.

Another advantage of muscle-derived cell mediated gene therapy for the treatment of bone defects is that muscle cells can transform into osteoblasts when stimulated by osteogenic proteins, thereby affording them osteogenic potential after stimulation. For example, transduced myoblasts were capable of fusing into myofibers in the bone defect and in the muscles surrounding the defect while expressing a marker gene (Example 10). Thus, in accordance with the present invention, engineering the skeletal muscle cells surrounding the bone defect to express or overexpress osteogenic proteins, e.g., BMP-2, allows the release of these proteins to improve bone healing at the adjacent bone defect. More importantly, the transplantation of BMP-2 engineered muscle-derived cells, which can fuse to form myotubes and myofibers producing the osteogenic protein in the bone defect, can further enhance bone healing. In fact, muscle-derived cell mediated gene transfer of osteogenic proteins has the capability of improving both osteoinductive and osteoconductive aspects of bone healing.

The cyto-architecture of the fused myofibers may not only serve as a reservoir of secreting osteogenic proteins, but also as a matrix for bone formation. It is likely that muscle, due to its high vascularity, may improve the revascularization of the bone defect and, therefore, aid in the improvement of bone healing. In accordance with this embodiment, the present invention provides a viable and efficient approach to improving the healing of both segmental bone defects, bone fractures and non-unions, and provides cells which can participate in desired bone formation.

In a related aspect of the invention, the present inventors have determined that a population of osteoprogenitor cells residing within skeletal muscle are suitable as vehicles for the delivery of osteogenic proteins such as BMP-2 to the bone defect area. Further, under the stimulation of such osteogenic proteins, the delivery cells themselves have the potential to become osteoblasts and participate in bone formation (Example 11). Such muscle-derived pre-osteoblastic cells (i.e., pluripotent mesenchymal cells found in skeletal muscle) are superior to stromal cells as cell-mediated ex vivo gene delivery vehicles because of the increased protein capacity of the former cells.

As described in Example 11, a subpopulation of muscle-derived cells, obtainable by an easily reproducible technique, can be induced to acquire alkaline phosphatase activity (ALP) by stimulation with BMP-2. Without BMP-2 stimulation, that same population of cells does not have ALP activity. The ALP activity has a trend toward dose dependence and increases significantly with additional dosing with BMP-2 over time. The same cell population decreases its expression of desmin, a myogenic marker, with BMP-2 stimulation. The BMP-2 stimulatable, ALP-producing cell population is morphologically distinct from other muscle-derived cells and divide slowly. Such cells are likely to represent a population of pluripotent mesenchymal cells present in muscle and useful for cell mediated gene delivery to bone in accordance with the present invention.

EXAMPLES

The examples as set forth herein are meant to exemplify the various aspects of the present invention and are not intended to limit the invention in any way.

Example 1

Materials and Methods:

The materials and methods described in Example 1 pertain to the description of the invention and the other examples as set forth hereinbelow.

Animals and Myoblast Injection: Adult Sprague Dawley (S.D.) female rats (Hilltop Laboratories, Pittsburgh, Pa.), weighing approximately 250 g were used in the experiments described. Only certified viral free animals were used. The animals were housed in an approved viral gene therapy P-2 facility at the University of Pittsburgh Medical Center. Strict adherence to P-2 protocol was followed. The animals were anesthetized with pentobarbital (50 mg/kg) for myoblast harvesting, myoblast injection, and during measurement of bladder pressure.

After surgical preparation, a low midline incision was made to expose the bladder and proximal urethra. During injection using a Hamilton syringe, 10-20 microliter ($\mu$l) of myoblast suspension (approximately $1-2\times10^6$ cells per 10 $\mu$l) were injected into the bladder or dorsal proximal urethral submucosa of experimental animals (Group 1) in two sites. Identical sites were injected in each animal. Control animals (Group 2) were injected with an equal volume of sterile saline solution. During the first week after the implantation the animals were closely monitored for any adverse events.

Cryoinjury Model: An 8 mm diameter aluminum rod (Harvard Scientific) was used as a cryoprobe to cause a full thickness bladder or urethral wall injury without causing bladder rupture. The cryoprobe was placed in dry ice for 1 minute then immediately placed against the bladder wall or urethral wall for 10 seconds without causing bladder rupture as determined by histology. This method has been found to cause a reliable and reproducible transmural injury. In sham-treated animals, the cryoprobe was placed against the tissue at room temperature. For bladder injury, the bladder was filled to 1 ml volume using sterile saline through a urethral catheter. Each bladder was injured at one site (bladder dome). Myoblast injection was done 15 minutes after cryo or sham injury at the site of injury. Urethral injury was carried out at the ventral 12 o'clock position of the proximal urethra with the bladder neck as the cranial margin.

Micturition Pattern Measurement: Urination pattern profiles were obtained using a specialized metabolic cage which deflects voided urine for collection and quantification over a 24 hour period. Micturition parameters evaluated in the described experiments included total urine output/24 hours, number of micturitions/24 hours and mean volume per micturition (M. D. Chancellor et al., 1994, *J. Urol.*, 151:250-254; T. Watanabe et al., 1996, *J. Urol.*, 156:1507-1510).

The deflected urine was collected in a cup placed on a strain gauge transducer (Grass, F3) connected to a strain gauge preamplifier (Word Precision Instruments, Saratoga, Fla.). The data were input into a data acquisition system: data acquisition was carried out with an AD card (DATAQ) placed in a Gateway 2000 computer. Appropriate data acquisition software (i.e., DI-200, DATAQ) and a playback software (i.e., WindaqEx) were installed on the computer.

Cystometrogram (CMG): CMG (i.e., measurement of myoblast urethral injection; measurement of myoblast bladder injection and measurement of urethral pressure) was performed under urethane anesthesia (2.4 mg/kg$^2$). Specific techniques of CMG for urethral and bladder injection are described below.

Measurement of Myoblast Urethral Injection: The bladder was cannulated using a p-50 catheter placed through the puncture site in the bladder dome and secured with a silk ligature. This catheter was connected to a Y connector and to both a Harvard infusion pump and a Grass polygraph. Continuous infusion urodynamic evaluation was conducted with a constant fill rate of 0.075 ml/min. using a Harvard pump. The volume of bladder capacity, maximum voiding pressure and residual urine volume were determined.

Measurement of Myoblast Bladder Injection: The bladder was cannulated using a p-50 catheter placed per urethra. This catheter was connected to a Y connector and to both a Harvard infusion pump and a Grass polygraph. Continuous infusion urodynamic evaluation was conducted with a constant fill rate of 0.075 ml/min. using a Harvard pump. The volume of bladder capacity, maximum voiding pressure and residual urine volume were determined. The urethra was cannulated as described in the experiments, rather than the bladder as outlined in the measurement of myoblast urethral injection, so as not to alter bladder function.

Urethral Pressure Measurement: Urethral perfusion pressure and isovolumetric bladder pressure were measured with catheters inserted through the bladder dome in urethane anesthetized female S.D. rats. The previously described catheter assembly (H. Kakizaki et al., 1997, *Am. J. Physiol.*, 272: R1647-1656) was wedged in the bladder neck to block passage of fluid between the bladder and urethra without affecting the nerve supply to the organs. The external urethra was not catheterized. Responses were examined at an urethral saline infusion speed of 0.075 ml/min.

A double lumen transvesical intraurethral perfusion and pressure recording catheter was prepared as follows: A double lumen bladder catheter was constructed from PE 200 tubing (outer lumen, free end flame flared) and PE 50 tubing (inner lumen). The PE 200 tube was connected to a syringe for bladder filling and the PE 50 tube was connected to a pressure transducer. Both tubes can also be connected, by way of stopcocks, to a peristaltic pump system set up for isovolumetric fluid exchange as a method for intravesical drug delivery.

A double lumen urethral catheter was constructed from PE 160 tubing (outer lumen) and PE 50 tubing (inner lumen). The PE 160 tubing was fitted with a pipette tip at one end and was connected to an infusion pump for intraurethral perfusion of either saline or drug solution. The PE 50 tubing inner lumen extended slightly past the outer lumen, but remained within the pipette tip. The other end was connected to a pressure transducer for the measurement of intraurethral perfusion pressure.

The urethral catheter system was passed through the dome of the bladder and was seated snugly in the bladder neck. Both the bladder and urethral catheters were fixed in place at the bladder dome with suture.

Measurement of the Contraction of the Bladder and Urethral Strips Evoked by Electrical Stimulation: The bladder and urethra were quickly removed from the abdomen after decapitation. One longitudinal strip was prepared from each bladder and one spiral strip was prepared from the urethra. The preparations were mounted in 5 mL organ baths containing Krebs solution (mmol/L: NaCl 113, KCl 4.7, $CaCl_2$ 1.25, $MgSO_4$ 1.2, $NaHCO_3$ 25, $KH_2PO_4$ 1.2, glucose 11.5) and constantly bubbled with a mixture of 95% $O_2$ and 5% $CO_2$. The initial tension was set to 10 mN and isometric contractions were measured with strain-gauge transducers coupled with a TBM4 strain gauge amplifier (World Precision Instruments) and recorded on computer using a data acquisition program (Windaq, DATAQ Instruments Inc, Akron, Ohio, USA). The sampling rate per channel was set to 100 Hz. The amplitude of the stimulation-evoked contractions was computed by a calculation program (WindaqEx, DATAQ). After 20 minutes of equilibration, electrical field stimuli were applied through two platinum wire electrodes positioned on the top and the bottom of the organ bath separated by 4 cm.

Stimulation Paradigm: The bladder and urethral strips were stimulated with square wave pulses of 0.25 msec duration with maximal voltage (100 V) and a frequency response curve was constructed using 10 and 80 shocks at 1, 2, 5, 10, 20 and 40 Hz. Subsequently, 5 and 50 µM carbachol were added to the bladder preparation to evoke contractions by postsynaptic M3 muscarinic receptor activation, and 90 mM $K^+$ was applied to directly activate the smooth muscle contractile mechanism. In urethral preparations, 20 Hz/10 shock stimulation was applied to evoke contraction via nerve stimulation. Subsequently, 2 µM phenylephrine was added to the bath to check the smooth muscle contractions via the postsynaptic alpha-1 adrenergic receptor activation. 90 mM $K^+$ was then used to check the smooth muscle responsiveness to direct depolarization.

Bladder Inflammation Model: Rats received a single intraperitoneal injection of CYP (100 mg/kg) (Sigma Chemical) for the bladder inflammation model. Myoblasts transduced by adenovirus carrying the iNOS gene, or sham-treated myoblasts, were injected into the rats at the same session under brief pentobarbital anesthesia. The sham-treated control animals received sterile saline injection. Animals were monitored for micturition pattern for 4 days before CMG studies and sacrifice. Bladder tissue was harvested for contractility studies and then processed for immunohistochemical studies.

Urethral Obstruction Model: A modification of the technique described by B. Uvelius and A. Mattiasson, 1984, *J. Urol.*, 132:587-590 and W. D. Steers et al., 1991, *J. Urol.*, 155:379-385 was used to create partial bladder outlet obstruction.

Briefly, female S.D. rats (approximately 250 grams) underwent a partial suture ligation of the proximal urethra under a brief pentobarbital anesthesia through a small midline incision. The urethral diameter was reduced to 1 mm by tying two 4-0 nylon sutures around the urethra and an extraluminally-positioned (1 mm O.D.) polyethylene tube. The tubing was then removed and the abdominal incision was reapproximated. Control animals underwent sham surgery in which the urethra was circumferentially dissected, but not ligated. The animals were closely monitored for complications and overflow incontinence. Four weeks later, myoblasts transduced with an adenovirus construct harboring the gene encoding human iNOS (myoblast-iNOS), or sham saline, was injected in the obstructed and control animals (approximately 8 animals in each of 4 groups). Four days later, the animals were monitored for micturition pattern before CMG studies and sacrifice. Micturition pattern was also performed for 24 hours immediately prior to myoblast injection. Urethral and bladder tissue were harvested for contractility studies and then processed for immunohistochemical studies and PCR.

Purification of Primary Myoblasts: The forelimbs and the hindlimbs were removed from neonatal mice (T. A. Rando et al., 1994, *J. Cell Biol.*, 125:1275-1287; Z. Qu et al., 1998, *J. Cell Biol.*, 142:1257-1267) and the bone was dissected. The remaining muscle mass was minced into a coarse slurry using razor blades. Muscle cells were enzymatically dissociated by the addition of collagenase-type X1 (0.2%) for 1 hour at 37° C., dispase (grade II 240 unit) for 30 minutes and trypsin (0.1%) for 30 minutes. The muscle cell extract was pre-plated on collagen-coated flasks. Different populations of muscle-derived cells were isolated based on the number of preplates performed on collagen coated flasks. Preplate #1 (PP#1) represented a population of muscle-derived cells that adhered in the first hour following isolation; PP#2 represented a population of muscle-derived cells that adhered in the next two hours; PP#3 represented a population of muscle-derived cells that adhered in the next 18 hours; and the subsequent preplates were obtained at 24 hour intervals (PP#4-6). The myogenic population in each flask was evaluated by desmin staining and on differentiation ability when cultured in a fusion medium. The proliferation medium was F10-Ham supplemented with 20% fetal bovine serum and 1% penicillin/streptomycin; the fusion medium was F10-Ham supplemented with 2% fetal bovine serum and 1% antibiotic solution (penicillin/streptomycin). All the culture medium supplies were purchased through Gibco, BRL, Grand Island, N.Y., USA. The first preplate flasks contained a majority of fibroblasts and the last preplate was highly enriched with myogenic cells (desmin positive).

The different populations of cells were infected with β-galactosidase expressing adenovirus. The adenovirus, an E1-E3 deleted recombinant adenovirus kindly obtained through GeneVec Inc. (Dr. I. Kovesdi), had the β-galactosidase reporter gene under the control of the human cytomegalovirus promoter (HCMV), followed by the SV40 t-intron and a poly-adenylation signal (PolyA). The adenovirally transduced cells were then transplanted into the hindlimb muscle (gastrocnemius and soleus) of mdx mice and assayed for their survival post-implantation.

Pure myoblasts were also obtained from isolated viable myofibers as follows: Immediately after cervical dislocation or decapitation of mdx mice, single muscle fibers were prepared from dissected soleus or extensor digitorum longus (EDL) muscle by enzymatic desegregation in 0.2% type 1 collagenase (Sigma, St. Louis, Mo., USA). Isolated muscle fibers from 2-day, 15-day, 1-month, 6-week and 6-month-old mice were used. Due to the small size of 1 to 3-day-old mice, soleus and gastrocnemius were removed en bloc from the lower leg for disaggregation.

Anterior compartment muscles were prepared by cutting the leg at the ankle and knee joints, and adding the entire lower leg to the collagenase solution. Following isolation of 200 myofibers per muscle, a minimum of 5-10 myofibers per well were plated in 6 well plates coated with 1 mg/ml Matrigel (Collaborative Biomedical Products, Bedford, Mass., USA) in 2 ml DMEM medium containing 10% horse serum and 1% chick embryo extract, 2% L-glutamine and 1% penicillin/streptomycin (Sigma Co.). Plates were placed in a 37° C., 5% $CO_2$ incubator for several days. The cells emerging from the cultured myofibers were grown until confluent, assayed for desmin expression, transduced with adenovirus carrying LacZ reporter gene expression and tested for myoblast survival after implantation according to the procedure described herein.

An immortalized mdx cell line was also used. This cell line was isolated from a transgenic animal carrying a thermolabile SV40 T antigen under the control of an inducible promoter as described by J. E. Morgan et al., 1994, *Develop. Biol.,* 162: 486-498. The immortalized mdx cell line proliferated indefinitely under permissive conditions (33° C. with gamma interferon) in proliferation medium (DMEM+20% FBS) and underwent normal differentiation at 37-39° C. without gamma interferon in fusion medium (DMEM+2% FBS).

Adenoviral Vectors: Adenoviral vectors carrying the gene encoding β-galactosidase (i.e., adenovirus-lacZ), the gene encoding bFGF (i.e., adenovirus-bFGF) and the gene encoding iNOS (i.e., adenovirus-iNOS) as described herein have been constructed. The iNOS gene has been cloned and the vector constructs produced as described in D. A. Geller et al., 1993, "Molecular cloning and expression of inducible nitric oxide synthase from human hepatocytes", *Proc. Natl. Acad. Sci. USA,* 90:3491-3495; in E. Tzeng et al., 1997, "Adenoviral transfer of the inducible nitric oxide synthase gene blocks endothelial cell apoptosis", *Surgery,* 122(2):255-263; and in E. Tzeng et al., 1996, "Gene Therapy" (Review), *Current Problems in Surgery,* 33(12):961-1041. The molecular construction of a replication defective adenoviral as employed herein is described in G. Ascadi et al., 1994, *Human Mol. Genetics,* 3(4):579-584. The technique, which involves construction, propagation, purification and titration of the first and third generation adenoviral vector, has been described by S. Kochanek et al., 1996, *Proc. Natl. Acad. Sci. USA,* 93:5731-5736 and G. Ascadi et al., 1994, *Human Mol. Genetics,* 3(4):579-584.

Recombinant human iNOS cDNA was cloned from cytokine-stimulated cultured human hepatocytes as described in D. A. Geller et al., 1993, *Proc. Natl. Acad. Sci. USA,* 90:3491-3495. (Complete cDNA sequence GenBank Accession No. L09210). The cloned iNOS cDNA was subcloned into the adenovirus vector along with a neomycin-resistance gene to yield the DFGiNOS construct. The previously constructed control vector BaglacZ is a retrovirus that expresses the *E. coli* lacZ gene (encoding β-galactoside) under the transcriptional control of the Moloney murine leukemia virus long terminal repeat (MOMLV 5' LTR) and gag pr65 translation initiation codon, and the neomycin-resistance gene under the control of the SV40 early promoter (Price et al., 1987, *Proc. Natl. Acad. Sci. USA,* 84:156-160). Helper-virus-free DFR-iNOS and BaglacZ viral supernatants were generated from CRIP packaging cells (E. Tzeng et al., 1995, *Proc. Natl. Acad. Sci. USA,* 92:11771-11775; E. Tzeng et al., 1996, *I. Surgery,* 120:315-321).

Myoblast Preparation: Primary myoblasts were plated at a density of $5 \times 10^4$ cells per well in a 6-well plate. After 24 hours, the cells were washed with Hank's Balanced Salt Solution (HBSS). Sufficient adenovirus stock was aliquotted into each well to achieve a Multiplicity of Infection equal to 50 (MOI=50). Plates were incubated for 2 hours at 37° C. to allow adequate infection. Proliferation medium (see below) was then added to each well. Plates were incubated at 34° C. for 48 hr. Cells can be immunostained for expression of the transgene or harvested in HBSS for injection into animals. Injections ranged from $1.33 \times 10^5$ to $1 \times 10^6$ cell per 100 μl. Tissue was harvested at 48 hours after injection.

Myoblast Transduction with Adenovirus: Primary myoblasts were grown in culture for 5 days in proliferation medium, which contained DMEM and 15%-20% fetal bovine serum (Gibco-BRL; NY USA). $6 \times 10^5$ myoblasts were infected with adenovirus using a multiplicity of infection (MOI) of 20. Fluorescent latex microspheres (FLMs) were added to the cultured myoblasts at a dilution of 1:1000 to label the myoblasts, thereby allowing the early fate of the injected myoblasts to be followed in vivo (J. Huard et al., 1994, *J. Clin. Invest.,* 93:586-599; J. Huard et al., 1994, *Muscle & Nerve,* 17:224-234; J. Huard et al., 1995, *Gene Therapy,* 2:107-115). At 24 hours post-infection the myoblasts were detached using trypsin (0.25%) for approximately one minute, centrifuged for five minutes at 3500 rpm, and the myoblast pellet was reconstituted with 25 μl of HBSS (Gibco-BRL, NY USA). The harvested cells were transplanted using the technique described below.

Tissue Harvest and Histology: Tissue was harvested at different times depending on the experiment. All bladder and urethra specimens were frozen or fixed in 10% buffered formalin depending on the requirement of the assay. The area around each injection site was examined microscopically, stained for LacZ reporter gene and immunohistochemistry, and photographed. Appropriate assays for the LacZ reporter gene and fibroblast growth factor gene expression were carried out.

LacZ Staining by Histochemical Technique: The cryostat sections of the injected and control tissues were stained for LacZ expression as follows. Sections were first fixed with 1.5% glutaraldehyde (Sigma) for one minute, rinsed twice in phosphate-buffered saline (PBS) and then incubated in X-gal substrate [0.4 mg/ml 5-bromo-chloro-3-indolyl-β-D-galactoside (Boehringer-Mannheim, Indianapolis Ind., USA), 1 mM $MgCl_2$, 5 mM $K_4Fe(CN)_6$/5 mm $K_3Fe(CN)_6$ in PBS)] overnight at 37° C.

Assay for β-Galactosidase Activity: This technique provided better quantification and comparison of the level of transgene expression in infected cells as well as in injected tissues (e.g., muscle, bladder, urethra). The injected muscle was frozen in liquid nitrogen and homogenized in 0.25 M Tris-HCl (pH 7.8) and the homogenates were centrifuged at 3,500×g for 5 min. The muscle homogenate was disrupted by 3 cycles of freeze/thaw and the supernatant was recollected by centrifugation (12,000×g/5 min. at 4° C.) and transferred to a clean microcentrifuge tube. Thereafter, 30 μl of this extract was mixed with 66 μl of 1× o-nitrophenyl-β-D-galactopyranoside; ONPG (4 mg/ml ONPG in 0.1 M sodium phosphate pH 7.5), 3 μl of 100×Mg solution (0.1 M. $MgCl_2$, 4.5 M β-mercaptoethanol), 201 μl 0.1 M sodium phosphate (41 ml of 0.2 M $Na_2HPO_4$. $2H_2O$, 9 ml of 0.2 M $NaH_2PO_4$. $2H_2O$ and 50 ml $H_2O$) and then incubated at 37° C. for 30 minutes, or until a faint yellow color had developed. Finally, the reaction was stopped by adding 500 μl of 1 M $Na_2CO_3$ and the optical density was read on a spectrophotometer at a wavelength of 420 nm. The level of β-galactosidase activity (# of units/sample) was extrapolated on a calibration curve which converts the optical density at 420 nm to the concentration of β-galactosidase enzyme.

Determination of the Persistence of Myoblast Injection: Myoblasts were incubated with FLMs and transduced with adenovirus carrying the β-galactosidase reporter gene. Each flask of 500,000 cells was trypsinized using 0.5% Trypsin-EDTA, centrifuged at 3500 rpm for 5 minutes, and resuspended in 100 μl of medium. The solution from one flask was injected into the urethra or bladder of the animals. A 25 μl solution of infected muscle cells ($1 \times 10^6$ cells) was injected into the urethra using a Hamilton syringe.

At the various sacrifice intervals, the urethra and bladder were removed. After contractility studies, the tissue was snap frozen using 2-methylbutane pre-cooled in liquid nitrogen. Analysis of the sections included hematoxylin-eosin staining; X-gal staining; desmin immunohistochemistry and localization of the FLMs. From these analyses, the location and viability of the injected cells were determined. In addition, using different myogenic markers, such as desmin and myosin heavy chains, it could be determined if any myoblast fusion had occurred with the internal structures of the joint. Desmin and myosin heavy chains are assayed to demonstrate that the muscle-derived cells carry the reporter gene and that reporter protein, e.g., LacZ, is expressed. By co-localizing the LacZ reporter gene with genes encoding muscle structural proteins (e.g., desmin and myosin heavy chains), it could be determined that LacZ expression results from the fusion of the injected cells. Myosin heavy chains are only expressed in muscle cells under differentiation (i.e., myotubes and myofibers).

Statistical comparison of the efficiency of myoblast fusion among the primary cultures was made by counting the number of transduced myoblasts and myofibers in the urethra. In addition, by using the ONPG assay, statistical comparisons of the level of β-galactosidase expression mediated by injection of transduced myoblasts could be made at each time interval. The number of transduced myoblasts and myofibers that decreased over time in the injected urethra and bladder was able to be determined.

iNOS Immunohistochemistry: Tissue was harvested and fixed as described for β-galactosidase staining. Sections were mounted on gelatin-coated slides. Endogenous peroxidases were inactivated with 0.5% $H_2O_2$ in absolute MeOH for 30 minutes at room temperature. Slides were incubated at room temperature for 1 hour with anti-iNOS (mouse monoclonal, Transduction Laboratory) in normal goat serum (1:50). Biotinylated anti-mouse (goat, Kirkengaard-Perry) was incubated for 30 minutes at room temperature, followed by incubation with strepavidin-horseradish peroxidase for 30 minutes. Slides were developed by the addition of diaminobenzidine (1 mg/ml)/hydrogen peroxide (0.03%) reagent and allowed to develop for 3 to 5 minutes.

NOS Immunostaining of Myoblasts: Cells were fixed with 4% paraformaldehyde for 20 minutes and were permeabilized with cold methanol (−20° C.) for 10 minutes. 1% bovine serum albumin in PBS was used to block cells and dilute reagents. Diluted anti-iNOS antibody (1:250 dilution, rabbit polyclonal, Santa-Cruz) was incubated at room temperature for 60 minutes. Biotinylated anti-mouse (goat, Kirkengaard-Perry) was incubated for 30 minutes at room temperature, followed by incubation with strepavidin-cy3 (strepavidin bound to a red fluorescent marker) for 30 minutes. Wells were examined under a microscope. In addition, anti-adenovirus protein antibody (Santa-Cruz) was selectively used to confirm that the myoblasts were transduced with the appropriate adenovirus vector.

Nitrite ($NO_2^-$) Measurement: Cells were passaged to 24 well plates. After 24 hours, the cell medium was replaced with medium alone or medium containing H4B (100 μM; Sigma). Accumulated $NO_2^-$ in the supernatants was quantified by employing the Griss reaction (L. C. Green et al., 1982, *J. Analyt. Biochem.*, 126:131-138) using sodium nitrate as standard.

Determination of Nitric Oxide (NO) Formation: NO formation was measured and compared in bladder and urethra of iNOS treated versus sham treated animals. NO formation was estimated by comparing the tissue content of its stable oxidation product, nitrite, in the stimulated and unstimulated strips. Tissue nitrite content was measured using a previously described calorimetric technique (L. J. Ignarro et al., 1987, *Biochem. Biophys. Res. Commun.*, 170:843-850). The weighed tissue samples were placed in a glass tube and thawed in 0.5 ml of ice-cold methanol. The tissue was then homogenized using a glass pestle. The homogenate was allowed to stand for 18 hr at 4° C. to ensure complete extraction of nitrite. Samples were then placed in a refrigerated centrifuge at 4° C. and centrifuged at 15,000×g for 15 minutes. An aliquot (0.3 ml) of each sample was mixed with 0.4 ml of 1% sulfanilic acid in 0.4 M HCl. After 10 min, 0.3 ml of 1% N-(1-naphthy)-ethylene diamine in methanol was added and the absorbance of the resultant pink complex was measured in a spectrophotometer at a wavelength of 548 nm. Nitrite concentration was interpolated from a standard line constructed by performing an identical assay using sodium nitrite standards in the range of 0.5-5 μM, together with methanol blanks.

NOS Activity Assay: NOS activity was measured and compared in bladder and urethra of iNOS treated versus sham treated animals by monitoring the conversion of [$^3$H]-L-arginine to [$^3$H]-L-citrulline as described by A. L. Burnett, 1995, *Urology*, 45:1071-1083; D. S. Bredt and S. H. Snyder, 1990, *Proc. Natl. Acad. Sci. USA*, 87:682-685).

Briefly, tissues were homogenized in ice cold homogenization buffer. Enzyme assays contained 25 μl of tissue supernatant and 100 μl of 1 μCi/ml [$^3$H]-L-arginine, 1.2 mM NADPH, and 0.7 mM $CaCl_2$. After a 15 minute incubation at room temperature, the assays were terminated by the addition of 3 ml of 20 mM Hepes (pH 5.5) with 2 mM EDTA. The entire mixture was applied to 0.5-ml columns of Dowex-50W cation exchange resin (Na+ form) to remove unreacted [$^3$H]-L-arginine. [$^3$H]-L-citrulline in the column eluate was quantified by liquid scintillation spectroscopy. The recovery rate of [$^3$H]-L-citrulline from the columns was measured for all tissues by preincubating each tissue supernatant with a known concentration of [$^3$H]-L-citrulline and then measuring the [$^3$H]-L-citrulline in each column eluate. Column saturation studies were also done to ensure that all of the [$^3$H]-L-arginine was retained in the column. Additional assays were performed in the presence of excess L-nitroarginine methyl ester (L-NAME), a competitive inhibitor of NOS, to verify the specificity of the assay for the production of [$^3$H]-L-citrulline by NOS catalysis.

Interassay variations were controlled for by standardizing NOS activity measurements in tissue against the activity measured in the NOS-rich rat cerebellum which was analyzed in parallel for each assay. The level of citrulline will be expressed as picomoles per mg of tissue per minute.

RNA Isolation and Northern Blot Analysis: Total cellular RNA was isolated from uninfected, BaglacZ and human iNOS treated animals using RNA-zol B as previously described (P. Chomczynski and N. Sacchi, 1987, *Analytical Biochemistry*, 162:156-159). Aliquots (20 μg) of RNA were electrophoresced on a 0.9% agarose gel and blotted onto GeneScreen (DuPont-NEN, Boston, Mass.). After prehybridization, the membranes were hybridized to a DNA probe (D. A. Geller et al., 1993, *Proc. Natl. Acad. Sci. USA*, 90:522-526; D. A. Geller et al., 1993, *Proc. Natl. Acad. Sci. USA*, 90:3491-3495). A 2.3 Kb human iNOS cDNA fragment served as the iNOS probe, while a 4.1 Kb human endothelial cNOS (ecNOS) cDNA fragment served as the ecNOS probe. 18S rRNA served as a control for relative RNA loading.

Reverse Transcriptase-Polymerase Chain Reaction (RT-PCR) Amplification: Samples were immediately frozen in liquid nitrogen and stored at −80° C. Total cellular RNA was extracted from the samples using the method of P. Chomczynski and N. Sacchi, 1987, *Analytical Biochemistry*, 162: 156-159. Total RNA was subjected to first-strand cDNA synthesis using oligo (dT) primer and MMLV reverse transcriptase (E. S. Kawasaki, PCR Protocols: a guide to methods and applications, Eds. M A Innis, D H Gelfang, J J Sninsky, and T J White, Academic Press, New York. pp. 22-27, 1990). Primers were designed to amplify iNOS with the assistance of a PCR primer design program, PCR Plan (Intelligenetics, Mountain View, Calif.). The sequence of the iNOS 5' oligonucleotide primer (18 bp) used was 5'-AGGA-CATCCTGCGGCAGC-3' (SEQ ID NO:1) (E. Tzeng et al., 1996, *Mol. Med.*, 2(2):211-225) spanning from base pair 3426 to 3444 of the human iNOS cDNA sequence (D. A. Geller et al., 1993, *Proc. Natl. Acad. Sci. USA*, 90:3491-3495). The sequence of the iNOS 3' oligonucleotide primer (18 bp) was 5'-GCTTTAACCCCTCCTGTA-3' (SEQ ID NO:2) (E. Tzeng et al., 1996, *Mol. Med.*, 2(2):211-225) spanning from base pair 3724 to 3741 of the human iNOS cDNA sequence (D. A. Geller et al., 1993, *Proc. Natl. Acad. Sci. USA*, 90:3491-3495). The identity of the amplified cDNA fragment obtained from the RT-PCR reaction with iNOS primers (approximately 316 bp) was confirmed using restriction enzyme analysis.

PCR conditions were as follows: denaturation at 94° C. for 1 min; annealing at 57° C. for 1 min; polymerization at 72° C. for 2 min. PCR reactions were performed in a Perkin Elmer 480 thermocycler using different numbers of cycles to detect a linear range of input RNA. The optimal cycle number was identified as 30 cycles. Rat peritoneal macrophages elicited with thioglycolate and RAW cells (RAW 264.7 macrophage cell line) stimulated in vitro with LPS served as positive controls for iNOS mRNA. The negative control for each set of PCR reactions contained water instead of DNA template. PCR product (20% of the reaction volume) of qualitative RT-PCR was separated by electrophoresis on a 2% agarose gel and stained with ethidium bromide.

For semiquantitative RT-PCR (E. S. Kawasaki: Amplification of RNA. PCR Protocols: A guide to methods and applications, Eds. M. A. Innis, D. H. Gelfang, J. J. Sninsky and T. J. White, Academic Press, New York. pp. 22-27, 1990). $^{32}$P endlabeled 5' primer was used. Fifteen µl of the PCR reaction was separated on a 10% polyacrylamide gel. After gel drying and exposure to a PhosphorImager screen (Molecular Dynamics PhosphorImager, Sunnyvale, Calif.), the relative radioactivity of the bands was determined by volume integration using laser scanning densitometry. Each gel contained the same positive control which permitted normalization of samples and comparison among gels.

In Vivo Extraskeletal Bone Formation Assay: A retroviral vector carrying the expression of the β-galactosidase gene (rv-lacZ) and adenovirus engineered to express the BMP-2 gene (AdV-BMP-2) were used in these experiments. The BMP2-125 plasmid was digested with Sal I, and the 1237 bp fragment containing the entire cDNA for human BMP-2 was isolated. The BMP-2 cDNA was then inserted into the Sal I site of the pAd.lox plasmid such that the translation start site was then obtained by cotransfection of pAd.10× with psi-5 viral DNA into CRE-8 cells as previously described by S. Hardy et al., 1997, *J. Virol.*, 71:1842-1849).

Primary mdx pp6 cells were transduced with rv-lacZ as a method of monitoring the in vivo fate of these cells. $1 \times 10^6$ cells were plated in a T-75 flask. Proliferation medium (F10/HAM media containing 20% fetal bovine serum) was washed off with serial rinses of Hank's Balanced Salt Solution (HBSS, Gibco BRL). Three milliliters of rv-lacZ suspension, at a concentration of approximately $5 \times 10^5$, and 6 µl polybrene diluted with 2 ml HBSS, were incubated with the cells for 6 to 8 hours at 37° C. Thereafter, proliferation medium was added to the cells, and the cells were allowed a recovery period of 24 hours prior to AdV-BMP infection. After the 24 hour period, these cells were again rinsed with HBSS and transduced with AdV-BMP at a multiplicity of infection (MOI) of 50. The cells were incubated with the viral suspension for 4-6 hours, at which time proliferation medium was added without removal of viral particles.

Prior to injection, cells were rinsed multiple times in HBSS and counted. Injections of $3.0 \times 10^5$ cells suspended in 20 µl of HBSS were performed in severe combined immune deficient (SCID) mice hindlimb muscle. The cell suspension was then injected with a 30 gauge needle on a gas tight syringe into the exposed triceps surae. Animals were sacrificed at 2, 3, 4, and 5 weeks post-injection.

Ectopic bone formation in the injected limb was analyzed by gross inspection, radiograph, and standard histology. Limbs from sacrificed mice were radiographed with a dental radiography machine. Limbs were then flash frozen in 2 methylbutane buffer pre-cooled in liquid nitrogen. Frozen samples were sectioned into 10-12 µm sections using a cryostat (Fisher Scientific). After fixation with glutaraldehyde (1%), muscle sections were incubated with the X-gal substrate for 1-3 hours to reveal the β-galactosidase activity. Further histological analysis included von Kossa, hematoxylin, and eosin staining. All animal procedures were with the guidelines and approval of Children's Hospital and the University of Pittsburgh Animal Care Committee according to protocol 1/98.

Diffusion Chamber Implantations: Primary pp6 cells were transduced in vitro with AdV-BMP-2 using an MOI of 50. The cells were trypsinized, counted and $1 \times 10^6$ cells were suspended in proliferation medium. Under sterile conditions, the cells were loaded 5 microliter Theracyte immunoisolation devices (Device Engineering Group, Baxter Healthcare, Round Lake, Ill.) using a gas tight syringe and blunt tipped stainless steel needles (J. Brauker et al., 1998, *Human Gene Ther.*, 9:879-888). The loading port was sealed with sterile silicone adhesive (Dow Corning, Midland, Mich.). The Theracyte devices consist of a bilayer polytetrafluoroethylene (PTFE) membrane with an outer membrane pore size of 5 micrometers and an inner membrane pore size of 0.4 micrometers. The bilayer PTFE membrane precludes host cells from entering the device and implanted cells from exiting the device. The devices were implanted subcutaneously in SCID mice under ketamine and xylazine anesthesia. The mice were sacrificed three weeks later using methoxyflurane anesthesia and cervical dislocation. The devices were flash frozen in 2-methylbutane precooled with liquid nitrogen. 10 micrometer thick sections were made using a Cryostat (Microm, HM 505 E) and stained with hematoxylin and eosin, with and without von Kossa's stain Example 2

Experiments were performed using myoblast injection into the urethral wall as a treatment for stress urinary incontinence.

In these experiments, myoblasts from the GH8 myoblast cell line (available from the American Type Cell Culture depository) transduced with an adenoviral vector harboring a reporter gene encoding β-galactosidase (E1-E3 deleted first generation adenovirus), were cultured and injected into the proximal urethral wall of the female S.D. rat.

In addition, the cells were incubated with fluorescent latex microspheres (FLM) to follow the fate of the injected cells (see Example 1). The transduced, FLM-labeled cells were injected into adult female S.D. rats (n=20). A midline incision was made and myoblasts were injected into the proximal urethral wall at two sites with a 10 µl Hamilton micro syringe. The myoblast concentration ranged from $1.33 \times 10^5$ to $1 \times 10^6$. The tissue was harvested 2-4 days after injection and flash frozen in liquid nitrogen. The tissue was then sectioned, stained with x-gal substrate and then counterstained with Hematoxylin and Eosin (H and E). Photographs of the slides were taken under light and fluorescence microscopy (FIGS. 1A-1I).

Injection was done in the urethra of control animals and also in animals that had urethral injury using a 8 mm diameter aluminum probe cooled in dry ice and then placed on the ventral urethra for 10 seconds (see Example 1). After 2, 4, and 7 days, animals with and without urethral injury were euthanized and the portion of the urethra containing the engrafted myoblasts, as well as adjacent normal urethra and bladder, were removed and subjected to functional and microscopic studies. Twenty-four hours prior to sacrifice, the animals underwent micturition pattern analysis in a metabolic cage to determine change in voiding volume and frequency (see Example 1).

Animals with and without urethras engrafted with myoblasts also underwent a 24-hour micturition pattern analysis in a metabolic cage using methods described by M. B. Chancellor et al., 1994, *J. Urol.*, 151:250-254.

Immediately prior to sacrifice, animals underwent urethral pressure urodynamic study (cystometrogram (CMG)) under urethane anesthesia using specially designed urodynamic catheters to allow simultaneous but isolated measurement of bladder and urethral pressure (H. Kakizaki et al., 1997, *Am. J. Phy.*, 272:R1647-1656).

Urethral perfusion pressure and isovolumetric bladder pressure were measured with catheters inserted through the bladder dome. These parameters were compared in myoblast-injected animals and in sham-injected animals, with and without cryoprobe injury. For these evaluations, specially designed urodynamic catheters were employed to allow simultaneous but isolated measurement of bladder and urethral pressures. The catheter assembly was wedged in the bladder neck to block passage of fluid between the bladder and urethra without affecting the nerve supply to the organs, as described in Example 1. The external urethra was not catheterized. Responses were examined at a urethral saline infusion speed of 0.075 ml/min.

After the urodynamic experiments, urethral strips were harvested and placed in Krebs-filled bath chambers to assess contractility. Control and sham-injected animals were assessed. Histochemistry staining for lacZ and fluorescent microscopic analysis were performed to evaluate and quantify the survival and differentiation of myoblasts and to assess the production of myotubes. Long-term experiments using autologous primary myoblast injection described herein into the urethra were carried out for 30-60 days.

The results of the foregoing analyses are presented in Table 1.

TABLE 1

| Urethra Injection of Myoblast vs. Control | Control (n = 12) | Myoblast (n = 4) |
|---|---|---|
| Micturition Pattern | | |
| 24 hr. urine volume (ml) | 21.8 +/− 3.8 | 19.8 +/− 4.2 |
| Urine frequency/24 hr | 19 +/− 5 | 11 +/− 3 |
| Mean micturition volume (ml) | 1.0 +/− 0.4 | 1.8 +/− 0.9* |
| Urethral Studies | | |
| Baseline urethral pressure (mmHg) | 28.3 +/− 3.1 | 36.4 +/− 5.5** |

TABLE 1-continued

| Urethra Injection of Myoblast vs. Control | Control (n = 12) | Myoblast (n = 4) |
|---|---|---|
| Bladder contraction pressure (mmHg) | 78.3 +/− 11.2 | 72.8 +/− 23.3 |

*($p < 0.01$);
**($P < 0.5$)

These experiments demonstrated a large number of cells in the urethral wall expressing β-galactosidase and containing FLM under fluorescent microscopy. Many regenerative myofibers expressing β-galactosidase were also seen in the urethral wall. Primary myoblasts injected into SCID mice survived for over 30 days. Animals treated with myoblast injection were discovered to have increased (urethral pressure). In animals having cryoprobe injured urethras, myoblast injection resulted in improved contractility.

Example 3

Experiments were performed to demonstrate the feasibility of myoblast injection into the bladder wall to improve detrusor contractility. A myoblast cell line transduced with an adenovirus vector carrying a β-galactosidase reporter gene as described hereinabove was used for these experiments. The cells were incubated with fluorescent latex microspheres (FLM) to follow the fate of the injected cells. Cells were injected into adult male and female S.D. rats (n=18). The myoblasts were injected into the dome of the bladder and into the right and left lateral walls near the dome with a 10 μl Hamilton microsyringe. The myoblast concentration ranged from $1.33 \times 10^5$ to $1 \times 10^6$ cells. The tissue was harvested after 2-5 days, sectioned and assayed for β-galactosidase expression. For gene therapy experiments, myoblasts were transduced with the adenovirus containing the human inducible nitric oxide synthase (iNOS) gene at a multiplicity of infection of 50 (MOI=50) and were injected into the bladder and studied after 2 to 7 days. The results of these experiments demonstrated that in the bladder wall there were a large number of cells expressing B-galactosidase and containing FLM's as determined by fluorescence microscopy. Many regenerative myofibers expressing β-galactosidase were also seen in the bladder wall. Using a porphyrinic microsensor to measure NO, increased basal release of NO (20 nM) was detected from the bladder wall area injected with myoblasts that had been transfected with the iNOS gene.

These studies demonstrated the survival of myoblasts and the expression of foreign genes in myoblasts following injection into the bladder wall. Thus, myoblast injection and myoblast mediated gene therapy were shown to be useful for modulating detrusor contractility and for counteracting overactive bladder function.

Figure 2:
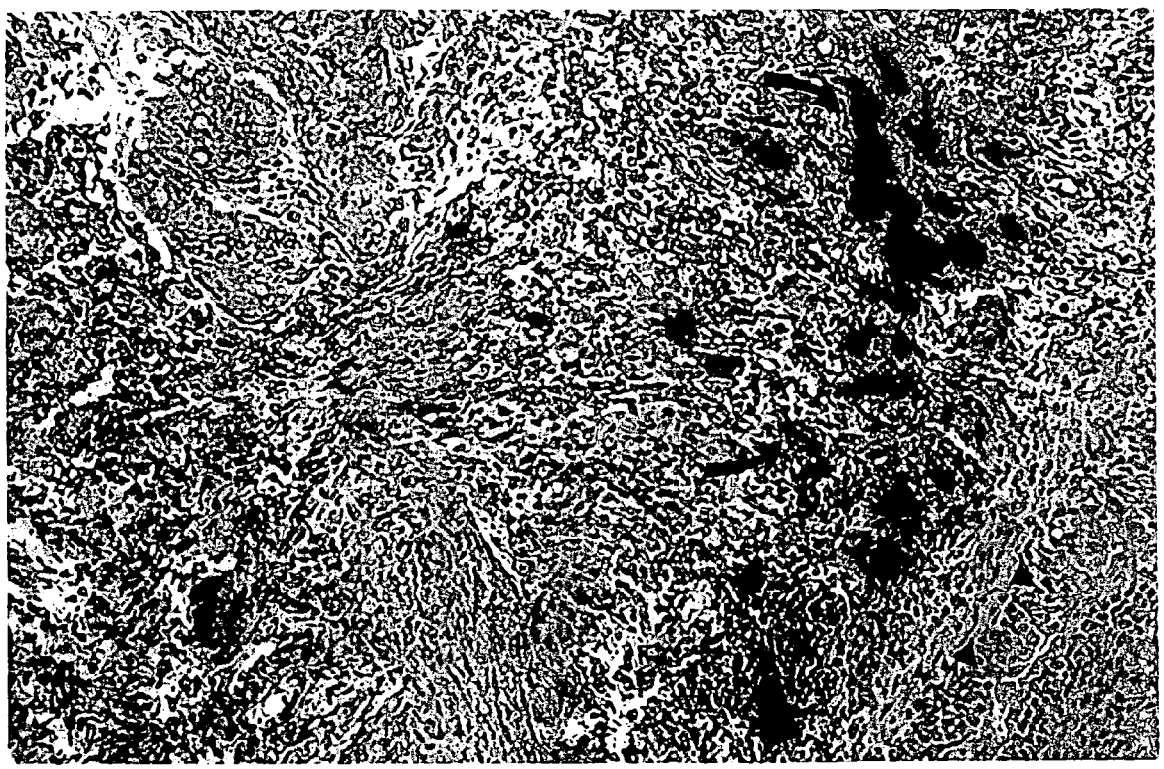
FIG. 2 shows a high magnification (i.e., 100×) of myoblast injection into the urethral wall as shown in FIG. 1I. Transduced myoblasts, myotubes and myofibers expressing β-galactosidase (blue color, arrows) are seen in the urethral wall near urethral epithelium (arrow heads). H and E tissue staining was used.

Bladder or urethral wall cryoinjury was performed in a rat (S.D.) model as described in Example 1. Two animals each underwent cryoinjury and sham injury with and without myoblast injection. Four days after cryoinjury and myoblast injection the contractility evaluation was performed. Significant histological damage to the bladder and urethral wall were observed after cryoinjury (FIG. 2). The muscle contractility to electrical field stimulation disappeared after cryoinjury, compared with no change in sham injured animals.

Bladder or urethral strips were mounted in organ baths of 5 mL and were electrically stimulated with 100V, 0.25 ms at various frequencies. Both the cryo damaged bladder and urethral strips showed low and no contractile activity to electrical field stimulation, to indirect smooth muscle activation via M3 receptor stimulation by carbachol, or to direct smooth muscle activation with high $K^+$, compared with the non-damaged controls. After myoblast treatment of the cryo-damaged bladder or urethra there was a significant recovery of the contractile activity to electrical stimulation.

The results are presented in Table 2.

TABLE 2

| Micturition Pattern of Bladder Cryoinjury Versus Control | Control (n = 12) | Cryoinjury (n = 4) |
|---|---|---|
| 24 hr. urine volume (ml) | 21.8 +/− 3.8 | 19.8 +/− 4.2 |
| Urine frequency/24 hr | 19 +/− 5 | 11 +/− 3 |
| Mean micturition volume (ml) | 1.0 +/− 0.4 | 1.8 +/− 0.9* |

*(p < 0.01)

These experiments clearly demonstrated an alteration of bladder and urethral function with the cryoinjury model.

Example 4

Experiments were performed to assess the long-term survival of autologous transduced myoblasts in the bladder and urethra.

These experiments were performed in mice having severe combined immune deficiency, i.e., the SCID mouse model, and subsequently in non-immunodeficient rats. Autologous myoblasts and muscle-derived cells were harvested and cultured in sufficient quantity for repeated bladder injections.

The primary myoblast cultures were grown for 3 days in a proliferating medium supplemented to contain DMEM and 15% fetal bovine serum (Gibco-BRL). The myoblasts were infected with adenovirus vector. Fluorescent latex microspheres (0.5 μm) were also added to the cultured myoblasts at a dilution of 1:1000 to allow the fate of the injected myoblasts to be followed in vivo (A. Satoh et al., 1993, *J. Histochem. Cytochem.*, 41:1579-1582; S. Floyd et al., 1997, *Basic Appl. Myol,* 7(3&4)). At 48 hours post-infection, the myoblasts were detached from the culture container using Trypsin (0.25%), centrifuged for 5 minutes at 3,500 rpm, and the myoblast pellet was reconstituted with 25 ml of Hank's balanced salt solution (HBSS, Gibco-BRL, NY USA).

The transduced myoblast solution was injected into the detrusor wall on the left side, with the same number of viral particles injected into the contralateral side of the animal. The injected mice were sacrificed at 4 days post-injection. The bladders from the injected animals were removed and snap-frozen in isopentane pre-cooled in liquid nitrogen. The muscle was then cryostat-sectioned in its entirety in a 10 μm thickness and prepared for staining.

The same viral solution was (i) directly injected intramuscularly or (ii) used to transduce myoblasts in vitro prior to the ex vivo gene transfer to the same animal. Newborn (two to five day-old) and adult (two month-old) normal mice were injected with isogenic myoblasts (on the right side of the bladder with the same amount of viral particles as was used to infect myoblasts that were injected into left side of bladder) and were sacrificed at three days post-injection. Approximately 8 animals were assessed in each group. The injected muscles were assayed for both β-galactosidase activity and for LacZ staining and the efficiency of gene delivery was monitored. After 2, 4, 7, 14, 30, 60, and 90 days, animals were euthanized and the portion of the bladder containing the engrafted myoblasts, as well as adjacent normal bladder, were removed and analyzed.

The level of transgene expression was statistically compared between the direct and the ex vivo gene transfer approaches using adenovirus. The bladders injected with isogenic myoblasts were longitudinally sectioned to determine the presence of regenerating myofibers. Immunohistology staining for lacZ and fluorescent microscopy analysis were performed to evaluate and quantify the survival and differentiation of myoblasts and to assess the production of myofibers. The location of transduced myofibers containing a non-uniform distribution of FLMs allowed the determination of the presence of mosaic myofibers. Using immunohistology staining for LacZ and FLMs analysis, it was determined that there were survival and differentiation of injected myoblasts into myofibers.

Figure 15A:
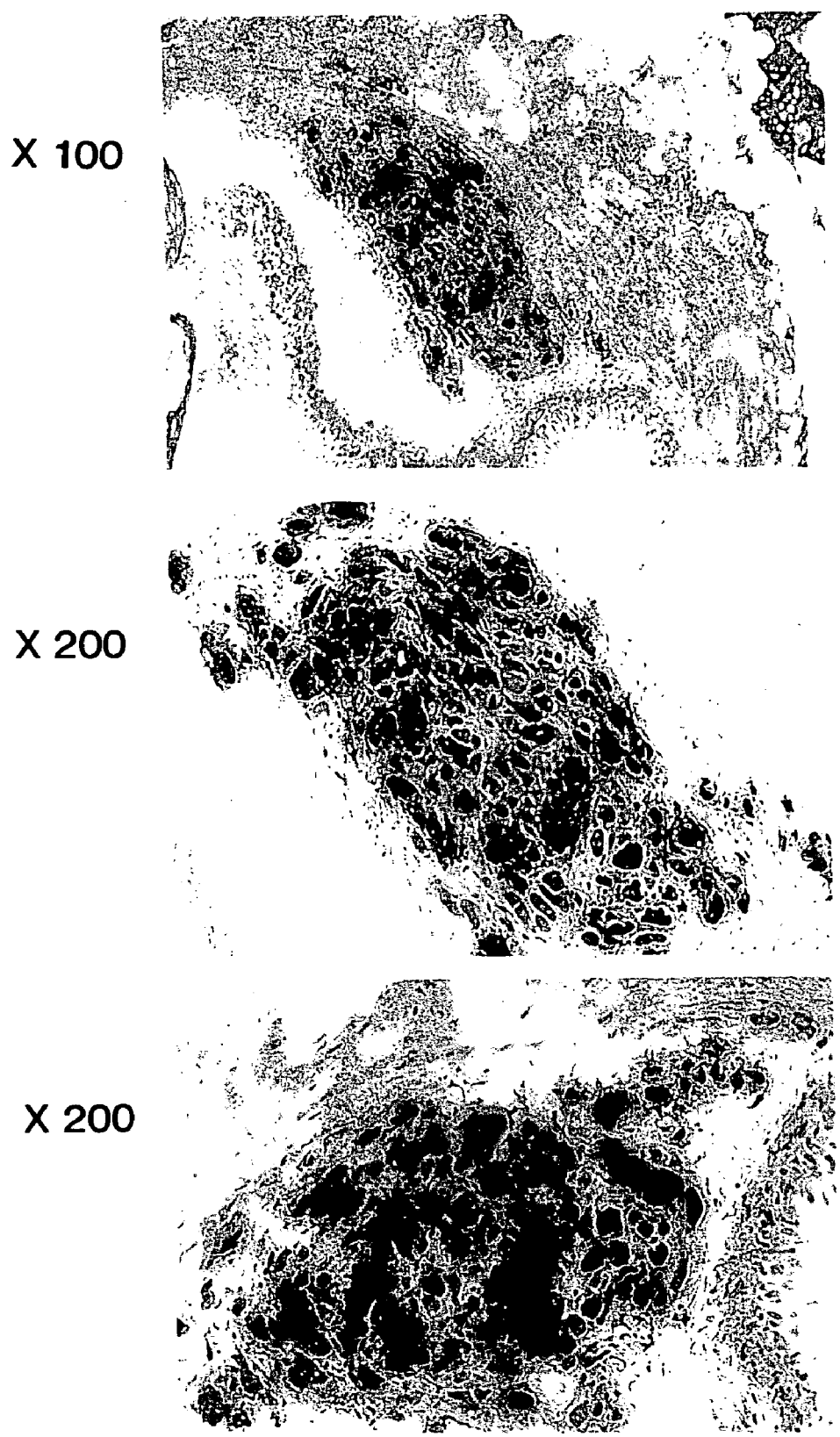
FIGS. 15A-15C show the results of primary muscle-derived cell injection into the lower urinary tract. (Example 4) Myoblasts transduced with an adenovirus vector carrying the gene encoding β-galactosidase (LacZ) were injected into mouse bladder and urethra.
Figure 15B:
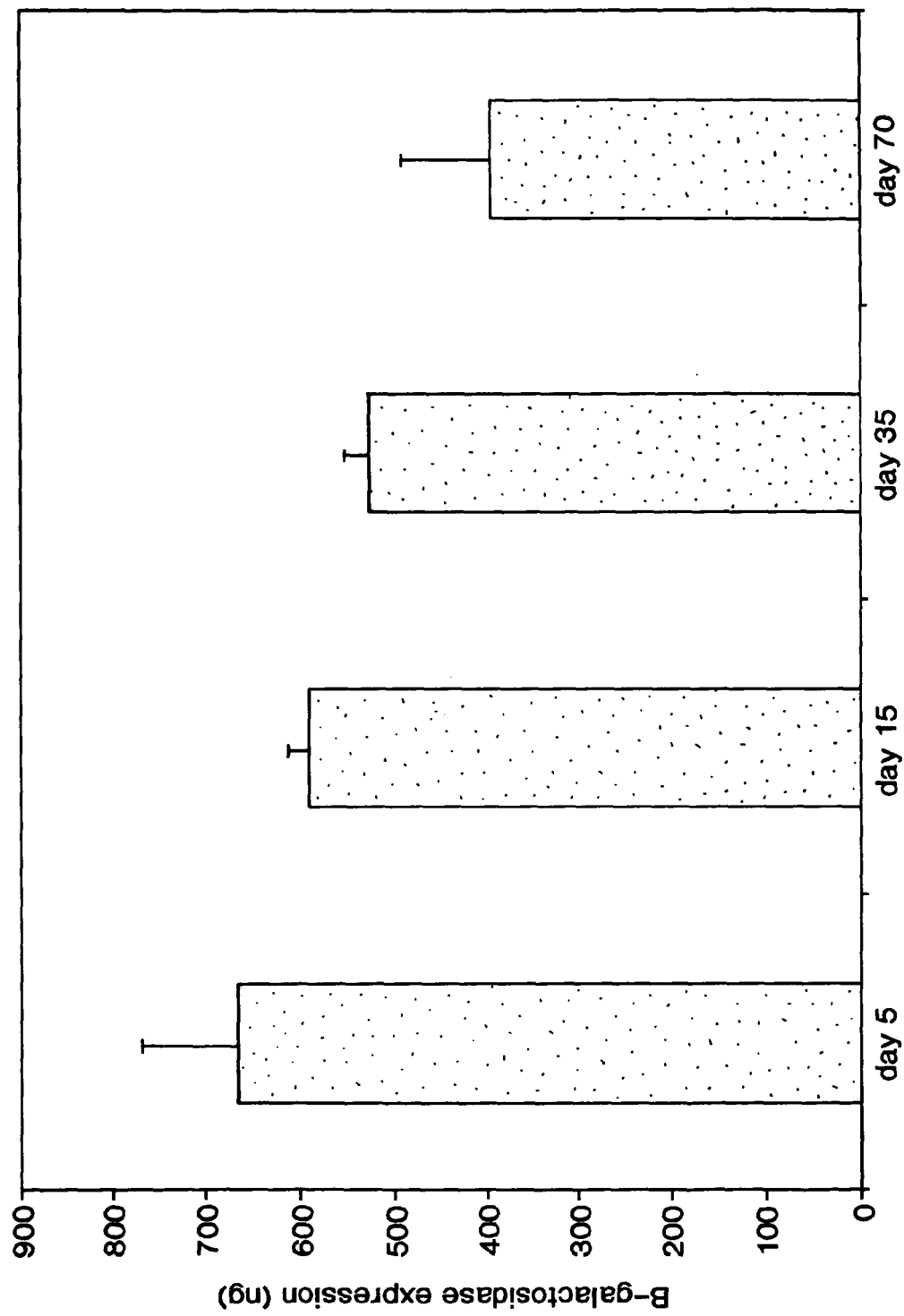
Figure 15C:
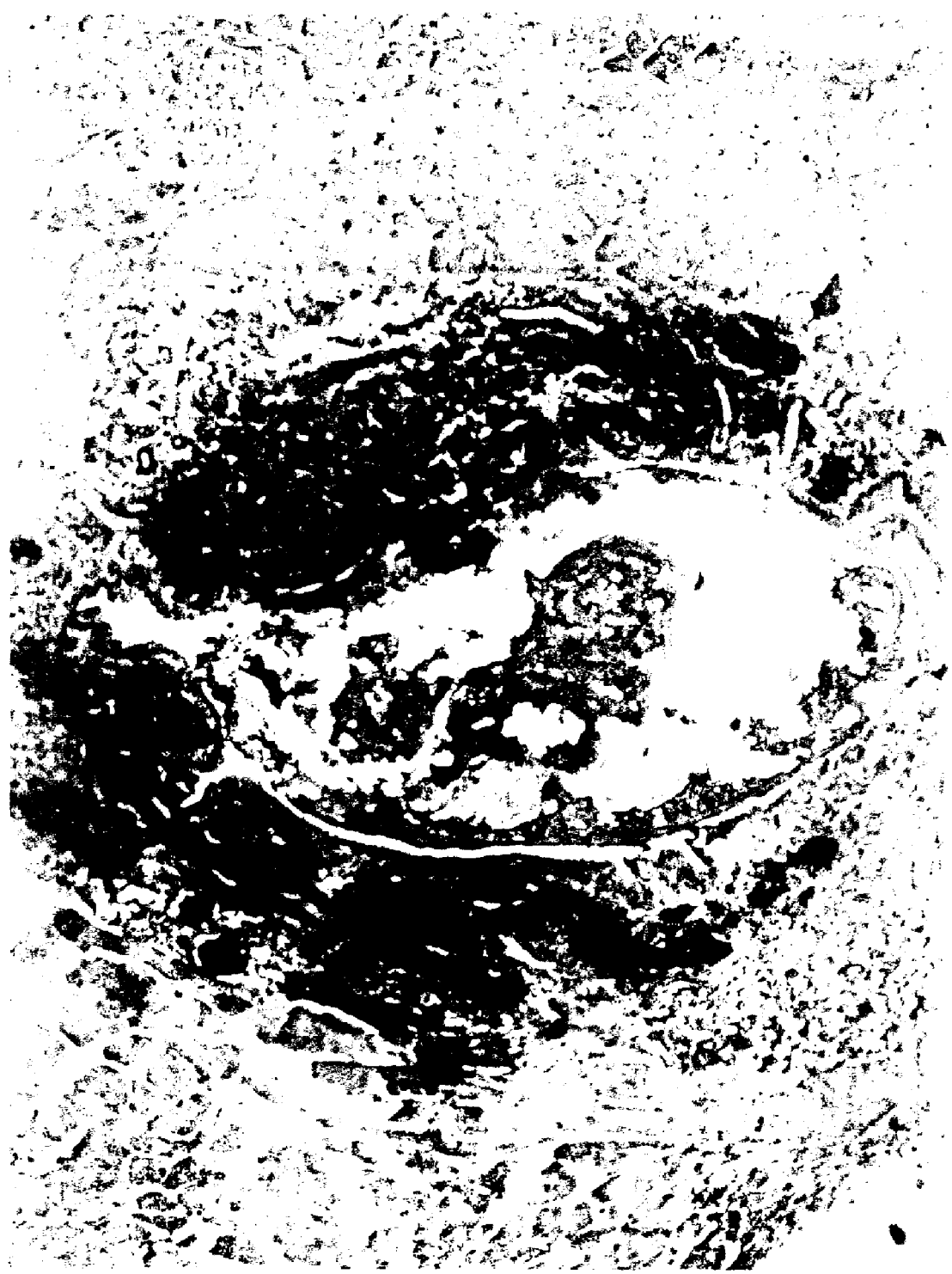

The results from these analyses demonstrate that autologous myoblast cells can be characterized, cultivated and stored. In addition, autologous myoblasts were shown to be successfully engrafted into the bladder and urethra without significant immunoreactivity for at least 90 days up to 6 months. More specifically, the injection of primary muscle-derived stems cells into the bladder was able to achieve long-term survival and over 50% persistence at 6 months. In addition, maintenance of persistent bulking effect was demonstrated in the urethral wall. Such maintenance is necessary for the treatment of stress urinary incontinence (FIGS. 15A-15C).

Example 5

Further experiments as described in this example were carried out to evaluate and improve the survival of injected myoblasts post-injection. In order to perform this evaluation, different mdx myoblast cell lines (see below), as well as primary myoblasts, at different purities as described below, injected into the muscle of adult mdx mice. The myoblasts were either adenovirally transduced or transfected with a β-galactosidase expressing plasmid and the early fate of the injected cells was evaluated post-injection.

The plasmid containing the gene encoding β-galactosidase was constructed on a pBluescript plasmid backbone, in which the β-galactosidase reporter gene is driven by the human cytomegalovirus (HCMV) promoter, and the neomycin-resistance gene is driven by the PGL promoter. (J. A. Wolff et al., 1990, *Science,* 247:1465-1468; S. Jiao et al., 1992, *Human Gene Therapy,* 3:21-33).

Different populations of primary myoblasts which had been purified by preplating (Example 1), and having a percentage of myoblasts ranging from between about 10% to 90%, were assayed. Finally, primary mdx myoblasts obtained from isolated myofibers were also used and compared among the groups for the survival of the injected cells (see J. Huard et al., 1994, *Human Gene Ther.,* 5:949-958 and J. Huard et al., 1994, *J. Clin. Invest.,* 93:586-599).

The different populations of preplated myoblast cells were infected with β-galactosidase expressing adenovirus. The adenovirus, an E1-E3 deleted recombinant adenovirus kindly obtained through GeneVec Inc. (Dr. I. Kovesdi), had the β-galactosidase reporter gene under the control of the human cytomegalovirus (HCMV) promoter and followed by the SV40 t-intron and polyadenylation (PolyA) signal. The adenovirally transduced cells were then transplanted into the hind-limb muscle (gastrocnemius and soleus) of mdx mice and assayed for their survival post-implantation.

Myoblasts were isolated from single viable myofibers. Single muscle fibers were prepared from dissected extensor digitorum longus (EDL) muscle by enzymatic desegregation in 0.2% type 1 collagenase (Sigma, St. Louis, Mo., USA), as previously described (D. J. Rosenblatt et al., 1995, *In Vitro Dev. Biol.* 31:773-779; W. G. Feero et al., 1997, *Gene Ther.*, 4:371-380). Isolated muscle fibers from 6 week old mice were used. Following the isolation of approximately 200 myofibers per muscle, a minimum of 5-10 myofibers per well were plated on 6 well plates coated with 1 mg/ml Matrigel (Collaborative Biomedical Products, Bedford, Mass., USA) in 2 ml Dulbecco's Modified Eagle Medium (DMEM) containing 10% horse serum, 1% chick embryo extract, 2% L-glutamine, and 1% penicillin/streptomycin (Gibco, BRL, Grand Island, N.Y., USA). The plates were placed in a 37° C., 5% $CO_2$ incubator for several days. The cells emerging from these myofibers were grown until confluence, assayed for desmin expression, transduced with adenovirus carrying LacZ reporter gene expression, and tested for the myoblast survival post-implantation following the protocol described below.

An immortalized mdx cell line isolated from a transgenic animal carrying a thermolabile SV40 T antigen under the control of an inducible promoter was used (J. E. Morgan et al., 1994, *Develop. Biology* 162:486-498). The immortalized mdx cell line proliferated indefinitely under the permissive conditions of 33° C. with gamma interferon (proliferation medium; DMEM+20% fetal bovine serum) and underwent normal differentiation at 37°-39° C. without gamma interferon (fusion medium; DMEM+2% fetal bovine serum). This myoblast cell line was assayed for desmin immunoreactivity and the ability to differentiate when cultivated in a fusion medium. Subsequently, these cells were transduced with adenovirus carrying LacZ reporter gene expression, and the survival of the injected myoblasts was analyzed as described below.

Myoblasts were engineered to express anti-inflammatory agents. The mdx myoblast cell line was used for the genetic engineering of myoblasts expressing anti-inflammatory substances. The myoblasts were infected with a retroviral vector carrying the gene encoding interleukin-1 receptor antagonist protein (IL-1Ra) and a neomycin-resistance gene (G. Bandara et al., 1993, *Proc. Natl. Acad. Sci. USA*, 90:10764-10768). Following infection, the myoblasts were selected using neomycin (1000 µg/ml of medium) to obtain nearly 100% infected cells, because non-infected cells die when subjected to neomycin treatment.

The selected myoblasts were first analyzed in vitro for their ability to express IL-1Ra (80 ng/1×$10^6$ cells at 48 hours post-infection). The engineered myoblasts were found to be capable of differentiating into myotubes in vitro and of forming myofibers following intramuscular transplantation in vivo. The modified myoblasts were subsequently infected with adenovirus carrying the LacZ reporter gene and injected into mdx muscle. The early fate of the injected cells was monitored and compared with that of non-engineered cells using the protocol described below.

Immunohistochemistry for desmin: The different myoblast populations were fixed with methanol at −20° C. for 1 minute, followed by 2 rinses in phosphate buffer saline (PBS). The cell cultures were blocked with 10% horse serum for 1 hour and incubated with the first antibody (1/200 monoclonal mouse anti-desmin, Sigma Co., St. Louis, Mo., USA) for 1 hour. Following 3 rinses in PBS, the sections were incubated with a second antibody (anti-mouse conjugated to Cy3, immunofluorescence, 1/200, Sigma Co., St. Louis, Mo., USA). The immunostaining was then visualized by fluorescent microscopy and the number of desmin positive cells was computed and compared among the different groups.

Different populations of myoblasts were used for these experiments. 0.5 to 1×$10^6$ cells were injected percutaneously into the mid-portion of the gastrocnemius muscle for each experimental group; the experimental groups that were compared together received the exact same number of cells. Primary mdx myoblasts, myoblasts isolated from single muscle fibers, and immortalized mdx myoblast cultures were transduced with an adenovirus carrying the LacZ reporter gene using a multiplicity of infection of 50 (MOI=50). Forty-eight hours post-transduction, the different groups of transduced myoblasts were harvested by trypsinization (0.1% trypsin), washed in Hank's Balanced Salt Solution (HBSS), and intra-muscularly injected with a Drummond syringe. At different time points post-injection (0.5, 12, 24, 48 hours, and 5 days), the animals were sacrificed and the injected muscles were assayed for LacZ expression (histochemistry and ONPG). The β-galactosidase expression obtained from the injected muscles was compared with that of the transduced cell extract before transplantation (0 hours post-injection). Five two-month-old C57BL10/J mdx/mdx mice were used for each group. The experiment animals were kept in the Rangos Research Center Animal Facility of Children's Hospital of Pittsburgh. The policies and procedures of the animal laboratory were in accordance with those detailed in the guide for the "Care and Use of Laboratory Animals" published by the USA Department of Health and Human Services.

LacZ staining by histochemical technique: Cryostat sections of the injected and control muscles were stained for LacZ expression using the technique described as follows: sections were fixed with 1.5% glutaraldehyde (Sigma Co., St. Louis, Mo., USA) for one minute and rinsed twice in phosphate-buffered saline (PBS) and incubated in X-gal substrate [0.4 mg/ml 5-bromo-chloro-3-indolyl-β-D-galactoside (Boehringer-Mannheim, Indianapolis, Ind., USA), 1 mM $MgCl_2$, 5 mM $K_4Fe(CN)_6$/5 mm $K_3Fe(CN)_6$ in PBS] overnight (37° C.). Following the LacZ histochemistry, the muscle sections were counterstained with hematoxylin/eosin and visualized by light microscopy (Nikon, Optiphot. microscope).

β-galactosidase activity was assayed in order to achieve a better quantification and comparison of the transgene expression level in the infected cells and the injected muscles (J. Sambrook et al., 1989, *Molecular Cloning. A Laboratory Manual*, 1.21-1.52.). The injected muscles or cells were frozen in liquid nitrogen and homogenized in 0.25 M Tris-HCL (pH 7.8), and the homogenates were centrifuged at 3,500×g for 5 minutes. The muscle homogenate was disrupted by 3 cycles of freeze/thaw, and the supernatant was centrifuged (12,000×g/5 min. at 4° C.) and transferred to a microcentrifuge tube. 30 µl of this extract was mixed with 66 µl of 4 mg/ml ONPG (O-nitrophenyl-β-D-galactopyranoside, Sigma Co.) dissolved in 0.1 M sodium phosphate (pH 7.5), 3 µl of 4.5 M β-mercaptoethanol dissolved in 0.1 M $MgCl_2$, and 201 µl 0.1 M sodium phosphate. The mixture was then incubated at 37° C. for 30 minutes. The reaction was stopped by adding 500 µl of 1 M $Na_2CO_3$ and the optical density was read on a spectrophotometer at a wavelength of 420 nm. The level of β-galactosidase activity (# of units/sample) was extrapolated on a calibration curve, which converted the optical density at 420 nm to the concentration of β-galactosidase enzyme. The level of β-galactosidase enzyme was compared in the transduced non-injected myoblasts with that obtained in the injected muscle at 0.5, 12, 24, and 48 hours and at 5 days post-injection.

Immunochemical staining for myosin heavy chain (MyHC) isoforms: One monoclonal antibody specific for slow myosin heavy chain isoforms was used. The anti-slow myosin heavy chain (M 8421, Sigma Co., St. Louis, Mo., USA) monoclonal reacts with the slow MyHC of adult skeletal muscle. MyHC staining was performed using indirect immunoperoxidase techniques. 10 μm serial cryostat sections were collected on glass slides, fixed with cold acetone (−20° C.) for 1 minute and blocked with 5% horse serum for 1 hour. The sections were incubated overnight at room temperature in a humid chamber with primary antibodies diluted 1:500 in PBS, pH 7.4, containing 4% horse serum. The muscle cryostat sections were subsequently rinsed 3 times in PBS and incubated with sheep anti-mouse antibodies conjugated with horseradish peroxidase (A7282, Sigma Co., St. Louis, Mo., USA), diluted 1:100 in PBS for 90 minutes. After three rinses in PBS, the peroxidase activity was then determined by incubation with 1 mg/ml diamino-benzidine in PBS containing 0.01% hydrogen peroxide. The peroxidase reaction was then carried out and was stopped by repeated rinses in PBS. Sections were mounted in GelMount (Biomeda, Corp. Foster City, Calif.) and observed under light microscopy (Nikon Optiphot microscope). The co-localization of the LacZ and slow myosin heavy chain-expressing muscle fibers was then performed on serial muscle sections.

Statistical analysis: The average transduction level was computed at different time points for each group (n=5) and compared over time by one-factor analysis of variance (ANOVA; multi-comparison type factorial) using statistical software (Stat View 512$^+$; Brain power, Calabasas, Calif., USA).

In this example, it was demonstrated that different populations of primary muscle-derived cells isolated from gastrocnemius muscle from different preplates contain a different percentage of desmin positive cells. The different populations of cells consisted of a mixture of muscle-derived cells including myoblasts, fibroblasts, and adipocytes. The populations of muscle-derived cells were found to display different desmin immunoreactivities, ranging from between 7 to 80% after preplating. For example, the first preplate contained 7% desmin positive cells, while the sequential preplates were enriched in their content of desmin positive cells (i.e., PP#2=14%, PP#3=25%, PP#4=72%, PP#5=77%, and PP#6=80%).

These cell populations had variable ability to differentiate into myotubes when cultivated into a fusion medium. In fact, the number of myotubes obtained in preplate #1 and preplate #3 was very low compared with those obtained in preplate #5 and preplate #6. The results demonstrate that populations of muscle-derived cells with higher numbers of desmin positive cells display a better ability to differentiate into myotubes.

97% of desmin positive cells were obtained from a single myofiber isolated from Extensor Digitorum Longus muscle (EDL). In addition, the mdx myoblast cell line, isolated from transgenic mice carrying the SV40 T antigen, was nearly 100% desmin positive. These cells were also capable of differentiating into myotubes, which demonstrates the high myogenicity index of those cell cultures.

Different populations of muscle derived cells isolated and purified from normal and mdx (dystrophic) mice by the preplate technique were tested for the presence of various markers. It was found that a population of muscle-derived cells had the following characteristics: about 95% desmin positive; about 95% BCL-2 positive; about 95% CD34 positive; about 95% myosin heavy chain isoforms (MyHCs) expression; about 30-60% MyoD expression; about 30-60% Myogenin expression; and less than about 10% M-cadherin expression, thereby suggesting their stem cell qualities.

Muscle-derived cells obtained from preplate #1 and injected into gastrocnemius muscle were rapidly lost by 48 hours post-injection: only 17% of the expression of the introduced gene present in the injected myoblasts was measured in the injected muscle. However, an improvement in the survival of the injected myoblasts was obtained with the use of cells from subsequent preplates for injection. In fact, the cells isolated from preplate #2 yielded a 55% myoblast loss at 48 hours post-injection, those from preplate #3 yielded a 12% myoblast loss, and those from preplate #6 yielded a 124% gain compared with the level of LacZ transgene expression present in the cells before injection and transplantation. (FIGS. 7A-7H). These results suggest that populations of muscle-derived cells were isolated during preplating that displayed a better survival rate following transplantation.

Surprisingly, the pure population of myoblasts obtained from the isolated myofibers (fiber myoblasts, Fmb) displaying over 95% desmin immunoreactivity suffered a rapid loss following myoblast transplantation. In fact, a loss of 96% of the injected myoblasts was observed at 48 hours post-transplantation. Similarly, the mdx myoblast cell line (Cell line), (FIGS. 7D and 7H) was rapidly lost following transplantation: 93% of the level of LacZ transgene expression present in the cell culture post-implantation disappeared after 2 days post-injection. These results show that the high percentage of desmin-positive cells present in the muscle-derived cell population in preplate #6 was but one factor to explain the improvement of cell survival post-implantation.

Even though populations of muscle-derived cells have been isolated displaying a better survival post-injection (PP#3, PP#6), all of the cell populations lead to a decrease in reporter gene expression between days 2 and 5 post-injection. The cells with the better survival rate, however, retained better transgene expression at day 5.

All of the myoblast populations following adenoviral transduction have been found to be capable of delivering the β-galactosidase reporter gene to skeletal muscle at 2 and 5 days post-infection. Using the same numbers of cells, it was observed that PP#6 and, to a lesser extent, PP#3 offered a better gene transfer than the population of muscle-derived cells isolated at preplates #1 and #2. The ability of the purified muscle cells to circumvent the poor survival of the injected cells may explain the better efficiency of gene transfer in the injected muscle. However, it was also observed that PP#6 displayed a better ability to fuse with host myofibers compared with muscle-derived cells isolated at earlier preplates. The myoblast cell line (Cell Line) and the highly pure myoblast culture isolated from myofibers (FMb) also displayed a reduction in gene transfer when compared with the muscle-derived cells isolated at preplate #6, suggesting that the ability of cells to bypass poor survival post-injection leads to an improvement of gene transfer to skeletal muscle.

Following injection of muscle cells, the cells either fused together to form myotubes or fused with host myoblasts and muscle fibers to form mosaic myofibers. Serial cryostat sections showed that transduced myoblasts obtained from isolated myofibers either fused together to form myotubes and immature myofibers expressing fast myosin heavy chains or fused with host myofibers expressing fast myosin heavy chains. This suggested that the myofibers used to isolate myoblasts were probably expressing fast myosin heavy chains. In contrast, the muscle-derived cells isolated at PP#6 fused together and with host myofibers expressing both fast and slow myosin heavy chains, suggesting that the muscle-derived cells at PP#6 have the ability to fuse with fast and slow myosin heavy chains myofibers.

Figure 7A:
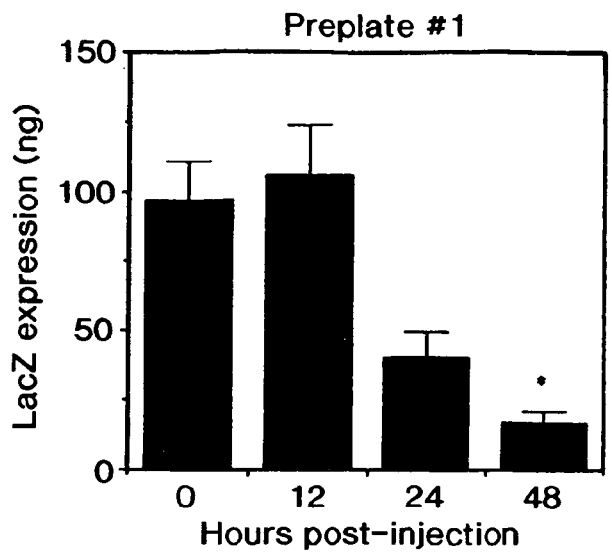
FIGS. 7A-7H depict the characterization of the survival of different populations of muscle-derived cells following transplantation in skeletal muscle. The injection of the muscle-derived cells obtained following preplate #1 was rapidly lost by 48 hours post-injection (FIG. 7A): only 17% of the LacZ transgene expression present in the injected myoblasts pre-injection was measured in the injected muscle. The cells isolated at preplate #2 (FIG. 7E) led to 55% myoblast loss; preplate #3 (FIG. 7B) a 12% loss; and preplate #6 (FIG. 7F) a 124% gain in the level of transgene expression present in the cells before transplantation. A 96% loss of the pure population of myoblasts isolated from myofibers was observed at 48 hours post-transplantation (Fiber myoblast, FMb, FIG. 7C). Similarly, the immortalized mdx myoblast cell line showed cell loss following transplantation: 93% of the level of transgene expression present in the cell culture post-implantation was seen 2 days post-injection (Mdx cell line, FIG. 7G). PP#3 and PP#6 (FIGS. 7D and 7H) displayed a better cell survival at 2 days post-injection, yet a decrease was observed in the amount of LacZ reporter gene in the injected muscle at 5 days post-injection. However, the cells which displayed a better survival (PP#3 and PP#6) remained with a higher level of gene transfer at 5 days post-injection. "*" indicates a significant difference (P<0.05) when compared with transduced non-injected myoblasts (0 hour).
Figure 7B:
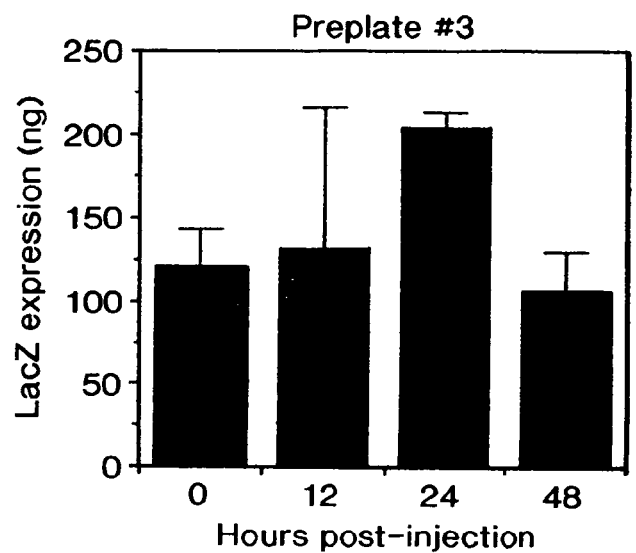
Figure 7C:
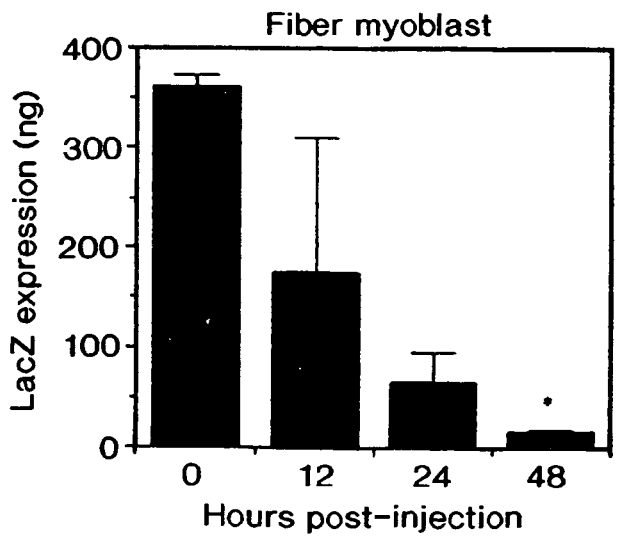
Figure 7D:
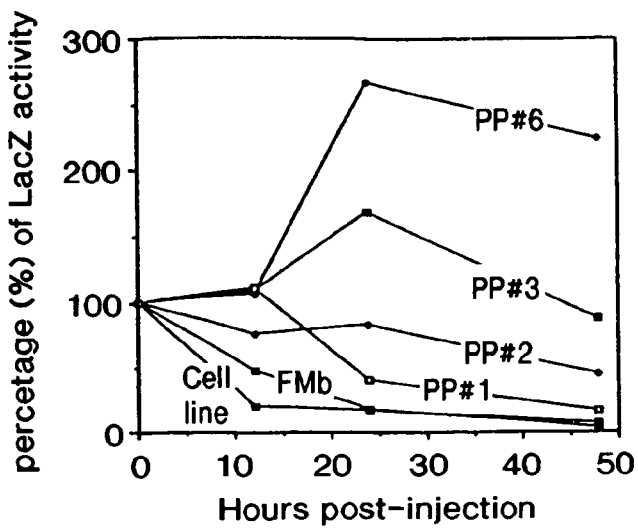
Figure 7E:
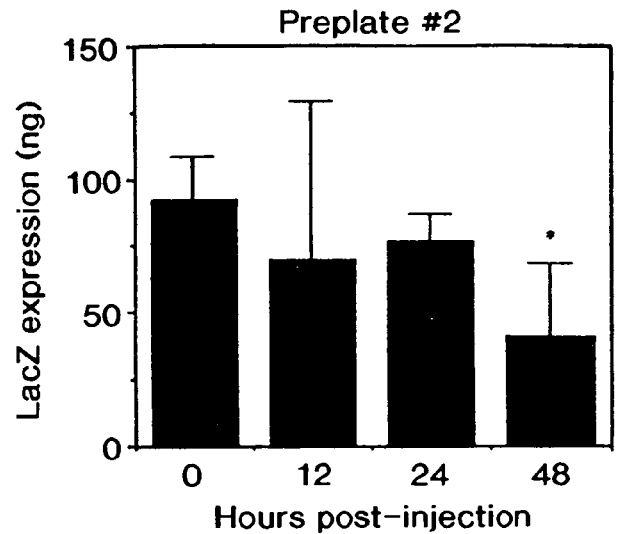
Figure 7F:
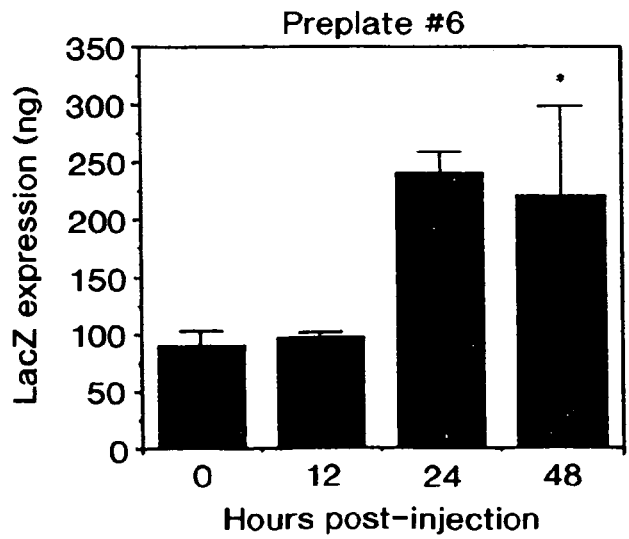
Figure 7G:
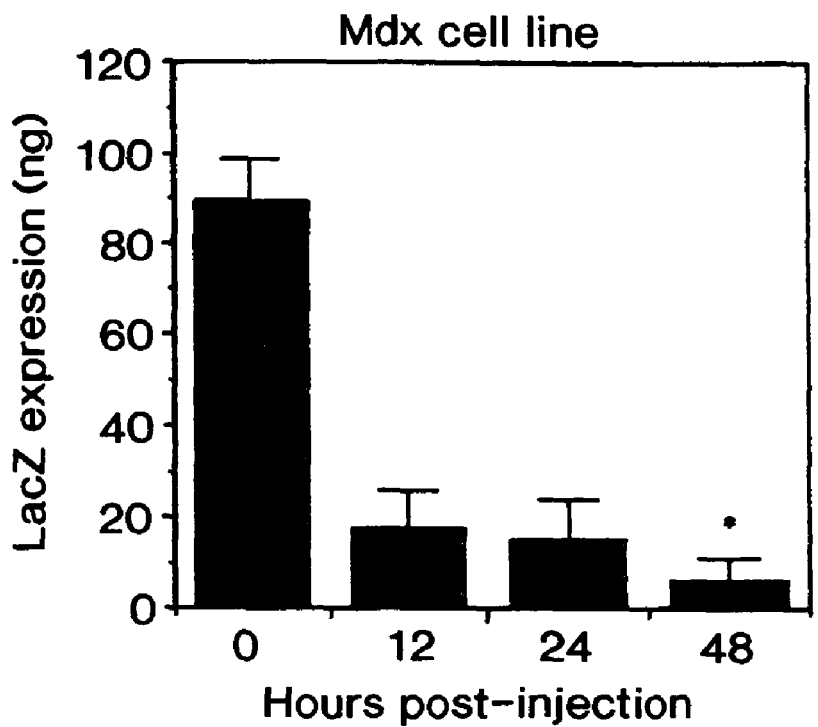
Figure 7H:
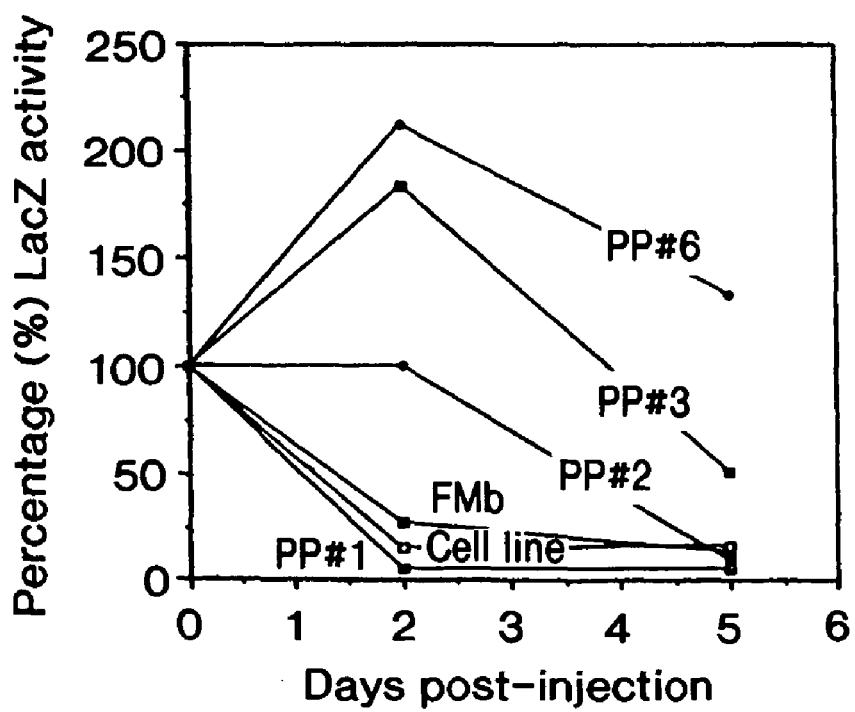

To investigate whether the cells capable of expressing anti-inflammatory substances can improve the cell survival post-injection, myoblasts were genetically engineered to express interleukin-1 receptor antagonist protein (IL-1 Ra), which is able to compete with inflammatory cytokine IL-1 for binding to the IL-1 receptor, but does not induce IL-1 receptor signalling. The survival of the engineered myoblasts was then compared with that of non-engineered control cells. The myoblast used for this experiment, the mdx cell line, displayed a drastic loss of the injected cells post-injection (FIG. 7G). An 84% loss of the non-engineered cells was observed by 48 hours post-injection through the significant decrease in the amount of β-galactosidase expression in comparison to the non-injected transduced myoblast at time 0. Moreover, a slight increase in the amount of reporter gene was detected at 120 hours post-injection, which remains significantly different from that observed in control cells (FIG. 8A).

In contrast, the cells engineered to express IL-1Ra, significantly reduced the early loss of the injected cells. A loss of 60% in the amount of β-galactosidase expressed in the non-injected cells ($P<0.05$) at 24 hours post-injection was seen, but, in contrast to the result observed with the non-engineered cells, the level of β-galactosidase expression detected at 2 days post-injection was not found to be significantly different than that found in the non-injected IL-1Ra-expressing myoblasts. This finding suggests that inflammation also plays a role in the poor survival rate of the injected cells; consequently, approaches capable of blocking the inflammation may aid in the development of strategies to achieve efficient myoblast transplantation (FIGS. 8B-8D).

The experiments in this example were performed to determine whether inflammation is the only factor involved in the poor survival of the injected myoblasts. The extremely wide range of biological activities of IL-1Ra may improve the cell survival by blocking the action of an inflammatory cytokine (IL-1). As described herein, myoblasts were genetically engineered to express anti-inflammatory IL-1Ra, and were tested for the prevention of rapid loss of the injected cells. The engineered myoblasts expressing IL-1Ra allowed for a better survival rate of the injected myoblasts at 48 hours post-injection. The non-engineered myoblast cell line displayed poor survival of the injected cells, but the same cell line expressing IL-1Ra significantly improved the survival rate of the injected cells.

An 80% improvement in the survival of the injected cells was observed by the local expression of an anti-inflammatory substance. There was a significant decrease in the amount of the β-galactosidase reporter gene at 24 hours compared with the non-injected control cells, suggesting that IL-1Ra expressing myoblasts probably fused between 24 and 48 hours post-injection and led to an increase of the expression of β-galactosidase reporter gene. A slight decrease in the amount of β-galactosidase reporter gene expression was observed at 5 days post-injection which may be related to immune rejection.

A substantial reduction in the loss of the injected myoblasts was achieved with the IL-1Ra-expressing cells, but a 20% loss was still observed at 48 hours post-injection. Thus, inflammation is likely to be only one factor involved in the rather rapid loss of injected myoblasts post-implantation.

Different populations of muscle-derived cells were evaluated to assist in the development of approaches to circumvent the poor survival of injected myoblasts post-transplantation. To carry out this evaluation, mdx myoblast cell lines, pure myoblasts isolated from myofibers, and primary muscle-derived cells at different purities were injected into adult mdx muscle. The myoblasts were adenovirally transduced as described, and the early fate of the injected cells post-injection was evaluated at different time points post-injection (i.e., 0.5, 12, 24, 48 hours, and 5 days). It was observed that populations of primary muscle-derived cell cultures isolated from a gastrocnemius muscle displayed a differential ability to express desmin and differentiate into myotubes. In addition, the cell survival post-injection was different. In fact, the same number of muscle cells derived from preplate #1 versus preplate #6 resulted in an 83% loss and a 124% gain, respectively, in the transgene expression, compared with non-injected transduced cells at time 0. This suggests that the isolation of specific populations of muscle-derived cells totally overcomes the rapid lost of the injected cells.

This example evaluated whether the source of muscle-derived cells could have a primordial role in the early survival of the injected myoblasts. A great difference in the content of satellite cells has already been observed between slow and fast twitch muscles (H. Schmalbruch and U. Hellhammer, 1977, *Anat. Rec.*, 189:169; A. M. Kelly, 1978, *Dev. Biol.*, 65:1; M. C. Gibson and E. Schultz, 1982, *Anat. Rec.*, 202: 329). The types of satellite cells isolated from these muscles may possibly display a differential fate post-transplantation.

The PP#6 muscle-derived cells were found to have the ability to fuse with myofibers expressing both slow and fast myosin isoforms, in contrast to myoblasts obtained from isolated myofibers, which either fused together or fused with myofibers expressing the fast myosin isoform. The inability of myoblasts obtained from isolated myofibers to fuse with myofibers expressing the slow myosin isoform may be involved in the differential survival of the injected myoblasts, since the injected muscle (gastrocnemius) contains a mixture of myofibers expressing fast and slow myosin isoforms. The injected myoblasts that are unable to fuse with host myofibers will likely die at the injection site. Without wishing to be bound by theory, this may explain why the myoblast cell line displaying a high desmin immunoreactivity still shows a poor survival post-injection.

Even though different populations of muscle-derived cells and the IL-1Ra expressing myoblasts display a better survival post-implantation in skeletal muscle, the long-term persistence of the injected cells appears to be hindered by immune responses. In general, all populations of muscle cells display a reduction in the amount of β-galactosidase expression between day 2 and 5 post-injection. It was also found that the number of LacZ-expressing myofibers decreased over time in the injected muscle, even when IL-1Ra expressing myoblasts were used. Consequently, the engineering of specific populations of muscle-derived cells not only to express IL-1Ra, but also to express additional immune suppression factors or agents could likely prevent both poor survival and any adverse immune responses that may accompany myoblast transfer.

Example 6

Experiments were performed to determine the feasibility of cell mediated gene therapy using myoblasts transduced by an adenovirus vector carrying the gene encoding basic fibroblastic growth factor (bFGF). bFGF engineered myoblasts were injected into the urethra to treat stress incontinence and also into the bladder wall to improve detrusor contractility. Adenoviral vectors used were produced as described by H. Ueno et al., 1997, *Arteriosclerosis, Thrombosis & Vascular Biology*, 17(11):2453-60 and J. C. Takahashi et al., 1997, *Atherosclerosis*, 132(2): 199-205.

Experiments similar to those described for urethra and bladder injection in Examples 2 and 3 were performed to compare sham control animals versus animals injected with myoblasts transduced with adenovirus vectors genetically engineered to contain the bFGF gene; the transduced myoblasts expressed bFGF protein following transduction.

Briefly as described, four groups of animals were assessed: control bladder and control urethra animals with myoblastbFGF or sham saline injection. Approximately 8 animals were evaluated in each group. The animals were sacrificed 4 days after injection. Animals which had received urethral injection underwent physiological assessment as described in Example 2. Animals which had received bladder injection underwent physiological assessment as described in Example 3.

In these experiments, myoblasts were transduced with an adenovirus vector carrying both the bFGF gene and a β-galactosidase reporter gene, described above, and were also labeled with fluorescent latex microspheres (FLMs) (P. Cuevas et al., 1996, *Proc. Natl. Acad. Sci. USA*, 93:11196-12001; Y. Nakahara et al., 1996, *Cell Transpl.*, 5:191-204). Histochemical staining for bFGF, lacZ and fluorescent microscopic analysis was performed to evaluate and quantify the survival and differentiation of myoblasts and to assess the generation of myofibers.

Example 7

The experiments described in this Example demonstrate that myoblasts infected with an adenovirus vector carrying the iNOS gene and injected locally into the urethra and bladder decrease bladder inflammation, improve urethral relaxation, and affect erectile dysfunction.

Briefly, and in accordance with the present invention, myoblasts were infected with adenovirus engineered to carry the iNOS gene (Example 1). The transduced myoblasts were injected into either the urethra or bladder of S.D. rats. Physiological experiments as described in Examples 2 and 3 for the bladder and urethra were performed to assess the physiological effect(s) of iNOS gene therapy in these tissues.

The cyclophosphamide (CYP) model was employed for bladder inflammation and a partial urethral ligation model was employed for partial urethral obstruction. For the CYP bladder inflammation model, 4 groups of animals were assessed: control and CYP animals received myoblast-iNOS or sham saline bladder injections. Approximately 8 animals comprised each group. CYP injection (100 mg/kg i.p.) was performed at the same time as myoblast-iNOS or sham injection. The animals were sacrificed 4 days after the injections, based on determinations of persistent bladder inflammation beyond 4 days after CYP, and optimal iNOS expression at 4 days (E. Tzeng et al., 1995, *Proc. Natl. Acad. Sci. USA*, 92:11771-11775; E. Tzeng et al., 1996, *I. Surgery*, 120:315-321).

For the urethral obstruction model, 4 groups of animals were also studied: control and urethral ligation animals with myoblast-iNOS or sham saline urethral injection. Myoblasts were transduced with an adenovirus vector carrying the β-galactosidase reporter gene and were labeled with fluorescent latex microspheres (FLMs). Histochemical staining for lacZ and fluorescent microscopic analysis were performed to evaluate and quantify the survival and differentiation of myoblasts and to assess myofiber development. Immunohistochemistry staining for iNOS and for adenovirus proteins was performed in all specimens. Northern blot analysis for human iNOS RNA production was assessed in gene-transfected animals and in the appropriate controls.

Experiments and the results thereof related to intraurethral and intravesicle NO production are presented more specifically below:

A. Intraurethral NO Donors Relax Urethral Smooth Muscle

To first assess the role of NO donors on smooth muscle, urethral perfusion pressure and isovolumetric bladder pressure were measured with catheters inserted through the bladder dome in urethane anesthetized female S.D. rats (250-300 grams), (n=9). The catheter assembly was wedged in the bladder neck to block passage of fluid between the bladder and urethra without affecting the nerve supply to the organs. The external urethra was not catheterized. Responses were examined in the control state at an urethral saline infusion speed of 0.075 ml/min. After blocking striated urethral sphincter with intravenous alpha-bungarotoxin administration (100 mcg/kg), intraurethral drugs were administered.

The results of these experiments revealed that the urethra exhibited reflex responses characterized by an initial decrease in urethral pressure at the onset of reflex bladder contractions. This was followed by a period of high frequency oscillations which was abolished by alpha-bungarotoxin. Intraurethral infusion of NO donors, (i.e., S-nitroso-N-acetylpenicillamine [SNAP] (2 mM) and nitroprusside (1 mM)), immediately decreased baseline urethral pressure by 30% to 37% and maximum urethral relaxation by 24% to 50%. In addition, the duration of reflex urethral relaxation was increased by 96% to 100%, which was likely to be due to exogenous NO potentiating endogenous NO relaxation. Neither NO donor changed the amplitude of bladder contraction. The urethral relaxation persisted for 15 minutes after stopping the infusion of NO donors. Intraurethral NO donors did not affect the mean blood pressure. Intraurethral N-nitro-L-arginine (L-NAME) (20 mM) only partially blocked the endogenous NO reflex relaxation.

The results of these experiments demonstrate that NO plays a key role in reflex urethral smooth muscle relaxation during micturition. Topical intraurethral NO donors rapidly induced urethral relaxation without affecting the bladder. On the basis of these results, intraurethral application of NO donors can be clinically effective in cases of urethral smooth muscle sphincter spasticity and obstruction.

B. Intravesical NO on Cyclophosphamide-Induced Cystitis

To first assess the role of intravesicle NO on cyclophosphamide-induced cystitis, female S.D. rats received a single intraperitoneal injection of CYP (100 mg/kg) or vehicle. Voiding parameters (mean voided volume and number of voids) were then monitored for 24 hours in a metabolic cage. Forty-eight hours after CYP injection, bladder function was studied using continuous saline infusion (0.04 ml/min) cystometry via PE-50 transurethral catheter under urethane anesthesia. The NO donors S-Nitroso-N-acetyl-penicillamine (SNAP) (2 mM) and sodium-nitroprusside (SNP) (1 mM), as well as the NOS inhibitor N-nitro-L-arginine methyl ester (L-NAME) (20 mM), were administered intravesically.

The results showed that the number of micturitions during the 24 hours after CYP injection was significantly greater for 24 hours (117±86, n=8) than for control rats (25±4, n=4) ($p<0.001$). After 7 days, the voiding frequency was still persistently elevated (38±4, n=4) ($p<0.05$). There was no difference in total micturition volume between CYP treated (20.5±9.2 ml) and control rats (15.2±6.1 ml). Infusion of an NO donor (SNAP: n=5 or SNP: n=3) increased the intercontraction interval (ICI) (64%), but did not change the amplitude of bladder contractions. Treatment of L-NAME (n=8) did not alter ICI or amplitude (Table 3).

In addition, the CYP injected rats were monitored for over 7 days and demonstrated persistently elevated voiding frequency, consistent with bladder irritation.

TABLE 3

|  | ICI (min) | Amplitude (cmH$_2$O) | Contraction duration (min) |
|---|---|---|---|
| Saline | 4.4 ± 2.3 | 23 ± 8 | 1.1 ± 0.3 |
| L-NAME | 3.8 ± 2.0 | 21 ± 6 | 1.0 ± 0.4 |
| NO donor | 7.2 ± 4.6* | 21 ± 5 | 1.2 ± 0.3 |

*Infusion of NO versus saline and L-NAME: p < 0.01 (Paired t-test)

The foregoing experiments demonstrated that CYP caused long-term bladder irritation and that intravesical NO donors acutely and effectively reversed the CYP-induced bladder activity. Without wishing to be bound by theory, it is hypothesized that this drug effect is not due to a smooth muscle relaxation, but rather is mediated by a change in afferent nerve excitability which increases the intercontraction interval, but does not change contraction amplitude. Topical NO donors may be considered as a treatment for cyclophosphamide and other inflammatory mediated cystitis.

C. Myoblast mediated iNOS gene therapy in the (genito) urinary system

Experiments were then performed to demonstrate that iNOS gene therapy according to the present invention is advantageous and efficacious for therapeutic use in the genitourinary system.

1. iNOS Gene Therapy for Erectile Dysfunction: Comparison Among Plasmid, Adenovirus and Adenovirus Transduced Myoblast Vectors The gene encoding the inducible form of NOS (iNOS) was inserted into a plasmid and into an adenovirus vector. The iNOS plasmid was as described in D. K. Nakayama et al., 1992, *Am. J. Respir. Cell. Mol. Biol.*, 7:471-476. The adenovirus iNOS vector was as described in D. A. Geller et al., 1993, *Proc. Natl. Acad Sci USA*, 90:3491-3495 and in U.S. Pat. Nos. 5,658,565 and 5,468,630. By injecting a solution of either plasmid, virus, or virally transduced myoblasts, exogenous human iNOS was introduced into the rat penis.

Adult male rat penis was injected with myoblasts transfected with adenovirus vectors carrying the β-galactosidase gene. After 2, 4 and 7 days, X-gal staining and the physiological effects of X-gal were assessed. 100 μl injections of adenovirus with titers of $10^6$-$10^9$ were tested. Myoblasts were plated at a density of $5 \times 10^4$ cells per well and were transduced with adenovirus stock (MOI=50). Injections ranged from $1.33 \times 10^5$ to $1 \times 10^6$ cells per 100 μl. Basal intracavernous pressure (ICP) and maximal ICP after cavernous nerve stimulation were measured. iNOS immunohistochemistry and PCR of human iNOS primer were also performed. For plasmid experiments, 100 μg of plasmid injected in 100 μl of 20% sucrose/PBS was used for injection into the bladder, penis and urethra.

Optimal conditions for gene transfection were determined by varying the number of virus particles (pfu), concentration, volume and vehicle of the injected solution. The level of iNOS or reporter gene expression was time dependent. Maximal expression was found at day 4, with lower levels at day 2 and minimal levels at day 7. At day 4, gene expression was greatest for myoblast+adenovirus>adenovirus>plasmid. Immunohistochemical staining of iNOS and adenovirus proteins was detected in treated penis. Northern blot analysis for human iNOS was positive only in gene-transfected animals. There was no difference in basal or maximal ICP between control and animals treated with the β-galactosidase reporter gene. However, there was a significant increase in basal ICP (55±23 cmH$_2$O) in gene treated penis versus control (5±6 cmH$_2$O). Maximal ICP increased two fold in iNOS transfected rats.

The results demonstrated that myoblast mediated gene therapy was more successful in delivering iNOS into the penis than was direct virus or plasmid transfection methods. NOS gene therapy according to the present invention thus promises to provide a new treatment for erectile dysfunction.

2. Measurement of iNOS Gene Therapy

The release of NO was confirmed using a porphyrinic microsensor placed directly in tissues treated with inducible NOS (iNOS) gene therapy (L. A. Birder et al., 1998, *American Urological Association Meeting*, 1998). Ex vivo gene transfer was used to place the human iNOS gene into the penis and bladder of male S.D. rats. Injections of 100 μl of infected myoblasts suspended in saline solution at a total cell count of $1.33 \times 10^5$ to $1 \times 10^6$ cells per injection were injected into the corpora cavernosum of the rat. The bladder was injected with a similar solution; however, the cell concentration ranged from $1.33 \times 10^5$ to $1 \times 10^6$ cells per 10 μl injection. Transduced myoblasts were prepared by incubating them for 24 hours with adenovirus vector containing the iNOS gene at a multiplicity of infection of 50 virus particles per cell. Immunohistochemical staining was performed on the cultured cells to ensure adequate infection and iNOS protein production.

NO release in the bladder and penis was measured by placing the tip of a Naflon-coated porphyrinic microsensor (dia. 10 μM; detection limit, 5 nM; response time, 1 ms) directly on the bladder surface (mucosal and serosal) and on the corporal cavernosum, respectively. The NO release peak concentration of 1-1.3 μM was evoked by the adrenergic agonist, norepinephrine (3 μM) and also by the iNOS cofactor, tetrahydrobiopterin (TBH4).

Incorporation of the iNOS gene into the penis and bladder was detected by positive immunohistochemical staining for iNOS and adenovirus antibodies, and Northern blot analysis for human iNOS RNA production was positive only in human iNOS gene transfected animals. The porphyrinic microsensor measured low but similar levels of constitutive NO release in various areas of the bladder. The addition of 100 μM TBH4 caused a brief (<5 second) spike in NO release (1-5 nM) in control areas of the bladder.

In iNOS gene injected areas, there was a sustained release (>1 min.) of large amounts of NO (>20 nM). The porphyrinic microsensor demonstrated increased NO release in areas of the bladder treated with myoblast cell mediated iNOS gene therapy.

Example 8

The use of co-factors such as trophic factors, i.e., cytokines, expressed by myoblasts genetically engineered to contain genes encoding such factors is a beneficial aspect of the present invention.

Muscle-related injuries are a challenging problem in many fields of medicine. Even though muscles retain their ability to regenerate following injury, the healing process of muscles following such injuries has been found to be very slow and often leads to an incomplete muscle recovery. To develop approaches to improve muscle healing following injury, e.g., bladder or urethral wall injury (cryoinjury), the present inventors have developed reproducible injury models for muscle contusion, strain, and laceration.

Investigations related to the present invention have shown that muscle regeneration occurs following the above-mentioned injuries, but that the development of scar tissue formation greatly limits the natural healing process. Thus, it was newly determined that an enhancement of muscle growth and regeneration could be used to improve muscle healing following injuries. Accordingly, growth factors were identified which enhanced not only myoblast proliferation and differentiation in vitro, but also muscle regeneration in injured muscles which improved muscle healing following injuries. These findings can also have direct application in cases of lower urinary tract smooth muscle injury associated with stress urinary incontinence and impaired bladder contractility.

A. Development of Animal Models for Muscle Injury

The characterization of approaches to improve muscle healing following injuries required the development of well-defined, reproducible orthopaedic muscle injury models, including contusions, lacerations, and strains as described herein. The characterization of muscle regeneration following these injuries allowed the determination of the muscle's natural healing following injury. The muscle laceration, contusion, and strain models were developed in mice.

Briefly, the muscle laceration was performed by cutting the gastrocnemius muscle of a mouse with scissors at 60% of its length from its distal insertion, 75% of its width, and 50% of its thickness. The muscle contusion was made by dropping a 16 gram ball through an impactor from a height of 100 centimeters onto the mouse's gastrocnemius muscle, and the muscle strain was performed by elongating the muscle-tendon unit to a pre-determined strain point at the rate of 1 cm/min.

In order to evaluate muscle healing following injury, histological staining (hematoxylin-eosin) in conjunction with immunohistochemical techniques were employed to assess the expression of desmin and vimentin. Since desmin is a cytoskeletal protein uniformly expressed in regenerating myofibers, it has been used to specifically locate regenerating myofibers. Vimentin is expressed in mononucleated fibrocytes and macrophages and has been used herein as a marker for fibrosis.

It was observed that the injured muscle was capable of healing due to a massive muscle regeneration which occurred following injury. The high level of muscle myofiber regeneration seen at 7 and 10 days following injury began to decrease after about 14 days and continued to decrease until 35 days post-trauma. The development of a large scar tissue formation in the injured muscle revealed that the muscle healing was not completed at 35 days post-injury. In fact, it was observed that the development of the scar tissue formation started at 14 days post-injury and increased gradually until 35 days. It is likely that the development of fibrosis, which appears to hinder the healing process, can be related to the reduction of muscle regeneration which is also observed at 14 days post-injury.

B. Characterization of the Effects of Several Growth Factors on Myoblast Proliferation and Fusion In Vitro In approach for improving muscle healing following injury is to accelerate muscle regeneration. One way to achieve this acceleration is by increasing the myogenic activity of muscle cells in the injured muscle. Substances which enhance myoblast proliferation and differentiation in vitro may also increase muscle regeneration in vivo and prevent the development of scar tissue formation.

During muscle regeneration, numerous growth factors are released by the injured muscle to modulate muscle regeneration. These proteins activate the satellite cells to proliferate and differentiate into myofibers to support muscle regeneration (E. Schultz, 1989, *Med. Sci. Sports Exer.*, 21:181; T. Hurme and H. Kalimo, 1992, *Med. Sci. Sports Exer.*, 24:197-205; R. Bischoff, The satellite cell and muscle regeneration. *Myology.* 2nd Edition. New York, McGraw-Hill, Inc, pp. 97-118, 1994). During growth and development of skeletal muscle, many growth substances have been found to be capable of inducing various responses from the skeletal muscle. In fact, the individual effects of these growth factors on specific steps of muscle regeneration have been shown (R. L. Chambers and J. C. McDermott, 1996, *Can. J. Appl. Physiol.*, 21:155-184; J. R. Florini and K. Magri, 1989, *Am. J. Physiol.*, 256:701-711; M. D. Ground, 1991, *Path. Res. Pract.*, 187:1-22).

Several growth factors, including acidic and basic fibroblast growth factors (aFGF and bFGF); epidermal growth factor (EGF); insulin-like growth factor-1 (IGF-1); platelet derived growth factor (PDGF); transforming growth factor β or α (TGF-β or TGF-α); and nerve growth factor (NGF) have been investigated for their ability to enhance the myogenic activity of muscle cells in vitro. Myoblasts were cultured with these trophic factors at different concentrations (1, 10 and 100 ng/ml), and the myoblast proliferation and differentiation were monitored at 48 and 96 hours post-incubation. The findings herein revealed that b-FGF, IGF-1 and NGF each significantly enhanced myoblast proliferation in vitro.

Further, bFGF, aFGF, IGF-1, and NGF were found to be able to increase myoblast differentiation into myotubules (Table 4). Other growth factors were incapable of significantly increasing either myoblast proliferation or differentiation. These results showed that bFGF, NGF, and IGF-1 significantly enhanced myoblast proliferation, while b-FGF, a-FGF IGF-1 and NGF increased myoblast differentiation into myotubules. Thus, these factors afford beneficial results when delivered into an injured muscle to improve muscle healing following injury in accordance with the present invention (Table 5).

TABLE 4

| Effect of Growth Factors on Myoblasts in vitro | Proliferation | Fusion |
|---|---|---|
| b-FGF, IGF, NGF | Stimulate | Stimulate |
| a-FGF | Inhibit | Stimulate |
| PDGF, EGF, TGF-α, TGF-β | Inhibit | Inhibit |

C. Direct and Ex Vivo Gene Transfer of Selected Trophic Factors

The technique chosen to deliver prospective growth factors to injured muscle is of paramount importance to optimize therapeutic benefit. Options include direct injection of growth factors, direct gene therapy, ex vivo gene therapy, and myoblast transplantation.

Ex vivo delivery of the β-galactosidase marker gene to injured muscle produces many β-galactosidase positive myofibers. The ex vivo muscle cell-mediated approach provides not only an efficient method of delivering selected genes, but also provides cells capable of participating in the reparative process, similar to myoblast transplantation. However, myoblast transplantation lacks in vitro genetic manipulations. In addition to its application toward inherited muscle diseases, myoblast transplantation is shown to improve myofiber regeneration in muscle experimentally injured with myonecrotic agents. Therefore, the closely related techniques of muscle cell-mediated ex vivo gene therapy and myoblast transplantation are both applicable to muscle injuries.

Individual direct injections of b-FGF, IGF-1, and NGF into injured muscle (e.g., laceration, contusion, and strain) can increase the number of regenerating myofibers in vivo and increase both muscle twitch and tetanic strength 15 days after injury. However, secondary to rapid clearance and short half-lives, the effect of direct growth factor injections is likely transient and suboptimal, due to the rapid clearance of the product from the injured sites and the short half life of these proteins. By contrast, persistent gene expression through cell mediated gene therapy in accordance with the present invention can further improve muscle healing following injuries. The engineering of vectors capable of expressing these growth factors opens new avenues of treatment for injured muscles. Also in accordance with the present invention, gene therapy based on direct and ex vivo gene transfer is capable of delivering a gene (e.g., a marker gene) in the injured muscle (i.e., laceration, contusion, or strain).

Direct gene therapy to deliver genes to skeletal muscle is possible using naked DNA retrovirus, adenovirus, herpes simplex virus and adeno-associated virus. Most of these vectors transduce relatively few adult myofibers. However, adenovirus is capable of transducing a large number of regenerating muscle fibers, a condition present in injured muscle.

Direct injection of adenovirus containing the beta-galactosidase marker gene into lacerated, contused, and strained muscle results in many transduced myofibers at 5 days. Moreover, direct injection of adenovirus carrying growth factor genes (i.e. bFGF, IGF-1, NGF) should result in sustained protein production in injured muscle. Direct injection of adeno-associated virus (AAV) results in a high level of adult myofiber transduction in both injured and non-injured muscle. AAV may be the preferred vector for direct gene delivery to mature skeletal muscle, although it is capable of carrying genes of only 1-4 KB pairs.

Figure 12:
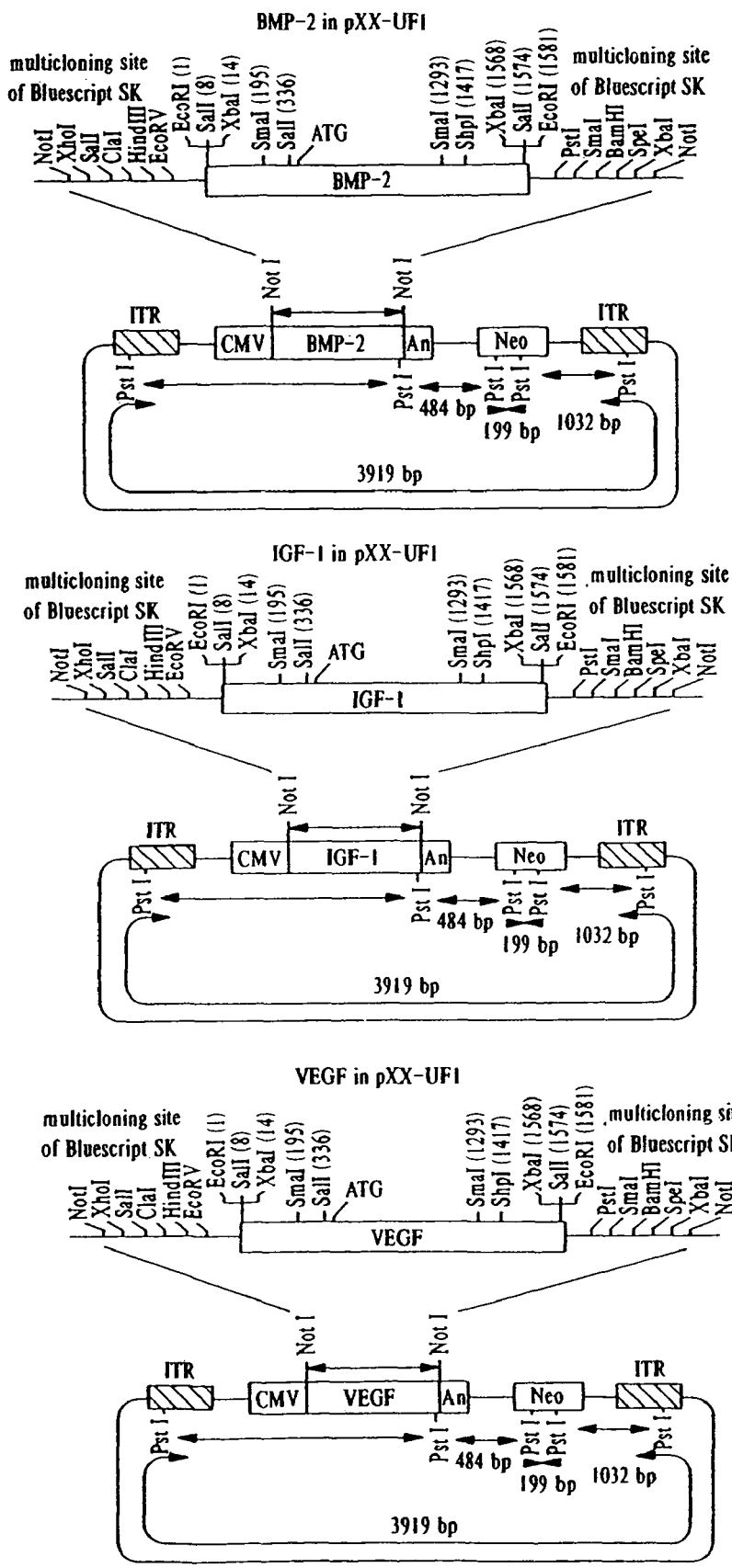
FIG. 12 shows a schematic representation of the construction of a shuttle plasmid to construct an adeno-associated virus to carry the expression of IGF-1 (muscle injuries), VEGF (bone and cartilage healing), and BMP-2 (bone and cartilage healing). This shuttle plasmid, designated pXX-UF1, is used to construct an adeno-associated virus.

According to the practice of the present invention, the injection of engineered muscle-derived cells expressing IGF-1 was capable of improving muscle healing following laceration injury when intramuscularly injected at the injured site. The injected muscle with muscle-derived cells expressing IGF-1 displayed a higher fast twitch and tetanic strength than the injured muscle treated with saline. These results suggest that the injection of muscle-derived cells engineered to express IGF-1 can be used to improve muscle healing following orthopaedic injuries, including laceration, contusion, strain, ischemia and denervation (Table 5). Since adenovirus has been found immunogenic, an adeno-associated virus was constructed to carry the gene for expression of IGF-1 (FIG. 12). This virus is used to engineer muscle cells that will be injected after engineering in vitro to express IGF-1 in the injured muscle and consequently improve muscle healing following injury.

It was also determined that myoblast mediated ex vivo gene transfer could efficiently deliver β-galactosidase expressing adenovirus in injured muscle. In fact, the myoblast mediated ex vivo approach resulted in the production of many β-galactosidase positive myofibers in the injured muscle following laceration, contusion, and strain. Accordingly, injected myoblasts expressing growth factors are likely to improve muscle regeneration by the production of growth factors, and to serve as a reservoir of additional myoblasts that are capable of forming new myofibers.

TABLE 5

Effect of Growth factors on twitch/tetanic strength

| Effect of Trophic Factors on Muscle Strength In Vivo | NGF | bFGF | IGF-1 |
|---|---|---|---|
| Muscle contusion | +/+* | +/+ | +/+ |
| Muscle laceration | −/− | +/+ | +/+ |
| Muscle strain | +/− | +/+ | +/+ |

*(+) improvement in strength vs. non-injected muscles;
(−) no improvement in strength vs. non-injected muscles.

D. Myoblast Transplantation to Enhance Muscle Regeneration and Improve Muscle Healing Following Injury Myoblast transplantation, which consists of the implantation of myoblast precursors (satellite cells), enhances muscle regeneration and creates a reservoir of normal myoblasts that can fuse and deliver genes to skeletal muscle.

To improve muscle healing following injury, muscle biopsy is obtained from a non-injured muscle of the same individual that will serve as an autologous donor for the myoblast transfer of the injured muscle. The use of autologous myoblast transfer can circumvent the well documented immune rejection problem, which is a major hurdle of myoblast transplantation (J. Huard et al., 1994, *Human Gene Ther.*, 5:949-958; J. Huard et al., 1994, *J. Clin. Invest.*, 93:586-599), and lead to improved muscle healing following injury.

Example 9

Myoblast-mediated cell transfer for improving, reducing or eliminating a number of orthopedic conditions was assessed in this example. The animal models used were newborn rabbit and adult SCID mice. Such experiments point to the utility of myoblast cell-mediated gene therapy for pathologic conditions of the musculoskeletal system, for example, arthritis and damage to joints, ligaments, cartilage and meniscus.

The present inventors have performed extensive numbers of experiments exploring myoblast mediated gene transfer for orthopedic conditions. Although ex vivo gene transfer using synovial cells has been shown to deliver genes encoding anti-arthritic proteins into the rabbit knee joint, success using synovial cells has been limited by a transient expression of the transgene. In accordance with the present invention, muscle cells were employed as an alternative gene delivery vehicle to the joint in both newborn rabbits and adult SCID mice. It was demonstrated that myoblasts were transduced with a higher efficiency than synovial cells using the same adenoviral preparation to infect/transduce the cells in vitro. Following intra-articular injection of genetically engineered muscle cells, the engineered myoblasts adhered to several structures in the joint, including the ligament, capsule, and synovium. In addition, myoblasts fused to form many post-mitotic myotubes and myofibers at different locations of the newborn rabbit joint 5 days post-injection.

In the knees of adult SCID mice, myoblasts fused and expressed the reporter gene for at least 35 days post-injection. The presence of post-mitotic myofibers in the knee joint reveals the advantages of the present invention for long term expression of secreted protein. Currently, numerous tissues in the joint (ligament, meniscus, cartilage) have poor intrinsic healing capacity and frequently need surgical corrections. A stable gene delivery vehicle to the joint, which produces proteins that ameliorate these different musculoskeletal conditions, provides a change for the clinical implications of joint pathologies.

A. Preparation of Primary Myoblasts and Synovial Cells

Muscles from newborn (2-day-old) rabbit legs were removed, and muscle tissue was isolated from other connective, vascular, cartilaginous and bony tissues under a dissecting microscope. The isolated myogenic tissue was dissociated by enzymatic treatment with collagenase 0.2% (1 hour) and trypsin 0.1% (30 minutes) to isolate satellite cells. The primary cultures of myogenic cells were enriched by preplating (1 hour) the cell suspension in 24-cm² tissue culture flasks coated with 2% gelatin. Since fibroblasts tend to adhere to the substratum faster than myoblasts, the supernatant containing myoblasts and other cell types was replated and maintained in DMEM medium containing 20% fetal bovine serum (FBS) for three days to obtain approximately $5 \times 10^6$ myoblast cells per flask.

The primary cultures of synovial fibroblasts were prepared from dissected synovia of adolescent New Zealand White rabbits. The cells were grown in Ham's F-12 medium supplemented with 10% FBS (S. Floyd et al., 1997, *Basic Appl Myol.*, 7(3&4)).

B. Preparation of Myoblasts and Synovial Cells from Immortalized Cell Lines

The mdx myoblast cell line was isolated from a transgenic mdx mouse carrying a thermolabile SV40 T-antigen under the control of an inducible promoter (J. Huard et al., 1994, *Human Gene Ther.*, 5:949-958; J. Huard et al., 1994, *J. Clin. Invest.*, 93:586-599). The permanent mdx cell line proliferates indefinitely under permissive conditions (33° C. with gamma interferon) and undergoes normal differentiation at 37-39° C. without gamma interferon. The immortalized, rabbit-derived synovial cell line HIG-82 (H. I. Georgescu et al., 1988, *In Vitro Cell. Dev. Biol.*, 24:1015-1022) was propagated in Ham's F-12 medium supplemented with 10% FBS.

C. Comparison of the Transduction Efficiency of the Different Cell Types

Once all of the cell types were prepared (i.e., primary and immortalized myoblasts and primary and immortalized synovial cells), 50,000 cells of each type were plated in 6 well plates. Each well was then incubated for 48 hours with an adenoviral vector carrying the LacZ reporter gene under the control of the human cytomegalovirus promoter (AV-HCMV-LacZ from Genvec) at a multiplicity of infection of 25 (MOI=25). The cells were then stained for the presence of β-galactosidase using X-gal histochemistry. The amount of β-galactosidase activity was also quantified using the LacZ assay (J. Huard et al., 1997, *Human Gene Ther.*, 4:439-450).

D. Myoblast Differentiation In Vitro and Desmin Staining

Some myoblast cultures were allowed to differentiate by using a fusion medium containing DMEM supplemented to contain 2% FBS. This fusion medium reduced cellular proliferation and promoted myoblast fusion. After myotubes had formed in culture, X-gal staining was also performed. In addition, standard desmin (muscle specific marker) immunohistochemistry was also performed to validate the myogenicity index of these cell cultures (J. Huard et al., 1995, *Gene Therapy*, 2:1-9; D. K. Booth II et al., 1997, *J. Tissue Eng.*, 32:125-132; J. VanDeutekom et al., *Human Gene Therapy*, 1997).

E. Determination of the Early Fate of the Muscle Cells Injected into the Newborn Rabbit Joint Primary synovial cells, immortalized synovial cells, primary muscle cells and immortalized myoblast cultures were first infected with 25 MOI of AV-HCMV-LacZ for 24 hours as described above. After viral infection, the cells were rinsed and further incubated with a 1:1000 dilution of Fluorescent Latex Microspheres (FLMs), (Microprobes, Inc.), for an additional 12 hours. The FLMs are fluorescent microspheres which are phagocytized by cells and can serve as an additional marker to follow the early fate of the cells injected into the joint (A. Satoh et al., 1993, *J. Histochem. Cytochem.*, 41:1579-1582).

The infected cells incubated with FLMs were injected into the knees of newborn rabbit pups. Each flask of $1 \times 10^6$ cells was trypsinized using 0.5% Trypsin-EDTA, centrifuged at 3500 rpm for 5 minutes, and resuspended in 100 μl of Hank's Balanced Salt Solution (HBSS). The newborn pups were anesthetized using methophane inhalation for 1 minute. 100 μl solutions of infected muscle cells ($1 \times 10^6$ cells) were injected into the knee joint via the patellar tendon using a 30 gauge needle. A total of 10 rabbit pups were used: 2 (4 knees) injected with the primary muscle cells; 2 (4 knees) injected with the immortalized synovial cells; 4 (8 knees) injected with the immortalized myoblasts; 1 (2 knees) injected with saline; and 1 (2 knees) served as a sham, non-injected control.

The pups were sacrificed five days post-injection, and the knees removed in their entirety. The knees were snap frozen and cryostat sectioned in their entirety in 10 μm thick slices. Various analyses were performed on these knee sections, including: histological staining (hematoxylin-eosin); detection of β-galactosidase; localization of FLMs; and desmin immunofluorescence labeling. The distribution of the FLMs and desmin was visualized using fluorescent microscopy (Nikon Optiphot-2). Co-localization of FLMs and β-galactosidase was used to substantiate the transgene expression from the injected cells. This additional marker minimized the chances of false positive results which often occur due to endogenous LacZ expression. In addition, myoblast fusion into the intra-articular structures was investigated using desmin labeling.

Newborn rabbits were used for this phase of analysis because their knees do not begin calcifying until 15 days of age. Thus, it is possible to flash freeze them in their entirety and analyze the entire knee systematically. This systematic analysis of cryostat sections demonstrating gene therapy to the joint has not been done previously. This approach permitted the characterization of the different intra-articular structures to which the transduced cells had adhered.

F. Determination of Long Term Expression of the Transduced Muscle Cells Injected into the Joints of Adult SCID Mice $5 \times 10^5$ transduced immortalized muscle cells infected with the AV-HCMV-LacZ vector (MOI=25) were incubated with FLMs, resuspended in 10 μl of HBSS and injected into the knees of 12 adult SCID (immunodeficient) mice. Three mice were sacrificed at 5, 15, 25 and 35 days post-injection. The knees were first decalcified at 4° C. in a 50:50 dilution of 0.5 M EDTA and 1 M glucose solution for 3 days. They were then flash-frozen and cryostat-sectioned in their entirety in 10 μm thick slices. β-galactosidase expression was analyzed using X-gal histochemistry and FLM localization was visualized using fluorescent microscopy (Nikon Optiphot-2). SCID mice were used in this experiment to bypass potential immunological complications associated with the first generation adenovirus. Adult mice were used to ensure that the ability of myoblasts to adhere to intra-articular structures was reproducible in the mature knee.

This study was subdivided into three interrelated sections, which are described in greater detail hereinbelow. First, the primary myoblasts, immortalized myoblasts, primary synovial cells and immortalized synovial cells were characterized in vitro for their efficiency of viral transduction using a first generation adenoviral vector. This phase compared myoblasts to cell types already being used as gene delivery vehicles to the joint.

The early fate (5 days post-injection) of the injected muscle cells into the joint was analyzed. This second phase included the evaluation of the viability of the injected cells in vivo, determination of the internal structures of the joint to which the myoblasts adhered, evaluation of myoblast mediated gene transfer of β-galactosidase, and characterization of the ability of the muscle cells to differentiate into myotubes and myofibers in the joint.

The third phase analyzed the long term expression of myoblast mediated gene transfer in the adult knee. Briefly, a myoblast cell culture was isolated from a muscle biopsy. These cells were then transduced in vitro by an adenoviral vector carrying the LacZ reporter gene. The transduced myoblasts were injected into the knee joint.

Figure 3A:
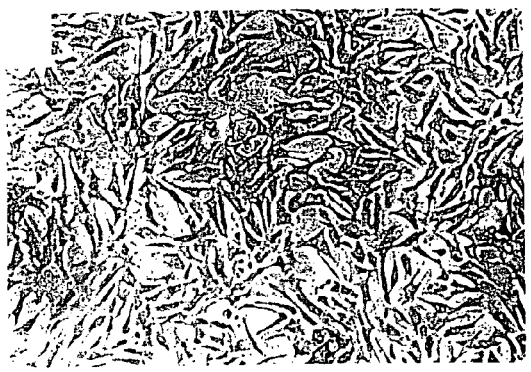
FIGS. 3A-3F show the results of transducing myoblasts versus synovial cells in vitro (Example 9). Synovial cells (FIGS. 3A, 3B) and myoblasts (FIGS. 3C, 3D) are from cell lines grown in culture. Both cell lines were infected with an adenovirus vector carrying the LacZ reporter gene using a similar multiplicity of infection (MOI=25). The expression of β-galactosidase by both cell types was observed using LacZ histochemistry at 2 days (FIGS. 3A, 3C) and 6 days (FIGS. 3B, 3D) post-infection. The transduced myoblasts were shown to preserve their ability to differentiate into myotubes expressing β-galactosidase (FIG. 3D). Desmin immunofluorescence of myoblast cultures indicated the presence of multiple, long, pluri-nucleated myotubes where the myoblasts were allowed to differentiate using fusion media (FIG. 3E). The amount of β-galactosidase production by the four different cell cultures at two days post-infection was quantified using the lacZ assay. The immortalized myoblasts produced nearly 5 times more β-galactosidase than did primary myoblasts, primary synovial cells and immortalized synovial cells. Magnifications A-E: 10×.
Figure 3B:
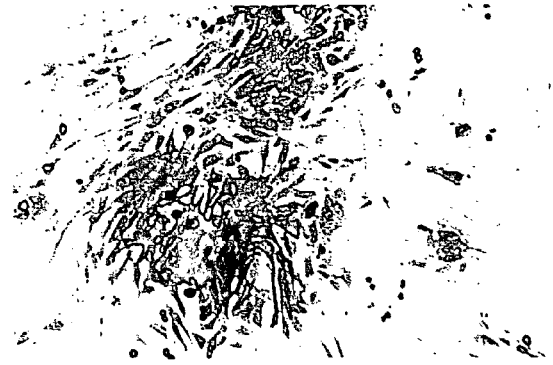
Figure 3C:
Figure 3D:
Figure 3E:

I) In vitro analysis: All four cell types: primary synovial cells, immortalized synovial cells, primary myoblasts and immortalized myoblasts were isolated, grown, and transduced with the AV-HCMV-LacZ vector in vitro. Expression of β-galactosidase was observed in synovial cells (FIGS. 3A and 3B) and in myoblasts (FIGS. 3C and 3D) at 2 days (FIGS. 3A and 3C) and 6 days (FIGS. 3B and 3D) post-infection. However, when transduced immortalized myoblasts were allowed to fuse in culture, multiple fused multinucleated myotubes expressing β-galactosidase were seen (FIG. 3D). The positive desmin fluorescent staining (green fluorescence—FITC) validated the high myogenicity index of the myoblast culture (FIG. 3E).

Figure 3F:
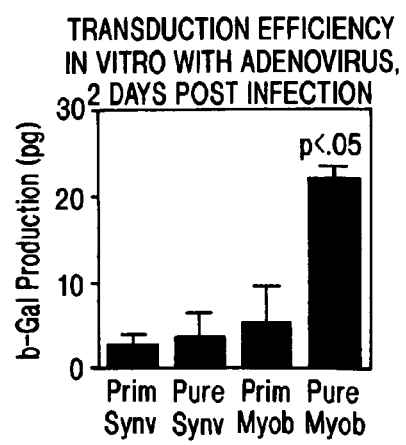

When the different cell types were analyzed in the LacZ assay at two days after infection, 2.5 to 5.0 picograms of β-galactosidase per one million cells were produced by the primary synovial, pure synovial, and primary muscle cells. In contrast, the immortalized, transduced myoblasts produced over 20 picograms of β-galactosidase per one million cells. This was significantly higher (paired T-tests) than the other cell types, $p<0.05$ (FIG. 3F). In addition, the transduction of myoblast and synovial cells with an adenovirus which carry the expression of IL-1Ra lead also to a higher production of IRAP by the myoblast cells than the synovial cells (FIG. 4).

II) Determination of the early fate of the injected muscle cells into the joint: The histologic examination of newborn rabbit knee sections demonstrated that the injected myoblasts had fused with most of the structures of the knee. Transplantation of transduced synovial cells into the knee produced β-galactosidase, but only in some parts of the synovial lining (S) of the joint. However, by injecting primary myoblasts, numerous tissues of the joint, i.e., synovium (S), meniscus (M) and ligament were found to contain cells expressing β-galactosidase. With desmin staining (green fluorescence—FITC), very few myotubes were detected in the injected joint with primary myoblasts.

The poor level of gene transfer mediated by injection of primary myoblasts may be attributed to a decrease in the number of muscle cells and also to the heterogeneous population of cells in these cultures (fibroblasts, adipocytes, etc.). In fact, a better gene complementation was achieved in muscle cells in vitro by using the immortalized myoblast culture compared with the primary myoblast culture containing other cell types. In order to validate this hypothesis, myoblasts from an immortalized cell line were then investigated using a similar ex vivo approach.

The transplantation of immortalized myoblasts produced large patches of muscle cells expressing β-galactosidase in the synovial lining adjacent to the patella. With desmin immunofluorescence staining, multiple fused myotubes and myofibers were visualized in the same area. Some of the myotubes were seen longitudinally, and others were seen in cross section (rounded circular structures). These myotubes and myofibers were definitely formed by the fusion of the transplanted myoblasts due to the co-localization of FLMs and desmin positive cells. Moreover, some injected myoblasts adhered to the patellar ligament and expressed β-galactosidase within the striated ligamentous structures. In this same area, multiple long myotubes stained for desmin were depicted, thus demonstrating the presence of myogenic cells at this location.

Most of the knees showed a propensity for the myoblasts to congregate and fuse in the joint capsule of the femoral lateral recess. In contrast to the synovial cell and primary myoblast injections, immortalized myoblasts were able to produce large patches of myotubes and myofibers expressing β-galactosidase in the joint capsule. Large disorganized patterns of myofibers expressing desmin co-localized with FLMs were also observed at the same location. This was distinctly different from the normal extra-capsular in vivo muscles that also stained positive for desmin, but were without FLMs. On higher magnification, cross sections of large diameter desmin positive muscle fibers co-localized with FLMs were seen in this joint capsule (Day et al, 1997 *J. Orthop. Res.*, 15, 894-903).

In parts of the cruciate ligaments located in the femoral notch (FN), the presence of myoblasts expressing β-galactosidase was observed following transplantation of immortalized myoblasts into the joint. However, smaller and more irregularly shaped desmin positive cells were detected, suggesting the presence of myoblasts that had not yet differentiated into myofibers. At higher magnification, transverse sections of small myotubes containing FLMs were still visualized in the femoral notch.

III) Determination of the Long Term Expression of Muscle Cells Injected into the Adult Mouse Knee When transduced immortalized myoblasts were injected into the knee of adult SCID mice, myoblast mediated gene transfer of the LacZ reporter gene was also seen in various structures in the knee including synovium, capsule, and tissues in the femoral notch. β-galactosidase production co-localized with FLMs was seen at 35 days post-injection. In the 35 day group, large aggregates of rounded structures suggestive of myotubes and myofibers producing β-galactosidase were seen in the femoral notch, synovium, and joint capsule.

Figure 5A:
FIGS. 5A-5D show the results of myoblast-mediated ex vivo gene transfer into rabbit meniscus. Myoblasts transduced with an adenovirus vector carrying the gene encoding β-galactosidase (LacZ) were injected into rabbit meniscus.
Figure 5B:
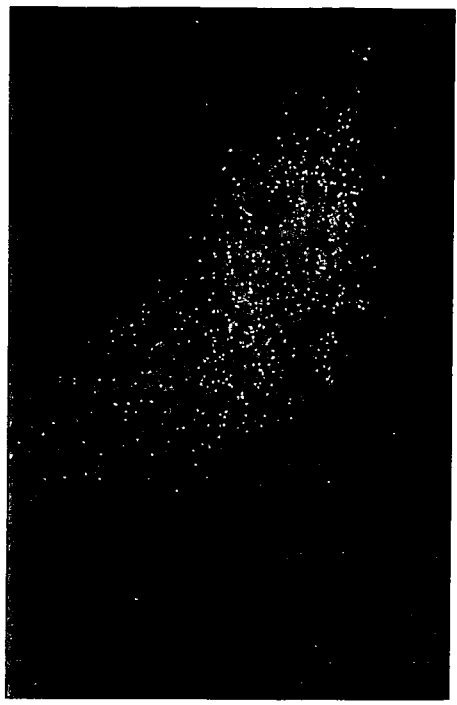
Figure 5C:
Figure 5D:

The direct injection of the transduced muscle cells into the intraarticular structures leads to a high level of gene transfer in the meniscus and the anterior cruciate ligament. FIGS. 5A-5D show the results of myoblast-mediated ex vivo gene transfer in rabbit meniscus. Myoblasts transduced with an adenovirus vector carrying the gene encoding β-galactosidase (LacZ) were injected into rabbit meniscus. FIGS. 5A and 5B show the expression of LacZ in the meniscus following injection and expression of β-galactosidase. FIG. 5C shows that LacZ staining is co-localized with fluorescent latex microspheres in the injected area. FIG. 5D shows the expression of desmin, a myogenic marker (green fluorescence).

FIGS. 6A and 6B show the results of myoblast-mediated ex vivo gene transfer into rabbit ACL ligament. Myoblasts transduced with an adenovirus vector carrying the gene encoding β-galactosidase (LacZ) were injected into rabbit ligament. FIGS. 6A and 6B show the expression of LacZ in the ligament following injection and expression of β-galactosidase. FIG. 6C shows that LacZ staining is co-localized with fluorescent latex microspheres in the injected area. FIG. 6D shows the expression of desmin, a myogenic marker (green fluorescence), revealing the presence of muscle cells in the ligament.

In vitro data detail the effects of numerous growth factors on fibroblast proliferation and collagen production. In fact, according to the present invention, platelet-derived growth factor (PDGF), epidermal growth factor (EGF), transforming growth factor α (TGF-α), and basic fibroblast growth factor (bFGF), were observed to improve the proliferation of the meniscal fibrochondrocytes and their expression of collagen and non-collagen proteins.

Regardless of which growth factor is employed for meniscal healing, the cardinal issue of protein delivery must be addressed. Direct intrameniscal of the recombinant growth factor protein injections are unlikely to produce sustained levels without the need for multiple injections, a scenario that is not clinically appropriate. Efficient and sustained delivery of desired growth factors may be best accomplished by gene delivery. As disclosed herein, muscle cell-mediated ex vivo gene delivery offers the possibility of sustained, high level gene expression.

The muscle cell-mediated ex vivo approach was further employed to deliver marker genes to the rabbit meniscus. The results demonstrated that muscle-derived cells can be used as a gene delivery vehicle to the meniscus (FIGS. 5A-5D). The ability of muscle-derived cells to be used as a reservoir of secreting molecules to enhance meniscal healing, and the ability of some populations of muscle-derived cells to differentiate into various lineages allow such cells to participate in the meniscal healing process. These findings may lead to novel therapies for meniscal injuries, preventing significant morbidity from these chronically disabling injuries.

In addition, the capacity of meniscal cartilage for healing in the avascular central portion of the meniscus is very limited, possibly directly related to the blood supply which exists only in the peripheral third of the meniscus. Experimental studies have shown that the healing process in the central part of the meniscus might be promoted by some chemotactic or mitogenic stimuli delivered by the fibrin clot or synovial tissue. The use of vascular endothelial growth factor (VEGF), which promotes angiogenesis, is likely to be helpful to improve meniscal healing. FIG. 12 presents a schematic of an adeno-associated viral construct to carry the expression of VEGF for delivery via muscle-based gene therapy and tissue engineering.

IV) Use of Muscle Cells to Deliver Genes in a Cartilage Defect

Figure 14A:
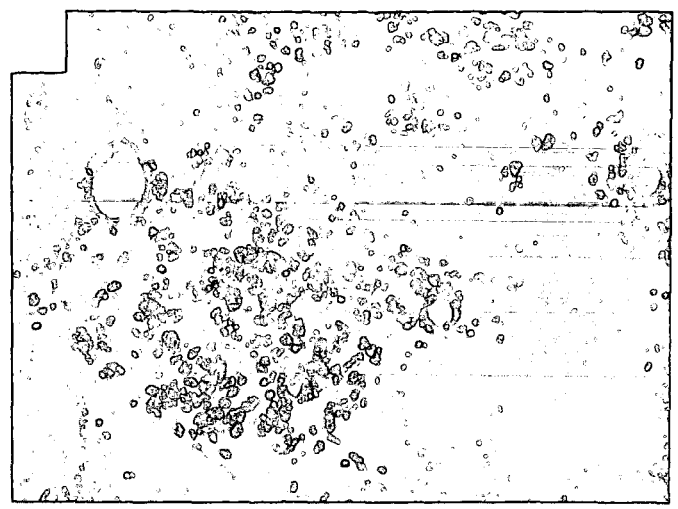
FIGS. 14A-14C show the results of myoblast-mediated ex vivo gene transfer into rabbit cartilage. Myoblasts transduced with an adenovirus vector carrying the gene encoding β-galactosidase (LacZ) were injected into rabbit cartilage.
Figure 14B:
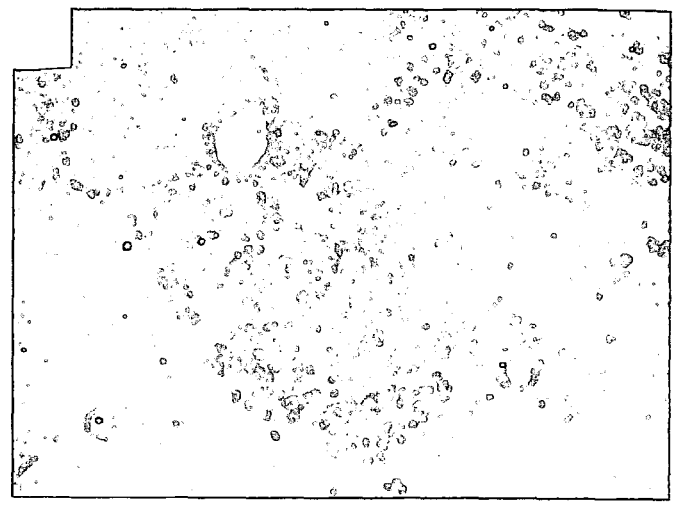
Figure 14C:
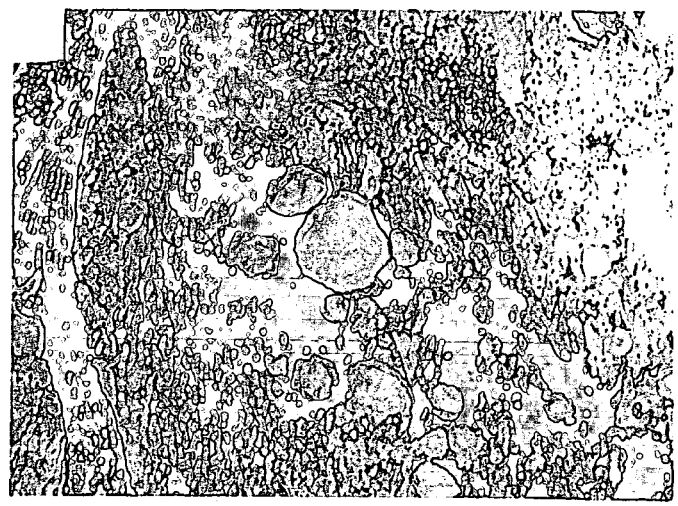

Articular cartilage has a limited capacity to repair after injury. Defects of articular cartilage that do not penetrate the subchondral bone can not heal efficiently and result in the degeneration of articular cartilage. On the other hand, injuries which penetrate the subchondral bone result in the formation of fibrocartilage or hyalin-like cartilage that are different from the normal articular cartilage, and eventually lead to the degeneration of joint cartilage. According to this invention, muscle cells were used to deliver genes in a cartilage defect (FIG. 14).

Figure 13:
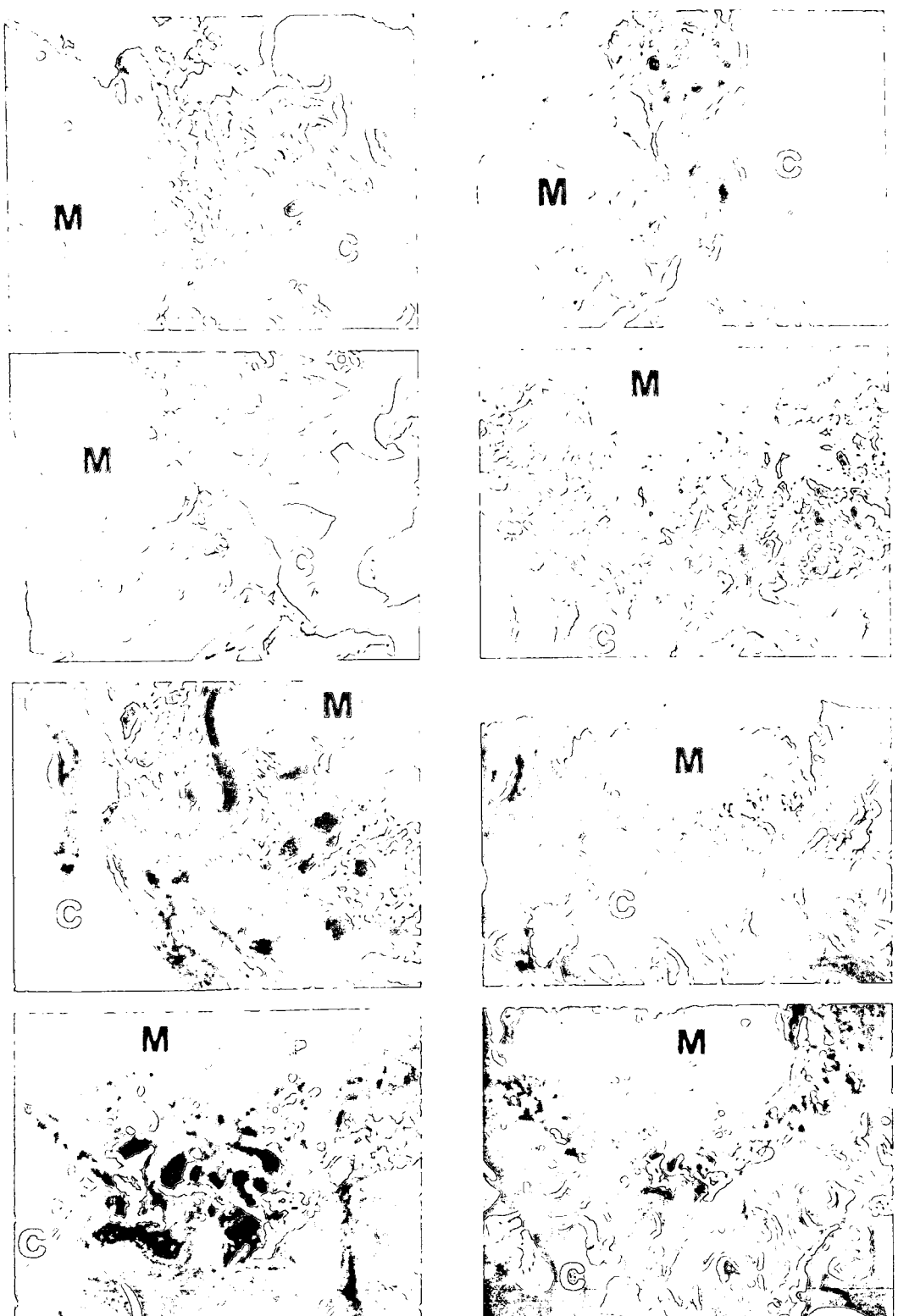
FIG. 13 shows the results of the use of a muscle biopsy for cartilage healing. In the frames as shown, the muscle biopsy is seen to be encasing the cartilage defect at 3 weeks post-injection and muscle and cartilage formation is apparent. The muscle biopsy can therefore be used as a biological scaffold to deliver growth factors, as well as a source of pluripotent muscle-derived cells to improve the healing of cartilage defect. In this figure, "M" represents muscle, while "C" represents cartilage.

Moreover, the transposition of a muscle flap into a cartilage defect can also be used to improve cartilage healing (FIG. 13). It is envisioned that muscle based gene therapy and tissue engineering according to the present invention can be used to improve the healing of articular cartilage defect. The use of adeno-associated virus encoding molecules such as BMP-2, VEGF, and IGF-1 can be used to further improve the healing of the articular cartilage, as depicted in the schematic representation of FIG. 12.

In addition, many acquired musculoskeletal conditions would be amenable to new vehicles that safely and efficiently deliver genes and their expression, namely, degenerative arthritis, cartilage damage, ligament damage, delayed unions or non-unions in fractures, osteosarcoma and various rheumatoid diseases. Since the knee joint sustains many of these conditions, improved gene therapy to the joint, for example, as a drug delivery system, is an important and needed achievement in the art, and one that is readily provided by the present invention.

Example 10

This example sets forth experiments that were performed to demonstrate the use and advantages of myoblast mediated gene transfer to ameliorate a bone defect.

A myoblast cell line isolated from transgenic mdx mice carrying a thermolabile SV40 T-antigen under the control of an inducible promoter (J. E. Morgan et al., 1994, *Dev. Biol.*, 162:486-498) was used. The immortalized mdx cell line proliferated indefinitely at 33° C. with gamma interferon and underwent normal differentiation at 37-39° C. without gamma interferon. These myoblasts were kept in cell culture and infected with the adenoviral-lacZ vector (MOI=25). The cells were also incubated with fluorescent latex microspheres (FLMs) which served as another marker by which the fate of these cells could be followed in the bone defect. Prior to injection, some flasks containing the transduced cells were analyzed for β-galactosidase production and desmin expression by immunofluorescence staining.

External fixators were surgically placed in the right tibias of 8 adult rabbits. A 0.7-1 cm tibial bone defect was created in the rabbit via an osteotomy between the second and third pins of the external fixator. $7 \times 10^6$ transduced myoblasts were trypsinized and injected into the muscle surrounding the bone defect during the osteotomy. The same number of transduced myoblasts were also injected percutaneously into the bone defect 24 hours after the osteotomy. One osteotomized rabbit did not receive the myoblast injections and served as a sham control. The animals were sacrificed at 6 days post-injection, and the entire leg with the external fixator in place was analyzed macroscopically for lacZ expression. The tissue in the defect and the surrounding muscles were then flash frozen, cryostat sectioned, assayed for β-galactosidase by histochemistry and for desmin by immunofluorescence as described in C. S. Day et al., 1997, *J. Orthop. Res.*, 15:894-903). The FLMs were localized using fluorescent microscopy.

All of the rabbit tibial defects injected with transduced myoblasts demonstrated β-galactosidase production macroscopically in the muscles surrounding the defect and in the defect itself. In contrast, the sham operated control defect did not demonstrate any β-galactosidase production. When the tissue in the defect was cryostat-sectioned and analyzed microscopically for lacZ expression, many rounded cells producing β-galactosidase were seen in the midst of the much smaller fibroblasts. Moreover, when analyzed concomitantly under fluorescent microscopy, numerous FLMs were co-localized with the rounded myofibers expressing the lacZ reporter gene. LacZ expression was also seen in the muscles surrounding the defect that had received the myoblast injections on day 7 after the injection.

The sectioned defect tissue was also analyzed for desmin expression, and many areas in the injected bone that expressed desmin were also co-localized with FLMs. Desmin staining was indicative of the presence of muscle cells that had fused into myofibers in the non-muscle area of the segmental bone defect. Thus, myoblasts successfully delivered the marker gene into a bone defect, the protein product was expressed, and myofibers had formed, thus allowing for the persistence of gene product expression in the fused myotube cells derived from the genetically engineered myoblast cells injected into the bone.

Example 11

To confirm that a population of cells in skeletal muscle was capable of differentiating into bone, variable populations of cells derived from muscle were stimulated by BMP-2 protein and analyzed for osteogenic differentiation in vitro as described below.

Primary cell cultures were obtained from an adult mdx mouse (T. A. Rando and H. M. Blau, 1994, *J. Cell. Biol.*, 125:1275-1287). Briefly, the mouse was euthanized by cervical dislocation and approximately 500 mg of hindlimb muscle was immediately dissected and minced. The muscle was enzymatically digested by serial incubation in 0.2% collagenase, dispase (2.5 units/ml) and 0.1% trypsin, each for 1 hour at 37° C. Any remaining cellular clumping was disassociated by passage through a 20 gauge needle. The cells were then plated onto collagen-coated flasks in F10 Ham (Gibco BRL, Gaithersburg, Md.), supplemented to contain 10% horse serum, 10% fetal bovine serum, 1% penicillin/streptomycin, and bFGF (human recombinant, Life Technologies). Cells were subdivided according to their cellular adhesion characteristics by serial passage of cell supernatant to a new flask after approximately 15-20% of the cells adhered to the flask. This technique, termed preplating is described in Example 1, Purification of Primary Myoblasts, herein. This procedure was repeated six times, yielding six preplates. Cells adhering to the flasks earlier remained in the lower preplates, while those passed along in the serial supernatants adhered in the higher preplates. Fibroblasts adhere more rapidly than do myoblasts under the conditions of this procedure; hence, the higher preplates are enriched for myoblasts.

The different subpopulations of cells were plated at $2 \times 10^4$/well in 12 well plates. Cells from each preplate were incubated in medium or in medium supplemented to contain 50 ng/ml or 200 ng/ml BMP. BMP was added to the appropriate wells at 1, 3 and 5 days after plating. A cell lysate was obtained 24 hours after the final BMP-2 stimulation for the assay of alkaline phosphatase activity. The cells found to be the most responsive were re-examined under stimulation with 100 ng/ml of BMP-2 stimulation over the same time course. To study the effect of BMP-2 stimulation over time, a portion of the cells was removed after each addition of BMP-2 for the analysis of desmin expression and ALP activity.

The analysis of desmin expression in the cells was performed by standard immunohistochemical techniques. Cells were fixed with cold methanol for 1 minute, rinsed in phosphate buffered saline (PBS) and blocked with 10% horse serum for 1 hour. The cells were then incubated with a 1/100 dilution of mouse anti-desmin antibody (Sigma) for 6-10 hours at 37° C. Following the rinses with PBS, the cells were incubated with a 1/100 dilution of anti-mouse antibody conjugated to Cy3 fluorescent marker (Sigma) for 1 hour. Staining was then assessed with an immunofluorescent microscope (Nikon). Data were quantified by examining five different fields at 10× magnification and counting the positive and negative cells to establish a ratio. Alkaline phosphatase activity (in U/L) was determined by the hydrolysis of p-nitrophenyl phosphate to p-nitrophenol and inorganic phosphate using a commercially available reagent and protocol (Sigma). When appropriate, statistical analysis was performed by ANOVA testing for statistical difference at greater than 95% confidence intervals.

The results showed that prior to stimulation with BMP-2, the different subpopulations of muscle-derived cells were characterized by desmin staining. For the cell platings, cells in preplate #1 stained 3% desmin positive versus 70.5% positive cells in preplate #6. The percentage of desmin positive cells increased with statistically significant increments between preplate #3 and preplate #5, and between preplate #5 and preplate #6. Of interest, the cells having the highest level of desmin positivity tended to appear round and divide more slowly than those in earlier preplates.

Figure 9:
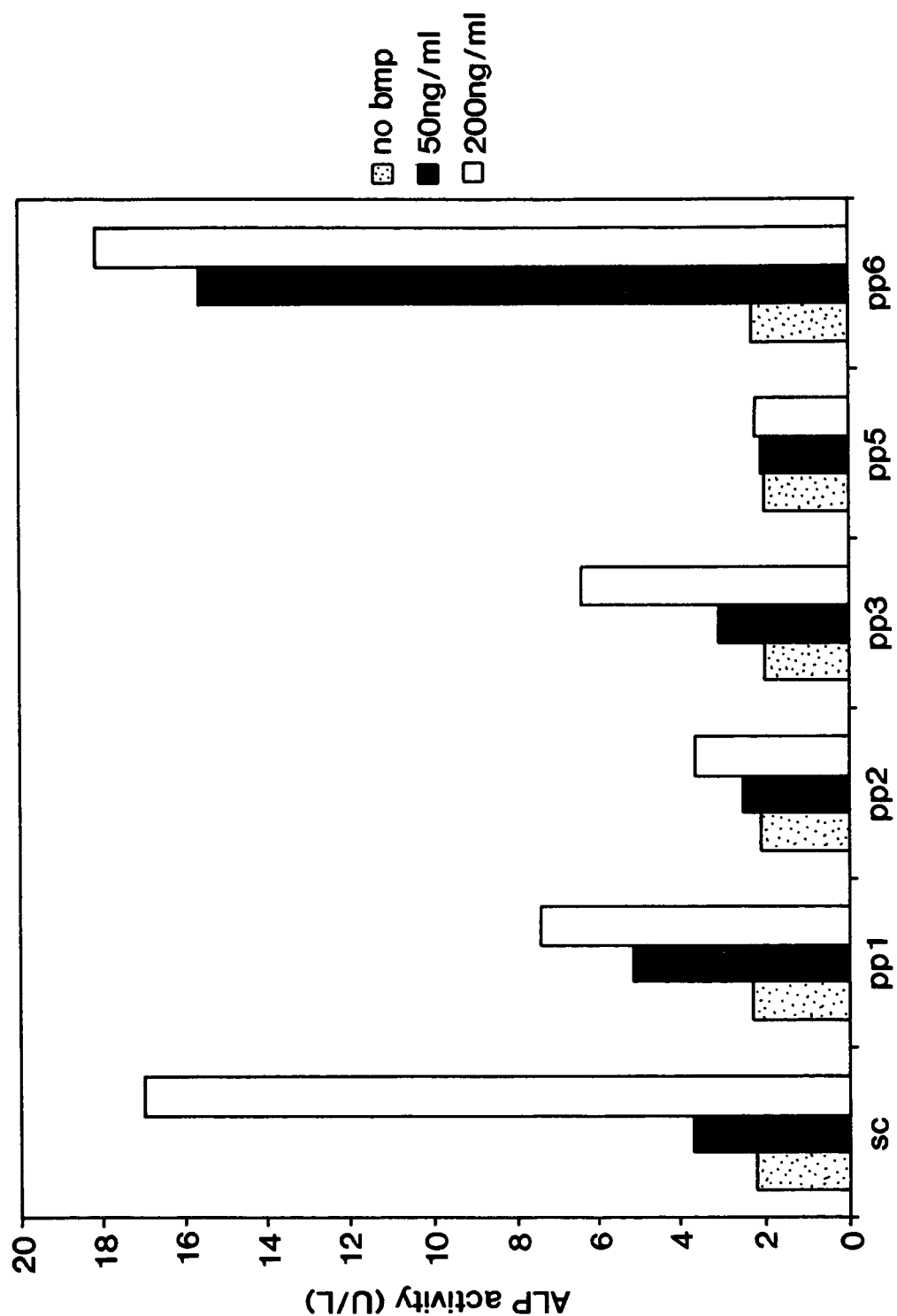
FIG. 9 presents the levels of alkaline phosphatase activity (ALP), U/L, after various muscle-derived cell populations (pp1-pp6) are stimulated with osteogenic protein BMP-2, t=30 minutes. The cell types are stromal cells (control) and preplated (pp) cells #1, 2, 3, 5 and 6 as described. The PP#6 corresponds to BMP-2 by producing alkaline phosphatase in a dose dependent manner and at a level similar to that observed with stromal cells (SC)

After stimulation with BMP-2, the subpopulations of cells were tested for the induction of alkaline phosphatase, a biochemical indicator of osteoblastic activity (A. I. Caplan, 1991, *J.Orthop. Res.*, 9:641-650). A mouse-derived population of stromal cells was used as a positive control. Muscle-derived cells not receiving BMP-2 did not express ALP activity. Only the subpopulation obtained from preplate #6 showed an increase in ALP activity in response to stimulation with BMP-2. A dose-dependent trend was seen when comparing data for preplate #6 using BMP-2 at a concentration of 50 ng/ml versus 200 ng/ml (FIG. 9).

Figure 10:
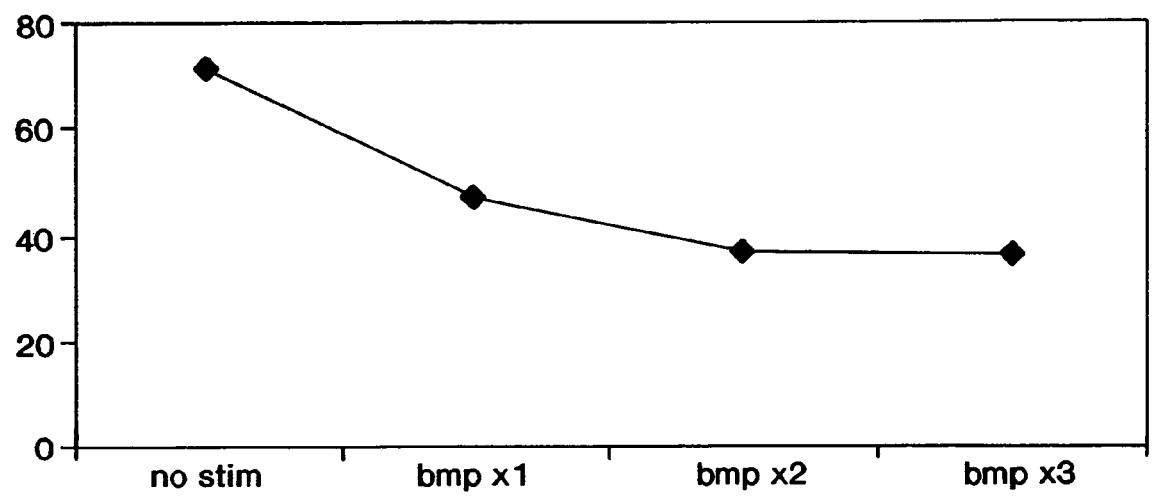
FIG. 10 presents the percentage of desmin-positive cells following different numbers of doses (100 ng/ml) of BMP-2. It was observed that stimulation of BMP-2 not only increased the level of alkaline phosphatase expression by the muscle-derived cells, but also decreased the number of desmin positive cells in the population of muscle-derived cells.

Corresponding to the increase in ALP activity in response to BMP-2 stimulation in preplate #6, the percentage of desmin-staining cells decreased (FIG. 10). After a single dose of BMP-2, the percentage of desmin-positive cells in preplate #6 decreased from 70.5% to 47%. Additional doses of 100 ng/ml of BMP-2 did not cause as much of a decrease; the level of desmin positive cells remained at approximately 40%.

In addition, different populations of muscle-derived cells were isolated from a human muscle biopsy and were purified by the preplate technique. When stimulated with BMP-2 as described above, cells from some of the preplates (i.e., pp2, pp3, and pp4 to a lesser extent) expressed alkaline phosphatase (marker for pre-osteoblasts). Therefore, according to the invention, human muscle-derived cells can be isolated and purified and shown to have stem cell characteristics.

Cells isolated from skeletal muscle are capable of responding to recombinant human (rhBMP-2) both in vitro and in vivo. Primary rodent myogenic cells in cell culture respond in a dose dependent fashion to rhBMP-2 by producing alkaline phosphatase, an osteogenic protein. Furthermore, the purer the population of myogenic cells, as evidenced by desmin staining, the greater the alkaline phosphatase production. Recombinant human BMP-2 inhibits myogenic differentiation as it stimulates osteoblastic differentiation of the muscle-derived cells (A. Yamaguchi et al., 1991, *J. Cell Biol.*, 113: 681-687; T. Katagiri et al., 1994, *J. Cell Biol.*, 127:1755-1766; K. Kawasaki et al., 1998, *Bone*, 23:223-231). Accordingly, in vitro data suggest that myogenic cells are capable of responding to rhBMP-2 and entering an osteogenic lineage.

Figure 11A:
FIG. 11 shows that injected muscle-derived cells (PP#6) stimulated with BMP-2 and inserted into a theracyte immunoisolation device (described in Example 1) which was implanted subcutaneously are capable of participating in bone formation as seen by von Kossa (mineralization) and hematoxylin/eosin. These results suggest that muscle-derived cells are capable of forming bone.
Figure 11B:

Primary rodent muscle-derived cells were engineered to produce intramuscular bone in vivo. The ex vivo approach was utilized to transduce the primary muscle-derived cells with an adenovirus carrying the BMP-2 cDNA. Intramuscular injection of as little as 300,000 transduced cells produced bone in severe combined immune deficient (SCID) mice. The bone produced contained osteoid and bone marrow elements as evidenced by regular histology and von Kossa for mineralization. Not only did the transduced muscle cells produce BMP-2, but the injected cells also respond to BMP-2 by producing bone Moreover, engineered muscle-derived cells within diffusable chambers (see Example 1) that preclude the entry of host cells due to the pore size, produced bone when implanted sub-cutaneously in immunodeficient mice. These results suggest that these specific populations of muscle-derived cells are capable of producing bone (FIG. 11). The ability of the cells to differentiate into other lineages such as bone substantiate the pluripotent nature of these muscle-derived cells, i.e., muscle-derived stem cells.

As described hereinabove, the preplate technique provided a means for attaining different populations of muscle-derived cells in different preplates. With selective preplates of cells, bone formation was achieved (e.g., FIG. 11), thus, strongly suggesting the presence of muscle stem cells. Table 6 summarizes the expression of different markers by purified mouse muscle-derived cells.

TABLE 6

| Cell Type | Mdx pp#6 | Normal pp#6 | Fibroblast |
|---|---|---|---|
| Desmin | + | + | − |
| Bcl2 | + | + | − |
| CD34 | + | + | − |
| MyoD | +/− | +/− | − |
| Myogenin | +/− | +/− | − |
| M-Cadherin | −/+ | −/+ | − |
| MyHCs | (+) | (+) | − |

In Table 6, Mdx pp#6 and normal pp#6 were derived from hindlimb muscle of newborn mdx and normal mice, respectively, by the preplate technique as described herein. "+" indicates that more than 95% of the cells in the culture expressed high levels of antigen. "+/−" indicates that approximately 60% or 30% of the cells in the cultures expressed MyoD or Myogenin antigen, respectively. "−/+" indicates that less than 10% of the cells in the culture expressed M-Cadherin, and "(+)" indicates more than 95% of the cells in the three-day-fusion medium expressed myosin heavy chain isoform (MyHCs).

In addition to the ex vivo approach, an adenovirus mediated direct gene transfer of BMP-2 produced large amounts of intramuscular bone. Consequently, both the in vitro and in vivo data support the hypothesis that muscle cells may be engineered to become osteogenic cells. The ramifications of myogenic cells' capabilities to form bone are immense. In fact, the ability of the adenovirus carrying the expression of BMP-2 to induce radiographic and histologic ectopic bone formation at 2, 3 and 4 weeks post-injection suggests that muscle flap can be eventually used as a biological scaffold with the ability to improve healing of hard tissue including bone and cartilage. In fact, the use of a muscle flap treated with Adenovirus-BMP-2 may be capable of improving bone healing.

Since the use adenovirus vectors may be hindered by immune responses against the vectors, the use of a less immunogenic vector has been determined to be required to improve bone formation by using the muscle as a biological scaffold. Therefore, adeno-associated virus has been used as a new viral vector to improve the efficiency of gene transfer to mature skeletal muscle. This vector can be employed to deliver BMP-2 into muscle flap to improve bone healing. A schematic representation of the plasmid use to construct an adeno-associated virus to carry the expression of BMP-2 is presented in FIG. 12.

Muscle-based tissue engineering to produce bone may be applicable to multiple skeletal abnormalities. One such scenario is large bone defects resulting from trauma or oncologic resections. Muscle-derived cells capable of bone formation may be exploited to reconstruct the bone defect and minimize the use of autograft, allograft, and bone distraction. A muscle flap may be able to be engineered to produce bone and, thereby, reconstruct an experimental bone defect. Both ex vivo and in vivo gene therapy techniques are amenable for bone formation and to reconstruct bone defects.

Another approach is to transform muscle, restricted to the confines of a silicone mold, into bone of desired geometry such as a proximal femur or midshaft tibia (R. K. Khouri et al., 1991, *JAMA,* 266:1953). The muscle-based approach to bone defect reconstructions is especially appealing in light of the often poor vascularity of traumatic and oncologic bone defects. The combination of vascularized muscle and de novo bone formation offers revolutionary possibilities for bone repair.

Example 12

This example provides a typical and highly practical application of muscle-derived cell mediated gene therapy and tissue engineering as provided by the present invention for the treatment of urinary tract dysfunction in human patients. The present invention has provided the ability to perform gene delivery to the lower urinary tract. In addition, the present invention has demonstrated that myoblast mediated gene therapy was more successful in delivering iNOS than using direct virus or plasmid infection/transfection methods.

The direct clinical utility of the present invention offers those skilled in the art the ability to treat patients simply, safely and efficiently on an out-patient basis, and even in the doctor's office. For example, in a urology office, patients with stress urinary incontinence undergo a simple needle aspiration of their muscle, for example, the triceps, that takes less than 5 minutes.

The muscle cells are grown under the appropriate cell culture conditions in a laboratory, preferably, a laboratory of a biotechnology center. This step takes about 1-4 weeks. The cultured muscle cells, now vastly increased in number, are shipped back to the treating doctor and are then injected back into the patient in a brief, 10 minute outpatient endoscopic procedure. The injection is performed using a small cystoscope and a cystoscopic needle. Under direct surgeon's vision, the needle tip is inserted into the urethral sphincter mechanism and the myoblast suspension is injected into the urethral wall to cause urethral coaptation and closure.

Cultured myoblasts can be frozen and stored indefinitely for possible future use. As described, muscle-derived cells can also be used for cell mediated gene therapy with various trophic factors to augment and/or enhance the treatment and repair process in a given tissue. Similar procedures of myoblast injection and gene therapy can also be done in the bladder of patients with impaired bladder contractility.

The number of cells removed from the patient does not need to be large, if the cells are subsequently placed in culture where they will proliferate and increase in number prior to injection. For injection, the number of cells used can be determined by the practitioner using routine skill, depending on the specific injury, disease or dysfunction being treated, the tissue or organ to be injected and the gene construct used. In general a lower cell number is used for gene delivery/gene therapy procedures, while a higher cell number is used for tissue engineering and bulking, i.e., on the order of about $1 \times 10^4$ to about $1 \times 10^{14}$, preferably about $1 \times 10^4$ to about $1 \times 10^6$ for gene delivery. If the cell number is found to be too low to produce an effective amount of gene product at and near the site of injection, repeat injections are easily performed and may be administered as needed.

In the inventors' practice of the protocol of the present invention, the injected muscle-derived cells have been found to remain at and near the site of injection in bladder, urethra, penis, leg muscle, knee joints and bone, for example. Further, histology of various tissues post-injection has not shown significant scar tissue formation, even if allogeneic cells were used. With autologous muscle-derived cells, scar tissue formation was virtually nil.

At and near the injection site, the injected myoblasts fused and formed myotubes based on the amount of surrounding space. Once the cells had filled up the area at the site of injection, myofibers formed and the cells no longer proliferated or grew. The multinucleated myofiber remained virtually the same size after it was formed and did not proliferate or die. Thus, on a longterm basis, the myofiber stably produced and secreted the gene product of the delivered, expressed encoding gene in the area of injection.

The contents of all patents, patent applications, published articles, books, reference manuals, texts and abstracts cited herein are hereby incorporated by reference in their entirety to more fully describe the state of the art to which the present invention pertains.

The present invention has been described in detail including the preferred embodiments thereof. However, it will be appreciated by those skilled in the art, upon consideration of this disclosure, that modifications and improvements may be made thereon without departing from the spirit and scope of the invention as set forth in the description and claims.

amount effective to augment skeletal muscle tissue, wherein the injury or damage is the result of laceration, contusion, or strain.

2. The method according to claim 1, wherein the skeletal muscle-derived myoblasts are histocompatibly-matched with the recipient.

3. The method according to claim 1, wherein the skeletal muscle-derived myoblasts are introduced in a composition comprising a physiologically acceptable medium.

4. The method according to claim 1, wherein the skeletal muscle-derived myoblasts are introduced in an amount of about $10^5$ to $10^6$ cells per $cm^3$ of tissue to be treated in a physiologically acceptable medium.

5. The method according to claim 1, wherein a cloned population of the skeletal muscle-derived myoblasts is introduced into the recipient.

6. The method according to claim 1, wherein the skeletal muscle-derived myoblasts are contacted with a cytokine or growth factor selected from one or more of basic fibroblast growth factor (b-FGF), insulin-like growth factor (IGF), or nerve growth factor (NGF), prior to introducing the skeletal muscle-derived myoblasts into the recipient.

7. The method according to claim 1, wherein the skeletal muscle-derived myoblasts carry a vector containing a heterologous gene.

---

---

What is claimed is:

1. A method of augmenting skeletal muscle tissue in a subject in need thereof comprising:

introducing an isolated population of cells enriched in viable, non-fibroblast, desmin-expressing, autologous, skeletal muscle-derived myoblasts into a site of injured or damaged skeletal muscle tissue of a recipient in an 8. The method according to claim 1, wherein the skeletal muscle-derived myoblasts have been obtained according to a culture method comprising:

(i) plating a suspension of cells from skeletal muscle tissue in a first container, to which fibroblast cells in the muscle tissue suspension adhere;

(ii) re-plating non-adherent cells from (i) in a second container after approximately 15% to 20% of the cells from the cell suspension have adhered to the first container;

(iii) repeating step (ii) at least one time to enrich for an end population of viable, non-fibroblast, desmin-expressing, skeletal muscle-derived myoblasts; and (iv) isolating the enriched end population of skeletal muscle-derived myoblasts.

9. The method according to claim 1, wherein the population of skeletal muscle-derived myoblasts is enriched to comprise 14% to 95% desmin positive cells.

10. The method according to claim 1, wherein the population of skeletal muscle-derived myoblasts is enriched to comprise 14% to 80% desmin positive cells.

11. The method according to claim 1, wherein the skeletal muscle-derived myoblasts are genetically unmodified.

12. The method of claim 1, wherein the muscle injury is the result of laceration.

13. The method of claim 1, wherein the muscle injury is the result of contusion.

14. The method of claim 1, wherein the muscle injury is the result of strain.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Homo sapiens
<300> PUBLICATION INFORMATION:
<301> AUTHORS: Tzeng, E. et al.
<303> JOURNAL: MOLECULAR  MEDICINE
<304> VOLUME: 2
<306> PAGES: 211-225
<307> DATE: 1996

<400> SEQUENCE: 1
aggacatcct gcggcagc                                                 18

<210> SEQ ID NO 2
<211> LENGTH: 18
<212> TYPE: DNA
<213> ORGANISM: Homo sapiens

<400> SEQUENCE: 2
gctttaaccc ctcctgta                                                 18
```